US008926700B2

(12) United States Patent
Hoy et al.

(10) Patent No.: US 8,926,700 B2
(45) Date of Patent: Jan. 6, 2015

(54) SPINAL FACET JOINT IMPLANT

(75) Inventors: Robert W. Hoy, Paradise, UT (US);
Daniel J. Triplett, Providence, UT (US);
T. Wade Fallin, Hyde Park, UT (US);
Alan Chervitz, Palm Harbor, FL (US);
Daniel F. Justin, Logan, UT (US)

(73) Assignee: Gmedelware 2 LLC, Audubon, PA (US)

( * ) Notice: Subject to any disclaimer, the term of this patent is extended or adjusted under 35 U.S.C. 154(b) by 1725 days.

(21) Appl. No.: 10/860,487

(22) Filed: Jun. 2, 2004

(65) Prior Publication Data
US 2005/0131537 A1 Jun. 16, 2005

Related U.S. Application Data

(60) Provisional application No. 60/545,094, filed on Feb. 17, 2004, provisional application No. 60/545,101, filed on Feb. 17, 2004.

(51) Int. Cl.
A61F 2/44 (2006.01)
A61F 2/46 (2006.01)
A61B 17/70 (2006.01)
A61B 17/86 (2006.01)
A61F 2/30 (2006.01)

(52) U.S. Cl.
CPC ........... *A61F 2/4611* (2013.01); *A61B 17/7067* (2013.01); *A61B 17/7049* (2013.01);
(Continued)

(58) Field of Classification Search
CPC .......................... A61F 2/4405; A61B 17/7064
USPC ............................................ 623/17.11–17.12
See application file for complete search history.

(56) References Cited

U.S. PATENT DOCUMENTS 2,677,369 A 5/1954 Knowles
3,247,000 A 4/1966 Taylor
(Continued)

FOREIGN PATENT DOCUMENTS

CN 2386790 Y 7/2000
EP 408489 A1 1/1991
(Continued)

OTHER PUBLICATIONS

Archus Orthopedics; *Total Facet Arthroplasty System* (*TFAS*™). Website; http://www.archususa.com/Product.html.

(Continued)

*Primary Examiner* — Thomas J Sweet
*Assistant Examiner* — Cheryl Miller

(57) ABSTRACT

Superior and/or inferior facets of one or more facet joints may be replaced by superior and/or inferior facet joint prostheses. In one embodiment, a kit of superior or inferior prostheses is provided, in which the prostheses have at least two dimensions that vary among members of the kit independently of each other. Each prosthesis may have a bone engaging surface having a surface that is polyaxially rotatable against a corresponding resection of a vertebra. Each prosthesis may also have an articulating surface shaped such that, after attachment to the spine, the replaced or partially replaced facet joints provide a larger medial-lateral range of motion when the spine is flexed than when the spine is extended. Crosslinks may be used to connect left and right prosthesis together in such a manner that they are stabilized in a position in which they are seated directly against the vertebra.

31 Claims, 74 Drawing Sheets

(52) U.S. Cl.
CPC ......... *A61B 17/8625* (2013.01); *A61B 17/8695* (2013.01); *A61B 2017/8655* (2013.01); *A61F 2/30771* (2013.01); *A61F 2/4405* (2013.01); *A61F 2002/30125* (2013.01); *A61F 2002/30154* (2013.01); *A61F 2002/30156* (2013.01); *A61F 2002/30171* (2013.01); *A61F 2002/30426* (2013.01); *A61F 2002/30433* (2013.01); *A61F 2002/30448* (2013.01); *A61F 2002/30514* (2013.01); *A61F 2002/30576* (2013.01); *A61F 2002/30578* (2013.01); *A61F 2002/30579* (2013.01); *A61F 2002/30616* (2013.01); *A61F 2002/30841* (2013.01); *A61F 2002/3085* (2013.01); *A61F 2220/0025* (2013.01); *A61F 2220/0041* (2013.01); *A61F 2220/005* (2013.01); *A61F 2230/0008* (2013.01); *A61F 2230/0021* (2013.01); *A61F 2230/0023* (2013.01); *A61F 2230/005* (2013.01); *A61F 2310/00017* (2013.01); *A61F 2310/00023* (2013.01); *A61F 2310/00203* (2013.01); *A61F 2310/00239* (2013.01); *A61F 2310/00796* (2013.01)
USPC ...................................................... 623/17.11

(56) References Cited

U.S. PATENT DOCUMENTS

| | | |
|---|---|---|
| 3,298,372 A | 1/1967 | Feinberg |
| 3,426,364 A | 2/1969 | Lumb |
| 3,486,505 A | 12/1969 | Morrison |
| 3,508,954 A | 4/1970 | White et al. |
| 3,648,691 A | 3/1972 | Lumb et al. |
| 3,857,642 A | 12/1974 | Miller |
| 3,867,728 A | 2/1975 | Stubstad et al. |
| 3,875,595 A | 4/1975 | Froning |
| 4,003,376 A | 1/1977 | McKay et al. |
| 4,092,078 A | 5/1978 | Klotz et al. |
| 4,289,123 A | 9/1981 | Dunn |
| 4,349,921 A | 9/1982 | Kuntz |
| 4,369,769 A | 1/1983 | Edwards |
| 4,479,491 A | 10/1984 | Martin |
| 4,483,334 A | 11/1984 | Murray |
| 4,501,269 A | 2/1985 | Bagby |
| 4,554,914 A | 11/1985 | Kapp et al. |
| 4,599,086 A | 7/1986 | Doty |
| 4,604,995 A | 8/1986 | Stephens et al. |
| 4,611,581 A | 9/1986 | Steffee |
| 4,641,636 A | 2/1987 | Cotrel |
| 4,653,481 A | 3/1987 | Howland et al. |
| 4,657,550 A | 4/1987 | Daher |
| 4,696,290 A | 9/1987 | Steffee |
| 4,743,260 A | 5/1988 | Burton |
| 4,759,769 A | 7/1988 | Hedman et al. |
| 4,772,287 A | 9/1988 | Ray et al. |
| 4,790,303 A | 12/1988 | Steffee |
| 4,800,874 A | 1/1989 | David et al. |
| 4,805,602 A | 2/1989 | Puno et al. |
| 4,827,918 A | 5/1989 | Olerud |
| 4,863,476 A | 9/1989 | Shepperd |
| 4,863,477 A | 9/1989 | Monson |
| 4,892,545 A | 1/1990 | Day et al. |
| 4,904,260 A | 2/1990 | Ray et al. |
| 4,911,718 A | 3/1990 | Lee et al. |
| 4,946,458 A | 8/1990 | Harms et al. |
| 4,955,908 A | 9/1990 | Frey et al. |
| 5,011,484 A | 4/1991 | Breard |
| 5,015,255 A | 5/1991 | Kuslich |
| 5,047,055 A | 9/1991 | Bao et al. |
| 5,071,437 A | 12/1991 | Steffee |
| 5,092,866 A | 3/1992 | Breard et al. |
| 5,092,867 A | 3/1992 | Harms et al. |
| 5,092,893 A | 3/1992 | Smith |
| 5,127,912 A | 7/1992 | Ray et al. |
| 5,129,900 A | 7/1992 | Asher et al. |
| 5,147,361 A | 9/1992 | Ojima et al. |
| 5,147,404 A | 9/1992 | Downey |
| 5,171,279 A | 12/1992 | Mathews |
| 5,171,280 A | 12/1992 | Baumgartner |
| 5,180,393 A | 1/1993 | Commarmond |
| 5,192,326 A | 3/1993 | Bao et al. |
| 5,236,460 A | 8/1993 | Barber |
| 5,246,458 A | 9/1993 | Graham |
| 5,258,031 A | 11/1993 | Salib et al. |
| 5,261,910 A | 11/1993 | Warden et al. |
| 5,263,953 A | 11/1993 | Bagby |
| 5,282,863 A | 2/1994 | Burton |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner et al. |
| 5,313,962 A | 5/1994 | Obenchain |
| 5,318,567 A | 6/1994 | Vichard |
| 5,360,430 A | 11/1994 | Lin |
| 5,366,455 A | 11/1994 | Dove et al. |
| 5,370,697 A | 12/1994 | Baumgartner |
| 5,375,823 A | 12/1994 | Navas |
| 5,387,213 A | 2/1995 | Breard et al. |
| 5,391,168 A | 2/1995 | Sanders et al. |
| 5,401,269 A | 3/1995 | Buttner-Janz et al. |
| 5,415,661 A | 5/1995 | Holmes |
| 5,437,669 A | 8/1995 | Yuan et al. |
| 5,437,672 A | 8/1995 | Alleyne |
| 5,439,464 A | 8/1995 | Shapiro |
| 5,443,516 A | 8/1995 | Albrektsson et al. |
| 5,456,722 A | 10/1995 | Mcleod et al. |
| 5,458,641 A | 10/1995 | Ramirez Jimenez |
| 5,458,642 A | 10/1995 | Beer et al. |
| 5,458,643 A | 10/1995 | Oka et al. |
| 5,464,439 A | 11/1995 | Gendler |
| 5,470,333 A | 11/1995 | Ray |
| 5,476,463 A | 12/1995 | Boachie-Adjei et al. |
| 5,480,401 A | 1/1996 | Navas |
| 5,489,308 A | 2/1996 | Kuslich et al. |
| 5,496,318 A | 3/1996 | Howland et al. |
| 5,507,745 A | 4/1996 | Logroscino et al. |
| 5,507,813 A | 4/1996 | Dowd et al. |
| 5,514,180 A | 5/1996 | Heggeness et al. |
| 5,522,899 A | 6/1996 | Michelson |
| 5,527,312 A | 6/1996 | Ray |
| 5,531,745 A | 7/1996 | Ray |
| 5,531,747 A | 7/1996 | Ray |
| 5,534,028 A | 7/1996 | Bao et al. |
| 5,534,030 A | 7/1996 | Navarro et al. |
| 5,534,031 A | 7/1996 | Matsuzaki et al. |
| 5,540,688 A | 7/1996 | Navas |
| 5,545,166 A | 8/1996 | Howland |
| 5,545,229 A | 8/1996 | Parsons et al. |
| 5,549,607 A | 8/1996 | Olson et al. |
| 5,556,431 A | 9/1996 | Buttner-Janz |
| 5,556,687 A | 9/1996 | McMillin |
| 5,562,735 A | 10/1996 | Margulies |
| 5,562,736 A | 10/1996 | Ray et al. |
| 5,562,737 A | 10/1996 | Graf |
| 5,569,248 A | 10/1996 | Mathews |
| 5,571,189 A | 11/1996 | Kuslich |
| 5,571,191 A | 11/1996 | Fitz |
| 5,572,191 A | 11/1996 | Lundberg |
| 5,582,612 A | 12/1996 | Lin |
| 5,584,832 A | 12/1996 | Schlapfer |
| 5,603,713 A | 2/1997 | Aust et al. |
| 5,609,634 A | 3/1997 | Voydeville |
| 5,645,597 A | 7/1997 | Krapiva |
| 5,645,599 A | 7/1997 | Samani |
| 5,649,926 A | 7/1997 | Howland |
| 5,653,762 A | 8/1997 | Pisharodi |
| 5,666,243 A | 9/1997 | Brent |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,681,310 A | 10/1997 | Yuan et al. |
| 5,683,464 A | 11/1997 | Wagner et al. |

(56) References Cited

U.S. PATENT DOCUMENTS

| | | | |
|---|---|---|---|
| 5,683,465 A | 11/1997 | Shinn et al. | |
| 5,688,272 A | 11/1997 | Montague et al. | |
| 5,690,629 A | 11/1997 | Asher et al. | |
| 5,702,392 A | 12/1997 | Wu et al. | |
| 5,702,450 A | 12/1997 | Bisserie | |
| 5,702,453 A | 12/1997 | Rabbe et al. | |
| 5,704,936 A | 1/1998 | Mazel | |
| 5,713,900 A | 2/1998 | Benzel et al. | |
| 5,716,415 A | 2/1998 | Steffee | |
| 5,725,582 A | 3/1998 | Bevan et al. | |
| 5,728,097 A | 3/1998 | Mathews | |
| 5,735,899 A | 4/1998 | Schwartz et al. | |
| 5,749,873 A | 5/1998 | Fairley | |
| 5,755,796 A | 5/1998 | Ibo et al. | |
| 5,772,661 A | 6/1998 | Michelson | |
| 5,797,909 A | 8/1998 | Michelson | |
| 5,814,046 A | 9/1998 | Hopf | |
| 5,824,093 A | 10/1998 | Ray et al. | |
| 5,824,094 A | 10/1998 | Serhan et al. | |
| 5,836,948 A | 11/1998 | Zucherman et al. | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,888,223 A | 3/1999 | Bray, Jr. | |
| 5,893,889 A | 4/1999 | Harrington | |
| RE36,221 E | 6/1999 | Breard et al. | |
| 5,916,267 A | 6/1999 | Tienboon | |
| 5,951,555 A | 9/1999 | Rehak et al. | |
| 5,961,516 A | 10/1999 | Graf | |
| 5,986,169 A | 11/1999 | Gjunter | |
| 6,001,130 A | 12/1999 | Bryan et al. | |
| 6,004,322 A | 12/1999 | Bernstein | |
| 6,014,588 A | 1/2000 | Fitz | |
| 6,019,759 A | 2/2000 | Rogozinski | |
| 6,019,792 A | 2/2000 | Cauthen | |
| 6,039,761 A | 3/2000 | Li et al. | |
| 6,039,763 A | 3/2000 | Shelokov | |
| 6,048,342 A | 4/2000 | Zucherman et al. | |
| 6,063,088 A | 5/2000 | Winslow | |
| 6,063,121 A | 5/2000 | Xavier et al. | |
| 6,066,325 A | 5/2000 | Wallace et al. | |
| 6,068,630 A | 5/2000 | Zucherman et al. | |
| RE36,758 E | 6/2000 | Fitz | |
| 6,074,390 A | 6/2000 | Zucherman et al. | |
| 6,080,157 A | 6/2000 | Cathro et al. | |
| 6,090,112 A | 7/2000 | Zucherman et al. | |
| 6,093,205 A | 7/2000 | McLeod et al. | |
| 6,113,637 A | 9/2000 | Gill et al. | |
| 6,113,639 A | 9/2000 | Ray et al. | |
| 6,132,464 A * | 10/2000 | Martin | 623/17.15 |
| 6,132,465 A | 10/2000 | Ray et al. | |
| 6,146,421 A | 11/2000 | Gordon et al. | |
| 6,149,652 A | 11/2000 | Zucherman et al. | |
| 6,151,934 A | 11/2000 | Chong et al. | |
| 6,152,926 A | 11/2000 | Zucherman et al. | |
| 6,156,038 A | 12/2000 | Zucherman et al. | |
| 6,156,067 A | 12/2000 | Bryan et al. | |
| 6,176,861 B1 | 1/2001 | Bernstein et al. | |
| 6,179,838 B1 | 1/2001 | Fiz | |
| 6,183,471 B1 | 2/2001 | Zucherman et al. | |
| 6,189,422 B1 | 2/2001 | Stihl | |
| 6,190,387 B1 | 2/2001 | Zucherman et al. | |
| 6,190,414 B1 | 2/2001 | Young et al. | |
| 6,206,882 B1 | 3/2001 | Cohen | |
| 6,206,922 B1 | 3/2001 | Zdeblick et al. | |
| 6,228,118 B1 | 5/2001 | Gordon | |
| 6,235,030 B1 | 5/2001 | Zucherman et al. | |
| 6,238,397 B1 | 5/2001 | Zucherman et al. | |
| 6,241,730 B1 | 6/2001 | Alby | |
| 6,264,655 B1 | 7/2001 | Pisharodi | |
| 6,267,764 B1 | 7/2001 | Elberg | |
| 6,280,444 B1 | 8/2001 | Zucherman et al. | |
| 6,290,700 B1 | 9/2001 | Schmotzer | |
| 6,293,949 B1 | 9/2001 | Justis et al. | |
| 6,312,469 B1 | 11/2001 | Gielen et al. | |
| 6,314,325 B1 | 11/2001 | Fitz | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,402,750 B1 | 6/2002 | Atkinson et al. | |
| 6,413,259 B1 | 7/2002 | Lyons et al. | |
| 6,419,676 B1 | 7/2002 | Zucherman et al. | |
| 6,419,677 B2 | 7/2002 | Zucherman et al. | |
| 6,419,703 B1 | 7/2002 | Fallin et al. | |
| 6,419,704 B1 | 7/2002 | Ferree | |
| 6,440,169 B1 | 8/2002 | Elberg et al. | |
| 6,447,546 B1 | 9/2002 | Bramlet et al. | |
| 6,451,019 B1 | 9/2002 | Zucherman et al. | |
| 6,451,020 B1 | 9/2002 | Zucherman et al. | |
| 6,458,131 B1 | 10/2002 | Ray | |
| 6,461,359 B1 | 10/2002 | Tribus et al. | |
| 6,471,704 B2 | 10/2002 | Gertzbein et al. | |
| 6,475,219 B1 | 11/2002 | Shelokov | |
| 6,478,796 B2 | 11/2002 | Zucherman et al. | |
| 6,481,440 B2 | 11/2002 | Gielen et al. | |
| 6,485,518 B1 | 11/2002 | Cornwall et al. | |
| 6,500,178 B2 | 12/2002 | Zucherman et al. | |
| 6,514,256 B2 | 2/2003 | Zucherman et al. | |
| 6,527,806 B2 | 3/2003 | Ralph et al. | |
| 6,540,747 B1 | 4/2003 | Marino | |
| 6,540,785 B1 | 4/2003 | Gill et al. | |
| 6,565,605 B2 | 5/2003 | Goble et al. | |
| 6,579,319 B2 | 6/2003 | Goble et al. | |
| 6,582,433 B2 | 6/2003 | Yun | |
| 6,585,769 B1 | 7/2003 | Muhanna et al. | |
| 6,610,091 B1 | 8/2003 | Reiley | |
| 6,616,669 B2 | 9/2003 | Ogilvie et al. | |
| 6,626,909 B2 | 9/2003 | Chin | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,652,585 B2 | 11/2003 | Lange | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,733,534 B2 | 5/2004 | Sherman | |
| 6,761,719 B2 | 7/2004 | Justis et al. | |
| 6,761,720 B1 | 7/2004 | Senegas | |
| 6,783,527 B2 | 8/2004 | Drewry et al. | |
| 6,796,983 B1 | 9/2004 | Zucherman et al. | |
| 6,811,567 B2 | 11/2004 | Reiley | |
| 6,835,205 B2 | 12/2004 | Atkinson et al. | |
| 6,835,207 B2 | 12/2004 | Zacouto et al. | |
| 7,051,451 B2 * | 5/2006 | Augostino et al. | 33/512 |
| 7,087,084 B2 | 8/2006 | Reiley | |
| 2001/0007073 A1 | 7/2001 | Zucherman et al. | |
| 2001/0012938 A1 | 8/2001 | Zucherman et al. | |
| 2001/0016743 A1 | 8/2001 | Zucherman et al. | |
| 2001/0021850 A1 | 9/2001 | Zucherman et al. | |
| 2001/0031965 A1 | 10/2001 | Zucherman et al. | |
| 2001/0039452 A1 | 11/2001 | Zucherman et al. | |
| 2002/0029039 A1 | 3/2002 | Zucherman et al. | |
| 2002/0065557 A1 | 5/2002 | Goble et al. | |
| 2002/0072800 A1 | 6/2002 | Goble et al. | |
| 2002/0091446 A1 | 7/2002 | Zucherman et al. | |
| 2002/0099384 A1 | 7/2002 | Scribner et al. | |
| 2002/0116000 A1 | 8/2002 | Zucherman et al. | |
| 2002/0123806 A1 | 9/2002 | Reiley | |
| 2002/0143331 A1 | 10/2002 | Zucherman et al. | |
| 2002/0151895 A1 | 10/2002 | Soboleski et al. | |
| 2002/0183746 A1 | 12/2002 | Zucherman et al. | |
| 2003/0004572 A1 | 1/2003 | Goble et al. | |
| 2003/0009226 A1 | 1/2003 | Graf | |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0065330 A1 | 4/2003 | Zucherman et al. | |
| 2003/0073998 A1 | 4/2003 | Pagliuca et al. | |
| 2003/0109880 A1 | 6/2003 | Shirado et al. | |
| 2003/0153912 A1 | 8/2003 | Graf | |
| 2003/0191470 A1 | 10/2003 | Ritland | |
| 2003/0220642 A1 | 11/2003 | Freudiger | |

(56) References Cited

U.S. PATENT DOCUMENTS

| | | |
|---|---|---|
| 2003/0220643 A1 | 11/2003 | Ferree |
| 2003/0229346 A1 | 12/2003 | Oribe et al. |
| 2004/0006341 A1 | 1/2004 | Shaolian et al. |
| 2004/0006391 A1 | 1/2004 | Reiley |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0092932 A1 | 5/2004 | Aubin et al. |
| 2004/0106995 A1 | 6/2004 | Le Couedic et al. |
| 2004/0111154 A1 | 6/2004 | Reiley |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143264 A1 | 7/2004 | Mcafee |
| 2004/0147928 A1 | 7/2004 | Landry et al. |
| 2004/0153071 A1 | 8/2004 | Zucherman et al. |
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |
| 2004/0193269 A1* | 9/2004 | Fraser et al. ............... 623/17.11 |
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0033434 A1* | 2/2005 | Berry ...................... 623/17.14 |
| 2005/0033439 A1 | 2/2005 | Gordon et al. |
| 2005/0043797 A1 | 2/2005 | Lee |
| 2005/0043799 A1 | 2/2005 | Reiley |
| 2005/0070899 A1 | 3/2005 | Doubler |
| 2005/0113927 A1 | 5/2005 | Malek |
| 2005/0119657 A1* | 6/2005 | Goldsmith ...................... 606/61 |
| 2005/0119748 A1 | 6/2005 | Reiley et al. |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0154467 A1 | 7/2005 | Peterman et al. |
| 2005/0171609 A1 | 8/2005 | Humphreys |
| 2005/0177166 A1 | 8/2005 | Timm |
| 2005/0228400 A1 | 10/2005 | Chao et al. |
| 2006/0079903 A1 | 4/2006 | Wong |
| 2006/0217718 A1 | 9/2006 | Chervitz |
| 2008/0200918 A1 | 8/2008 | Spitler et al. |
| 2008/0282846 A1 | 11/2008 | Sharifi-Mehr et al. |
| 2009/0163963 A1 | 6/2009 | Berrevoets |

FOREIGN PATENT DOCUMENTS

| | | |
|---|---|---|
| EP | 322334 B1 | 2/1992 |
| EP | 667127 A1 | 8/1995 |
| EP | 767637 A1 | 6/1996 |
| EP | 767637 B1 | 11/1998 |
| EP | 1273269 A3 | 11/1998 |
| EP | 768843 B1 | 2/1999 |
| EP | 2721501 B1 | 2/1999 |
| EP | 669109 B1 | 5/1999 |
| EP | 1239785 B1 | 9/2004 |
| EP | 1343424 B1 | 9/2004 |
| EP | 1399078 B1 | 12/2004 |
| FR | 2709245 B1 | 11/1998 |
| FR | 2709246 B1 | 12/1998 |
| FR | 2709247 A1 | 1/1999 |
| FR | 2721501 A1 | 1/2000 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO 95/05783 | 3/1995 |
| WO | WO 95/05785 | 3/1995 |
| WO | WO9505784 A1 | 3/1995 |
| WO | WO9505786 A1 | 3/1995 |
| WO | WO 96/00049 | 1/1996 |
| WO | WO9822033 A1 | 5/1998 |
| WO | WO 98/48717 | 11/1998 |
| WO | WO9848707 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9960957 C2 | 12/1999 |
| WO | WO9965412 A1 | 12/1999 |
| WO | WO0038582 | 7/2000 |
| WO | WO0062684 A1 | 10/2000 |
| WO | WO 0130248 A1 | 5/2001 |
| WO | WO0141681 A1 | 6/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0197721 A3 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02065954 A1 | 8/2002 |
| WO | WO02067792 A2 | 9/2002 |
| WO | WO02067793 A2 | 9/2002 |
| WO | WO02089712 A1 | 11/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO03041618 A2 | 12/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004032794 A3 | 4/2004 |
| WO | WO2004039239 A2 | 5/2004 |
| WO | WO2004039239 A3 | 5/2004 |

(56) References Cited

FOREIGN PATENT DOCUMENTS

| | | |
|---|---|---|
| WO | WO2004039243 A2 | 5/2004 |
| WO | WO2004039243 A3 | 5/2004 |
| WO | WO2004041066 A2 | 5/2004 |
| WO | WO2004041066 A3 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |
| WO | WO2006102443 | 9/2006 |

OTHER PUBLICATIONS

Todd Anres; *Facet Joint Arthroplasty: A Glimpse of the Future of Spine Technology*, Othopaedic Product News, Sep./Oct. 2005 p. 38,40.

Shaw, M; Development of Artifical Facets—Biomechanical Perspective *51st Annual Metting of the Orthopaedic Research Society, Poster No. 1263*.

Goh JC, et al., "Influence of PLIF cage size on lumbar spine stability", Spine, Jan. 2000 25:1, PubMed abstract.

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Wolf, A et al, Morphometric Study of the Human Lumbar Spine for Operation Workspace Specifications. Spine 2001, 26:22: 2472-2477.

Krag MH, et al. Morphometry of the thoracic and lumbar spine related to transpedicular screw placement for surgical spinal fixation. Spine 1988, 13:1: 27-32.

Panjabi MM, et al, Articular facet of the human spine; Quantitative three-dimensional anatomy. Spine 1993, 18:10: 1298-1310.

Boden SD, et al., Orientation of the lumbar facet joints; Association with degenerative disc desease. JBJS 1996, 78A:3 March, 403-411.

Olsewski JM. et al., Morphometry of the lumbar spine: Anatomical perspectives related to transpedicular fixation. JBJS 1990, 72A:4: 541-549.

Aharinejad S. et al. Morphometric analysis of vertebrae and intervertebral discs and a basis of disc replacement. The Jornal of Anatomy 1990, 189: 69-76.

Buttermann Glenn R. et al. In vivo facet joint loading of the caninie lumbar spine. Spine 1992, 17:1.

Dovorak J. et al., Clinical validation of functional flexion-extension roentgenograms of the lumbar spine. Spine 1991. 16:8.

Ebraheim Nabil A. et al., Projection of the lumber pedicale and its morphometric analysis. Spine 1996. 21:11: 1296-1300.

Ebraheim Nabil A., et al, Quantitative anatomy of the cervical facet and the posterior projection of its inferior facet. Journal of Spinal Disorders 1997. 10;4; 308-316.

Ebraheim Nabil A., et al, Quantitative anatomy of the thoracic facet and the posterior projection of its inferior facet. Spine 1997. 22:16: 1811-1818.

Enker, P. et al., Artificial disc replacement. Spine 1993. 18:8: 1061-1070.

Hart Robert A. et al., Placement of pedicale screws in the thoracic spine: A comparison of two techniques. North American Spine Society 15$^{th}$ Annual meeting. Saturday, Oct. 28, 2000.

Kostuik John P. et al., Intervertebral disc replacement. Clinical Orthopaedics and related research. 1997. 337: 27-41.

Khoo, Lary T., A Biomechanical Analysis of the Effects of Lumbar Fusion of the Adjacetnt Vertebaral Motion Segment. North American Spine Society 15$^{th}$ Annual Meeting. Saturday, Oct. 28, 2000.

Natarajan, R.N. et al., Study on effect of graded facetectomy on change in lumbar motion sevment torsional flexibility using three dimensional continuum contact representation for facet joints. Journal of Biomechanical Engineering, Apr. 1999, 121:215.

Panjabi, Manohar M., Human lumbar vertebrae: Quantitative Three-Dimensional Anatomy. Spine 1992, 17:3.

Panjabi, Manohar M., Biomechanical Time Tolerance of Fresh Cadaveric Human Spine Specimens. Journal of Orthopaedic Research 1985, 3: 292-300.

Panjabi, Manohar M., Physiologic Strains in the Lumbar Spinal Ligaments. Spine 1982, 7:3: 192-203.

Panjabi, Manohar M., Mechanical Behavior of the Human Lumbar and Lumbosacral Spine as shown by Three Dimensional Load Displacement Curves. JBJS Mar. 1994 76A:3.

Schendel Michael J., Experimental Measurement of Ligament Force, Facet Force, and Segment Motion in the Human Lumbar Spine. Journal of Biomechanics 1993, 26:4/5 427-438.

Tulis, Ram S., A Study oif the Angle of Inclination and Facet Curvature of Superior Lumbar Zygapophyseal Facets. Spine 1993, 18:10 1311-1317.

Rongming Xu, et al., The Quantitative Anatomy of the Laminas of the Spine. Spine 1999, 24:2: 107-113.

Panjabi, Manohar M., et al., Basic Biomechanics of the Spine. Neurosurgery 1980. 7:1.

Lemaire, J.P., et al., Intervertebral Disc Prosthesis. Clinical Orthopaedics and Related Research, 337: 64-76.

Nagata, Hiroto, et al., The Effects of Immobilization of Long Segments of the Spine on the Adjacent and Distal Facet Force and Lumbosacral Motion. Spine 18:16 2471-2479.

IPRP and Written Opinion in matter PCT/US2009/066761.

ISR in matter PCT/US2009/066761.

* cited by examiner

SPINAL FACET JOINT IMPLANT

REFERENCE TO PENDING PRIOR APPLICATIONS

The present U.S. provisional application claims the benefit of: (i) U.S. Provisional Patent Ser. No. 60/545,094, filed on Feb. 17, 2004 by Alan Chervitz et al. for SPHERICAL ARTICULATING IMPLANT SURFACE, and (ii) U.S. Provisional Patent Ser. No. 60/545,101, filed on Feb. 17, 2004 by Alan Chervitz et al. for SPHERICAL IMPLANT AND BONE BED. The above-identified documents are incorporated herein by reference.

BACKGROUND OF THE INVENTION

1. Field of the Invention

The present invention relates to surgical devices and methods to guide instruments that prepare the surface of bones and other tissues for implants that replace a damaged, diseased, or otherwise painful spinal facet joint.

2. Description of Related Art

Traumatic, inflammatory, metabolic, and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the U.S. Clinical success varies considerably, depending upon technique and indications, and consideration must be given to the concomitant risks and complications. For example, Tsantrizos and Nibu have shown that spine fusion decreases function by limiting the range of motion for patients in flexion, extension, rotation, and lateral bending. Furthermore, Khoo and Nagata have shown that spine fusion creates increased stresses and, therefore, accelerated degeneration of adjacent non-fused motion segments. Additionally, pseudoarthrosis, as a result of an incomplete or ineffective fusion, may reduce or even eliminate the desired pain relief for the patient. Finally, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc that directly connects two opposed vertebral bodies.

However, the artificial discs proposed to date do not fully address the mechanics of motion of the spinal column. In addition to the intervertebral disc, posterior elements called the facet joints help to support axial, torsional and shear loads that act on the spinal column. Furthermore, the facet joints are diarthroidal joints that provide both sliding articulation and load transmission features. The effects of their absence as a result of facetectomy was observed by Goh to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints, as noted by Lemaire.

U.S. Pat. No. Re. 36,758 to Fitz discloses an artificial facet joint where the inferior facet, the mating superior facet, or both, are resurfaced.

U.S. Pat. No. 6,132,464 to Martin discloses a spinal facet joint prosthesis that is supported on the posterior arch of the vertebra. Extending from this support structure are inferior and/or superior blades that replace the cartilage at the facet joint. The Martin prosthesis generally preserves existing bony structures and therefore does not address pathologies that affect the bone of the facets in addition to affecting the associated cartilage. Furthermore, the Martin invention requires a mating condition between the prosthesis and the posterior arch (also known as the lamina) that is a thin base of curved bone that carries all four facets and the spinous process. Since the posterior arch is a very complex and highly variable anatomic surface, it would be very difficult to design a prosthesis that provides reproducible positioning to correctly locate the cartilage-replacing blades for the facet joints.

Another approach to surgical intervention for spinal facets is provided in WO9848717A1 to Villaret. While Villaret teaches the replacement of spine facets, the replacement is interlocked in a manner to immobilize the joint.

It would therefore be an improvement in the art to provide a vertebral facet replacement device and method that provides a relatively high degree of mobility in the joint, while effectively removing the source of arthritic, traumatic, or other disease mediated pain with a minimum of patient discomfort.

SUMMARY OF THE INVENTION

In order to overcome the shortcomings of the prior art, the present invention provides a vertebral facet replacement device and method that replaces a bony portion of the facets so as to remove the source of arthritic, traumatic, or other disease mediated pain. Facet joint replacement in conjunction with artificial disc replacements represent a holistic solution to recreating a fully functional motion segment that is compromised due to disease or trauma. Together, facet joint and disc replacement can eliminate all sources of pain, return full function and range of motion, and completely restore the natural biomechanics of the spinal column. Additionally, degenerative or traumatized facet joints may be replaced in the absence of disc replacement when the natural intervertebral disc is unaffected by the disease or trauma.

Accordingly, in certain embodiments, the present invention provides an artificial vertebral facet that replaces the cartilage and a portion of the bone of a facet. Furthermore, the invention may provide a method for preparing a vertebra for the installation of an artificial vertebral facet, a method for replacing a spinal facet, and possibly, a total vertebral facet joint replacement.

The present invention may provide numerous advantages over the prior art. One advantage may be that the quality of attachment of the prosthesis is improved. The present invention may provide a precise press fit into bones, as opposed to relying on prosthetic surfaces mating with highly complex and variable external surfaces of the vertebra, such as the posterior arch or facet. Another advantage may be that the optional porous coating is placed into interior bone spaces where porous coatings have proven to achieve bone ingrowth for excellent long term fixation strength. This ability to achieve bone ingrowth is uncertain for the prior art devices that engage the external bone surfaces of the vertebra. Yet another advantage may lie in the removal of the facet bone structure; where the facet bone is involved in the disease pathology or the trauma that compromised the articular or cartilaginous surface of the facet, resection provides a means for ensuring that all pain associated with the disease or trauma is removed.

The above, and other features and advantages of the present invention, will become apparent from the following description, which is to be read in conjunction with the accompanying drawings.

DETAILED DESCRIPTION OF THE DRAWINGS

Figure 1:
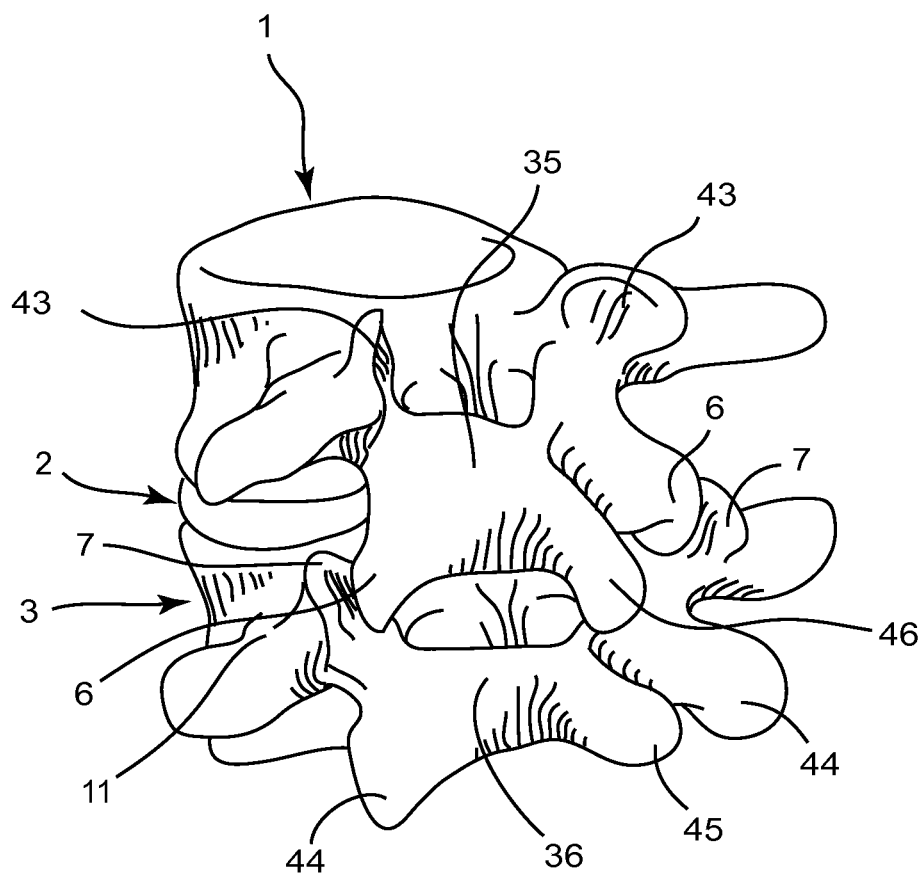
FIG. 1 is a perspective view of a portion of the spine.

Referring now to FIG. 1, there is shown a perspective view of a superior vertebra 1 and an inferior vertebra 3, with an intervertebral disc 2 located in between. The superior vertebra 1 has superior facets 43, inferior facets 6, a posterior arch (or lamina) 35 and a spinous process 46. The inferior vertebra 3 has superior facets 7, inferior facets 44, a posterior arch (or lamina) 36 and a spinous process 45. Each of the vertebrae 1, 3 also has a pair of pedicles 11.

Figure 2:
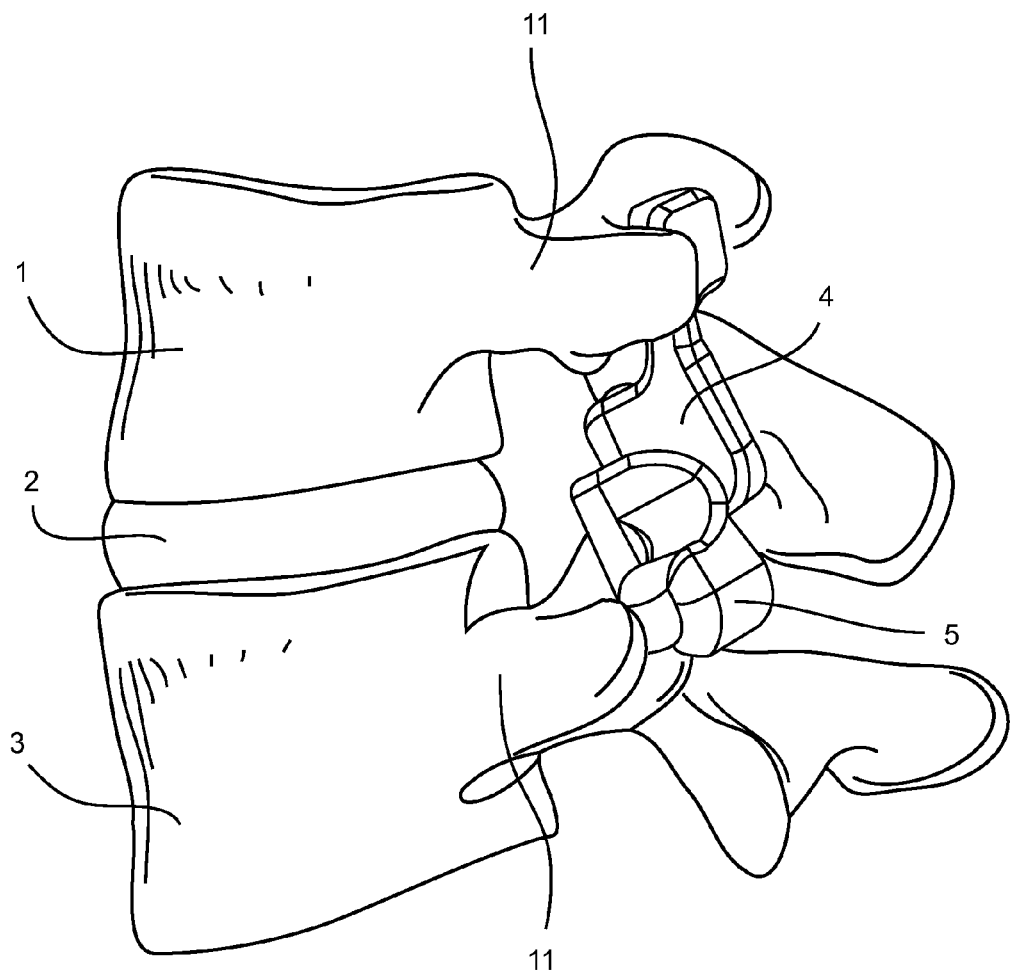
FIG. 2 is a lateral view of a facet joint reconstructed in accordance with the present invention.

Referring now to FIG. 2, in a lateral view, the left inferior facet 6 of the superior vertebra 1 shown in FIG. 1 has been resected and an inferior facet prosthesis 4 has been attached to the superior vertebra 1. Similarly, the left superior facet 7 of the inferior vertebra 3 has been resected and a superior facet prosthesis 5 has been attached to the inferior vertebra 3.

Figure 3:
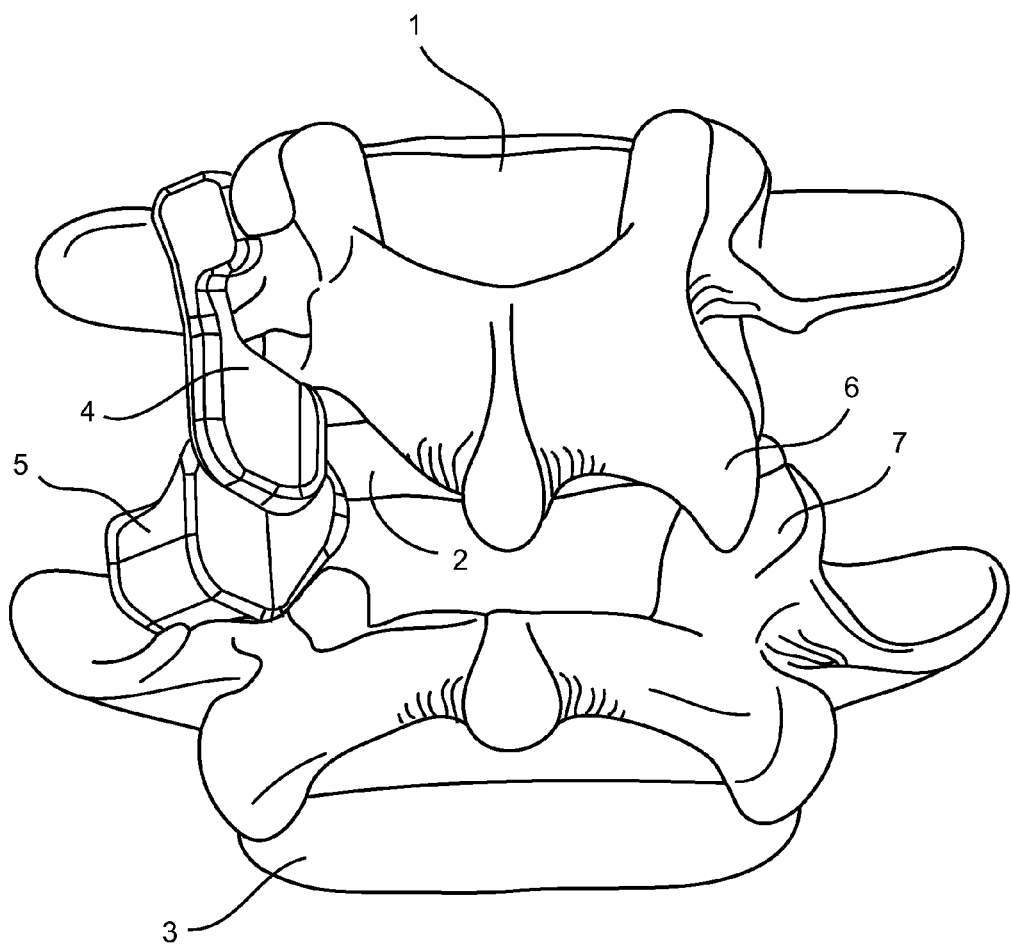
FIG. 3 is a dorsal view of the facet joint shown in FIG. 2.

FIG. 3 illustrates a dorsal view of the elements shown in FIG. 2. It can be appreciated that inferior facet prosthesis 4 replicates the natural anatomy when compared to the contralateral inferior facet 6 of vertebra 1. Similarly, it can be appreciated that superior facet prosthesis 5 replicates the natural anatomy when compared to the contralateral superior facet 7 of vertebra 3. Neither the inferior facet prosthesis 4 nor the superior facet prosthesis 5 rests on the lamina 35.

Figure 4:
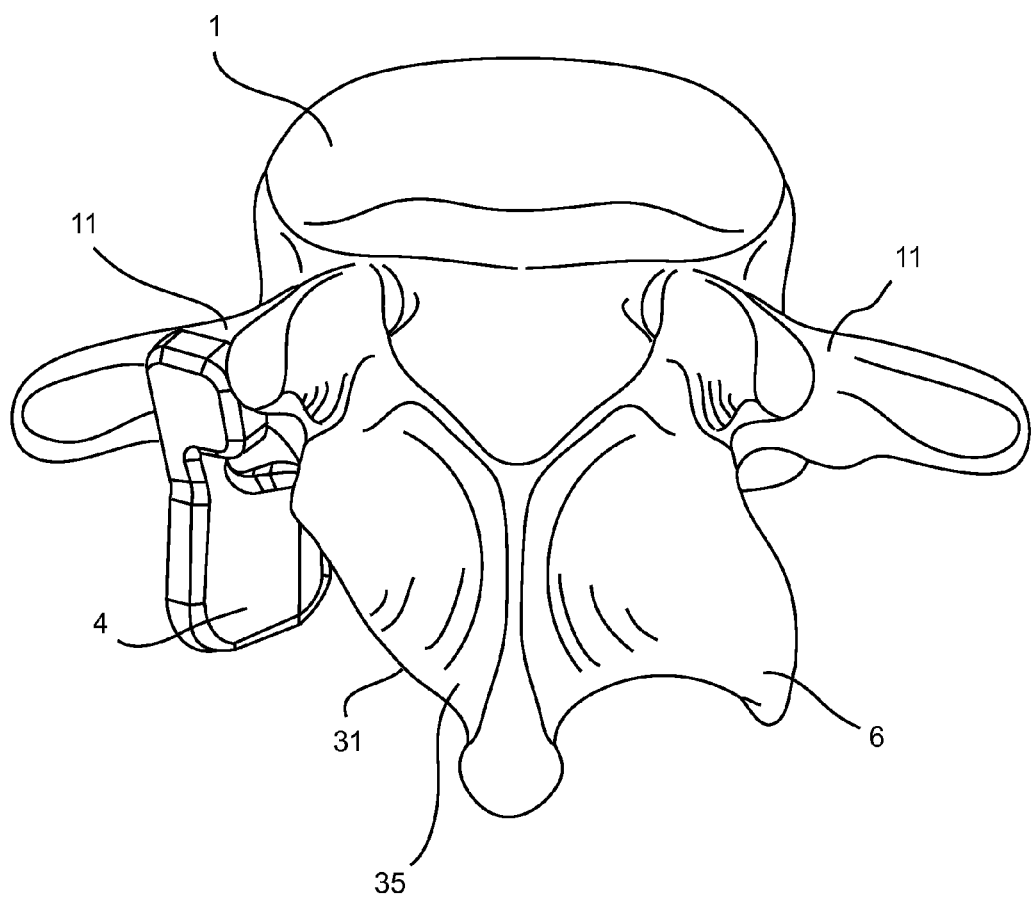
FIG. 4 is a perspective view of the implanted left inferior facet prosthesis shown in FIGS. 2 and 3.

Turning now to FIG. 4, a perspective view of the superior vertebra 1 with implanted inferior facet prosthesis 4 is provided. A bone resection on the left side of the superior vertebra 1, shown as a resection 31, has removed the natural inferior facet 6 at the bony junction between the inferior facet 6 and the lamina 35. In this manner, any bone pain associated with a disease, such as osteoarthritis, or trauma of the left inferior facet 6 will be eliminated as the involved bony tissue has been osteotomized.

Figure 5:
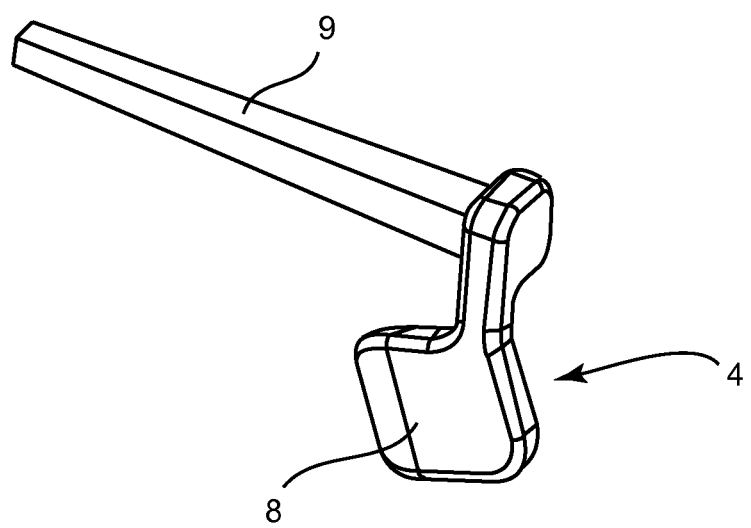
FIG. 5 is a perspective view of the left inferior facet prosthesis shown in FIGS. 2 and 3.

FIG. 5 illustrates a perspective view of the inferior facet prosthesis 4. A surface 8 replicates the natural articular surface of the replaced inferior facet 6. A post 9 provides a mechanism that can be used to affix the inferior facet prosthesis 4 to the superior vertebra 1. The post 9 is implanted into the interior bone space of the left pedicle 11 on the superior vertebra 1 and may or may not extend into the vertebral body of superior vertebra 1 to provide additional stability.

Figure 6:
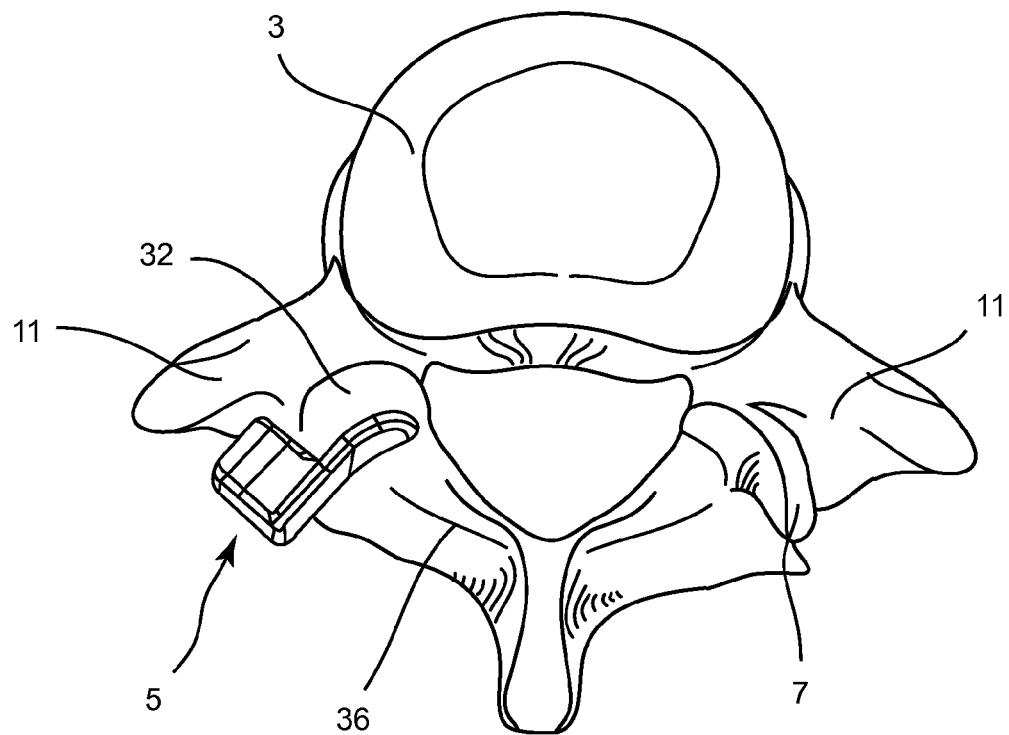
FIG. 6 is a cranial view of the implanted left superior facet prosthesis shown in FIGS. 2 and 3.

FIG. 6 illustrates a cranial view of the inferior vertebra 3 with the implanted superior facet prosthesis 5. A resection surface 32 represents the bony junction between the natural superior facet 7 and the lamina 36.

Figure 7:
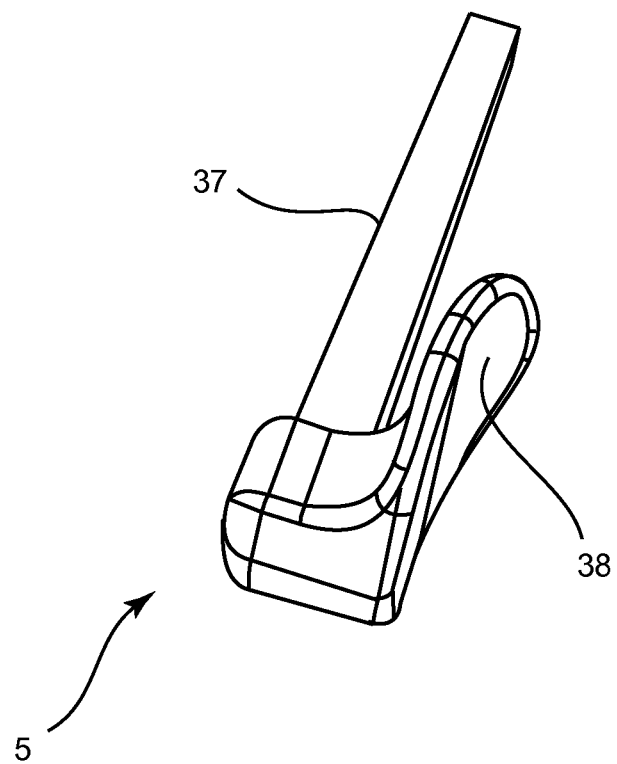
FIG. 7 is a perspective view of the left superior facet prosthesis shown in FIGS. 2 and 3.

FIG. 7 illustrates a perspective view of the superior facet prosthesis 5. A surface 38 replicates the natural articular surface of the replaced superior facet 7. The post 37 provides a mechanism usable to affix the superior facet prosthesis 5 to the inferior vertebra 3. The post 37 is implanted into the interior bone space of the left pedicle 11 (FIG. 6) on the inferior vertebra 3 and may or may not extend into the vertebral body of the inferior vertebra 3 to provide additional stability.

When the total facet joint is replaced, as shown in FIGS. 2 and 3, then the surface 8 (FIG. 5) articulates against the surface 38 (FIG. 7) to recreate the natural biomechanics of the spine motion segment made up of the superior vertebra 1, the inferior vertebra 3, and the intervertebral disc 2. Neither the inferior facet prosthesis 4 nor the superior facet prosthesis 5 rests on the lamina 35 or the lamina 36, respectively.

Figure 8:
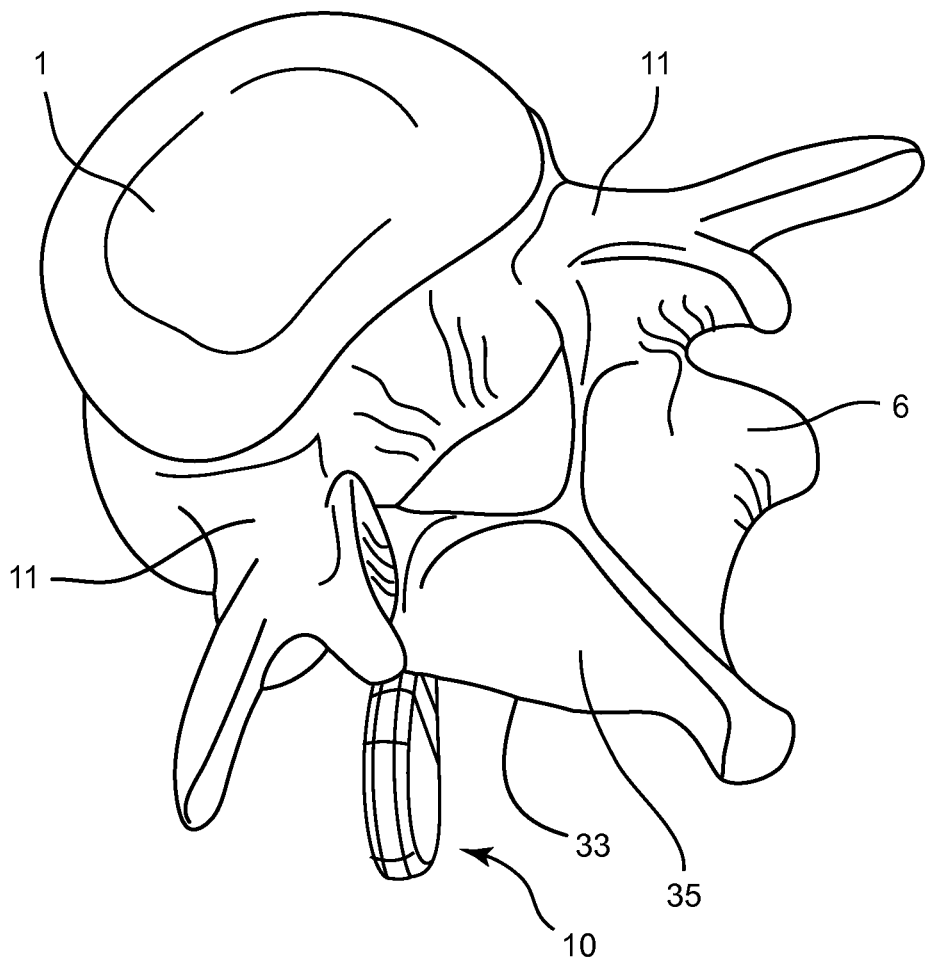
FIG. 8 is a perspective view of an alternative implanted left inferior facet prosthesis.

FIG. 8 illustrates a perspective view of an alternative inferior facet prosthesis 10 that may be implanted into the interior bone space of the lamina 35 of the superior vertebra 1. The interior bone space is accessed from the resection 31.

Figure 9:
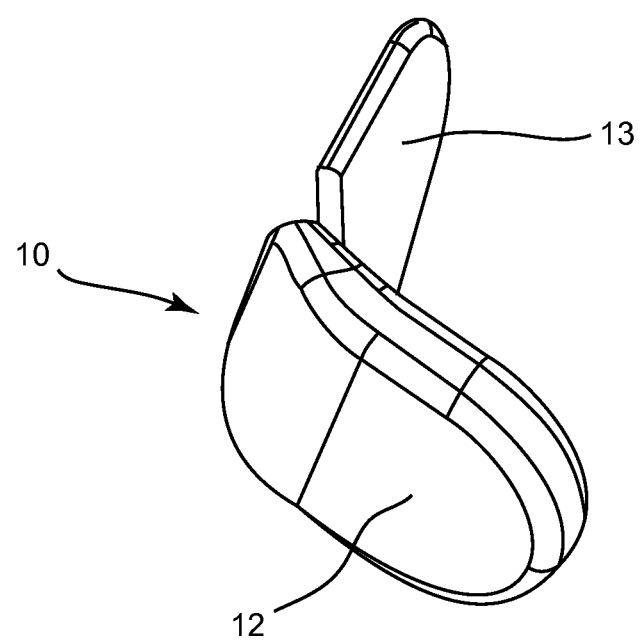
FIG. 9 is a perspective view of an alternative left inferior facet prosthesis.

FIG. 9 shows a perspective view of the alternative inferior facet prosthesis 10, including a fin 13 that extends into the interior bone space of the 35. A surface 12 replicates the natural articular surface of the replaced facet.

The surfaces of the post 9 (FIG. 5), the post 37 (FIG. 7), and the fin 13 (FIG. 9) may or may not include porous coatings to facilitate bone ingrowth to enhance the long-term fixation of the implant. Furthermore, such porous coatings may or may not include osteoinductive or osteoconductive substances to further enhance bone remodeling into the porous coating. In this application, the term "implant" refers to any natural or man-made, fabricated or unfabricated device or group of devices that may be added to a human spine. An implant may include one or more prostheses, one or more fixation devices, and/or other components.

Figure 10:
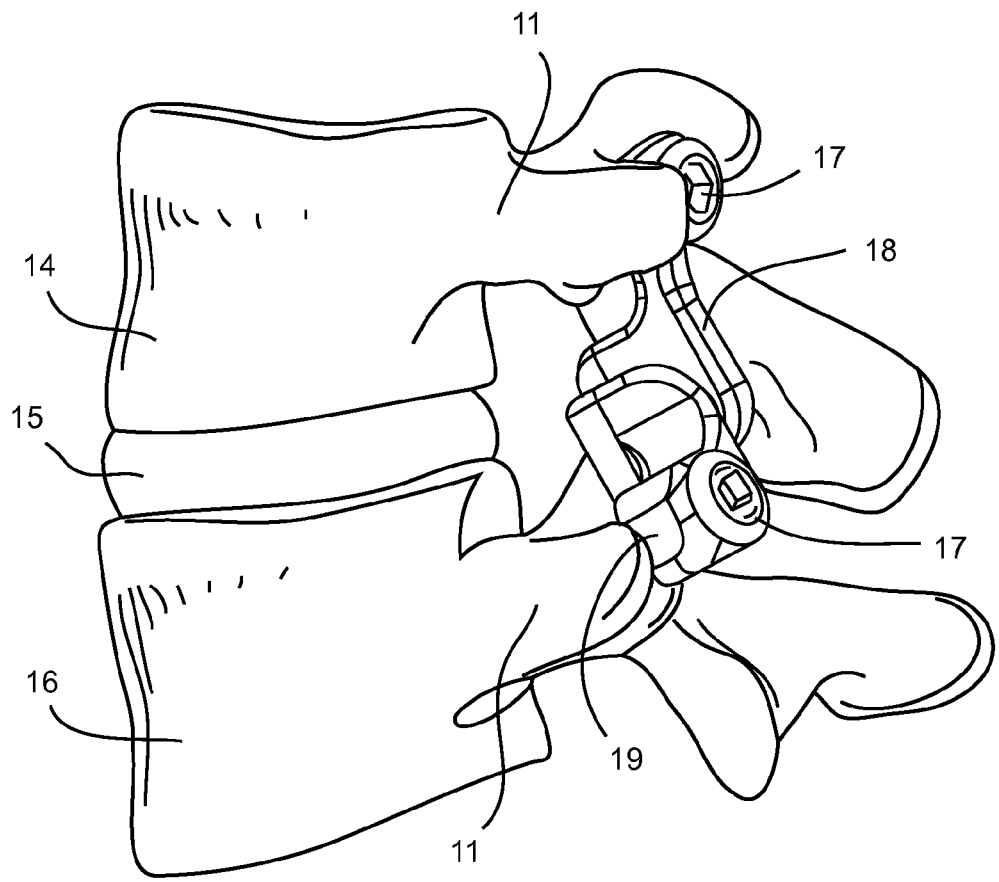
FIG. 10 is a lateral view of an alternative reconstructed facet joint.

Referring now to FIG. 10, there is shown a lateral view of a superior vertebra 14 and an inferior vertebra 16, with an intervertebral disc 15 located in between. The left inferior facet of the superior vertebra 14 has been resected and an inferior facet prosthesis 18 has been attached to superior vertebra 14 via a screw fastener 17. Similarly, the left superior facet of the inferior vertebra 16 has been resected and a superior facet prosthesis 19 has been attached to vertebra 16 via a screw fastener 17.

Figure 11:
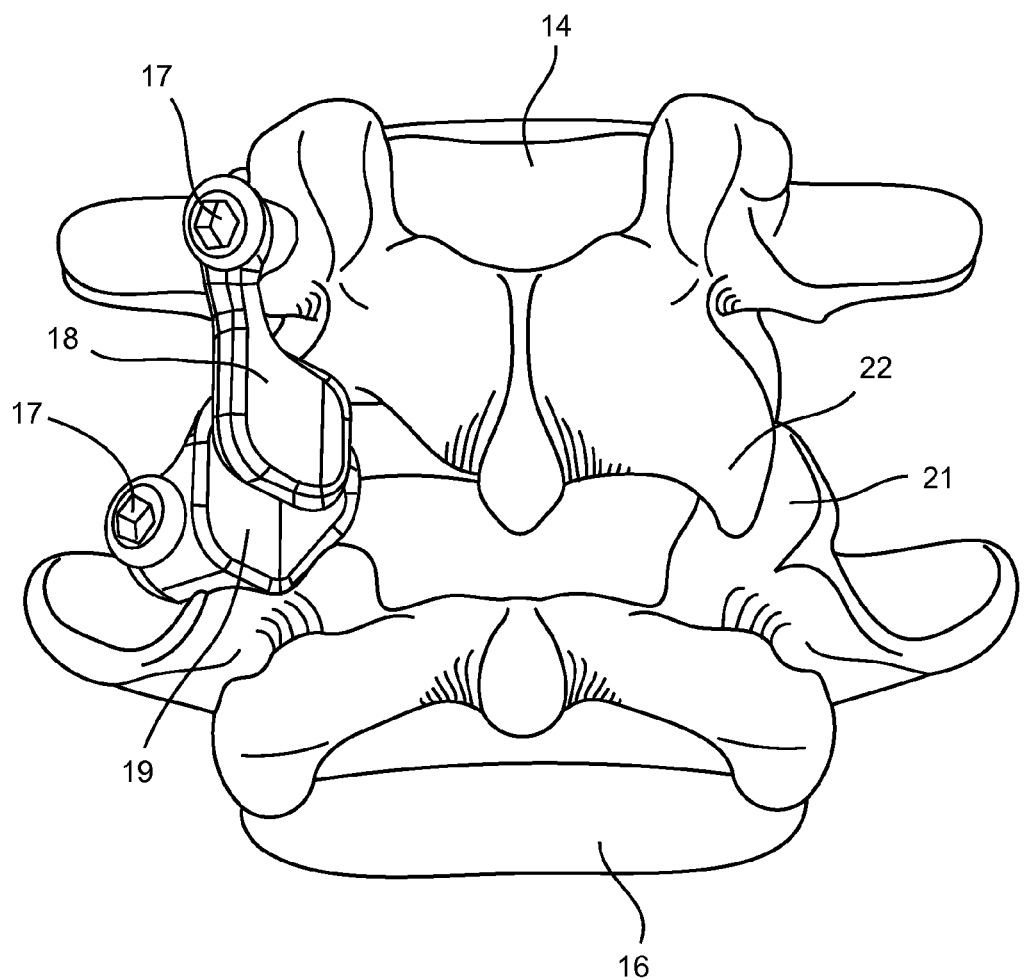
FIG. 11 is a dorsal view of an alternative reconstructed facet joint.

FIG. 11 illustrates a dorsal view of the elements of FIG. 10. It can be appreciated that inferior facet prosthesis 18 replicates the natural anatomy when compared to the contralateral inferior facet 22 of the superior vertebra 14. Similarly, it can be appreciated that superior facet prosthesis 19 replicates the natural anatomy when compared to the contralateral superior facet 21 of the inferior vertebra 16. Neither the inferior facet prosthesis 18 nor the superior facet prosthesis 19 rests on the lamina of the corresponding vertebra 14 or 16.

Figure 12:
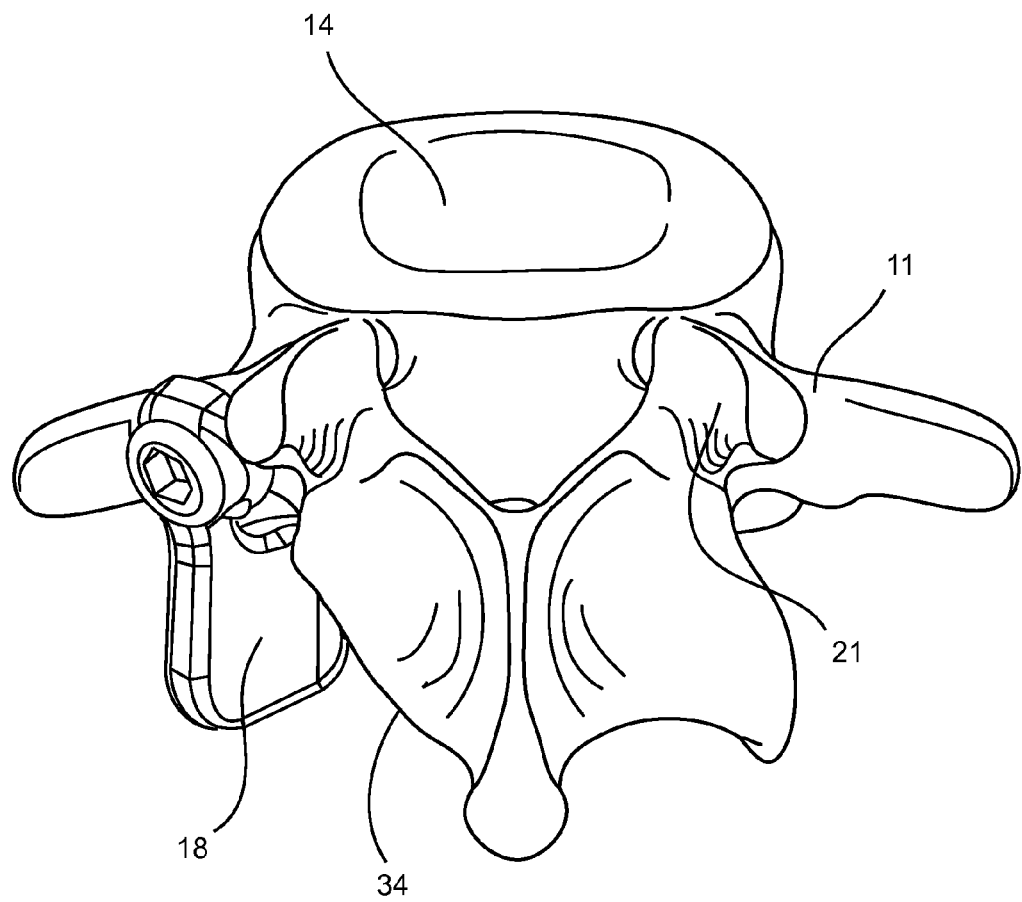
FIG. 12 is a perspective view of the implanted left inferior facet prosthesis shown in FIGS. 10 and 11.

Turning now to FIG. 12, there is provided a perspective view of the superior vertebra 14 with the implanted inferior facet prosthesis 18. A resection 34 has removed the natural inferior facet at the bony junction between the inferior facet and the adjoining lamina. In this manner, any bone pain associated with a disease, such as osteoarthritis, or trauma of the natural inferior facet 22 will be eliminated inasmuch as the involved bony tissue has been osteotomized.

Figure 13:
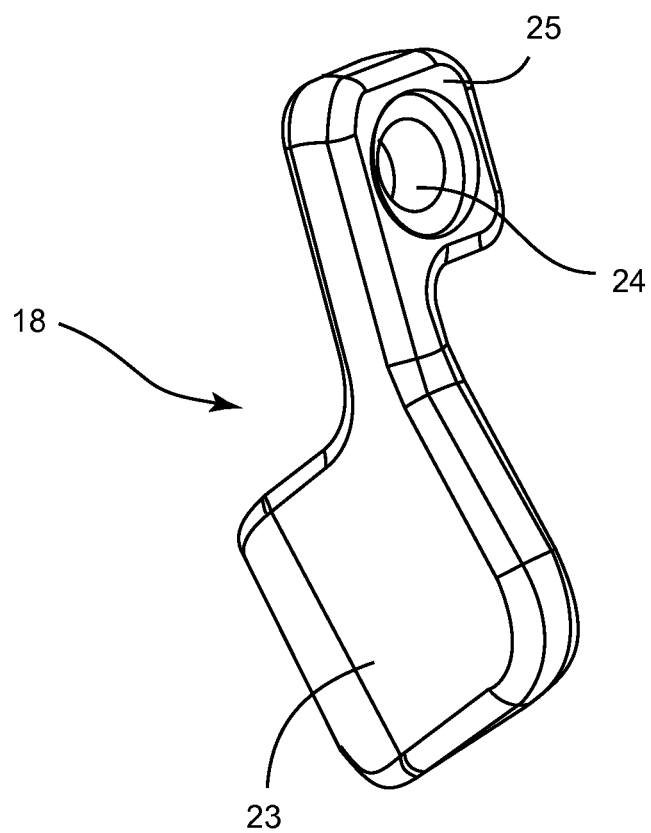
FIG. 13 is a perspective view of the alternative left inferior facet prosthesis shown in FIGS. 10 and 11.

FIG. 13 illustrates a perspective view of the inferior facet prosthesis 18. A surface 23 replicates the natural articular surface of the replaced facet. A flange 25 contacts the pedicle 11 (FIG. 12) and a hole 24 receives the screw fastener 17 to attach the inferior facet prosthesis 18 to the superior vertebra 14.

Figure 14:
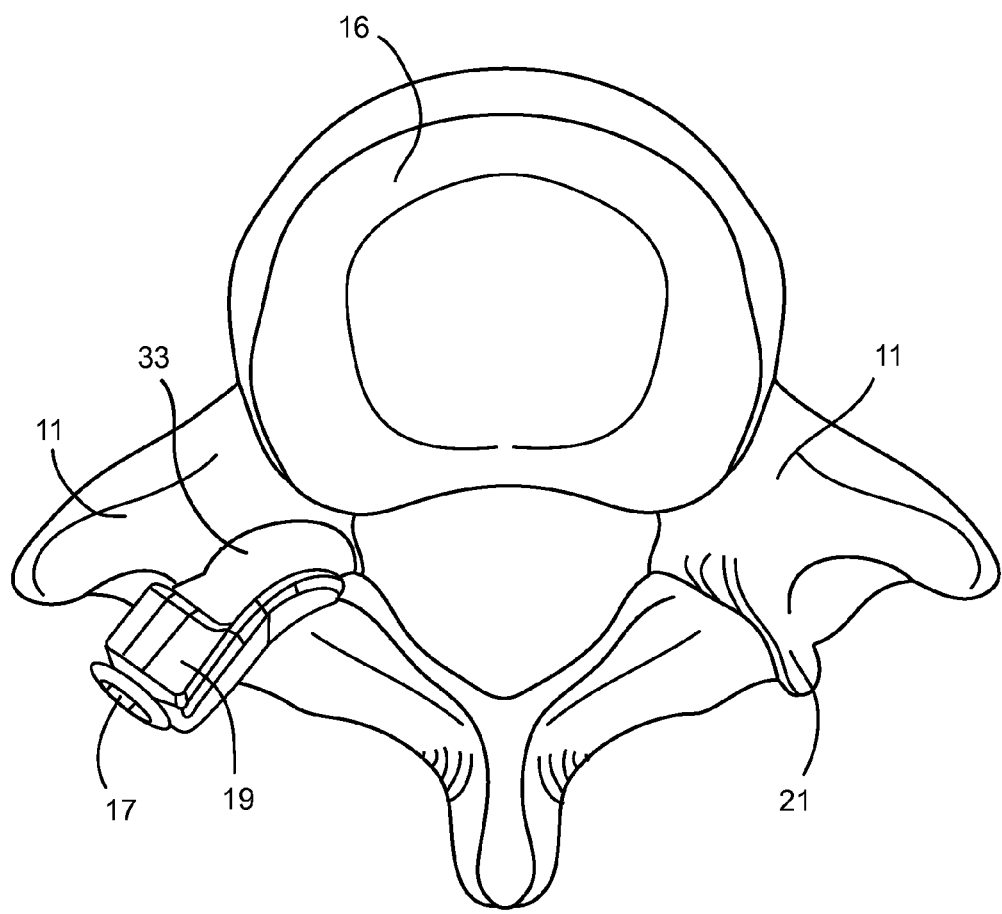
FIG. 14 is a cranial view of the alternative implanted left superior facet prosthesis shown in FIGS. 10 and 11.

FIG. 14 illustrates a cranial view of the inferior vertebra 16 with the implanted superior facet prosthesis 19. A resection surface 33 represents the bony junction between the natural superior facet 21 (FIG. 11) and the corresponding lamina.

Figure 15:
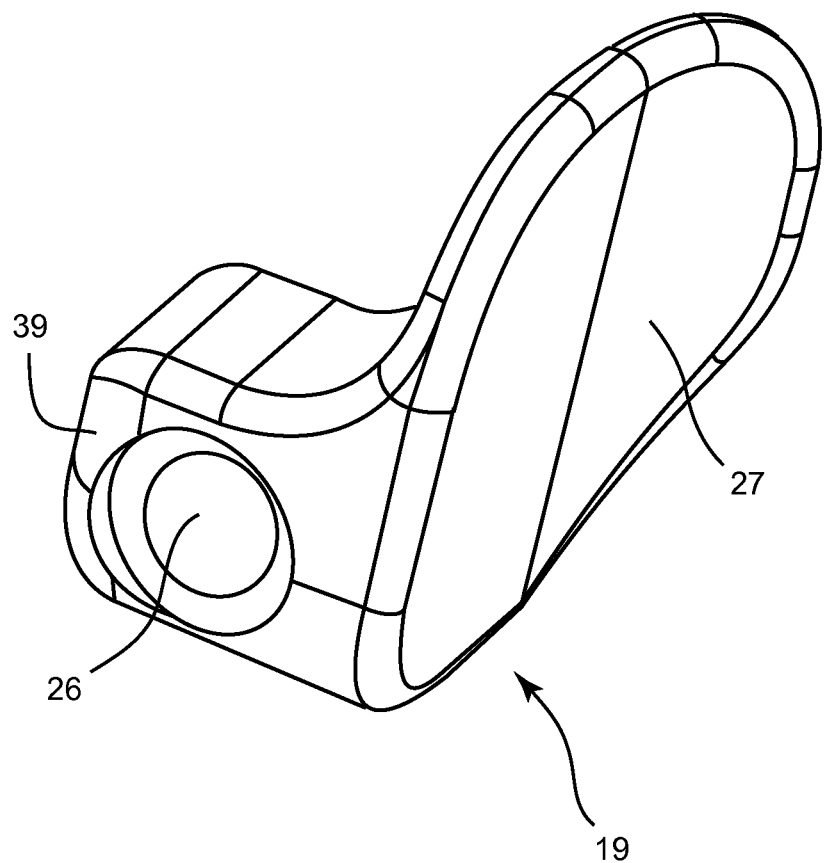
FIG. 15 is a perspective view of the alternative left superior facet prosthesis shown in FIGS. 10 and 11.

FIG. 15 illustrates a perspective view of the superior facet prosthesis 19. A surface 27 replicates the natural articular surface of the replaced facet. A flange 39 contacts the pedicle 11 (FIG. 14) and hole 26 receives a screw fastener 17 to attach the superior facet prosthesis 19 to the inferior vertebra 16.

Figure 16:
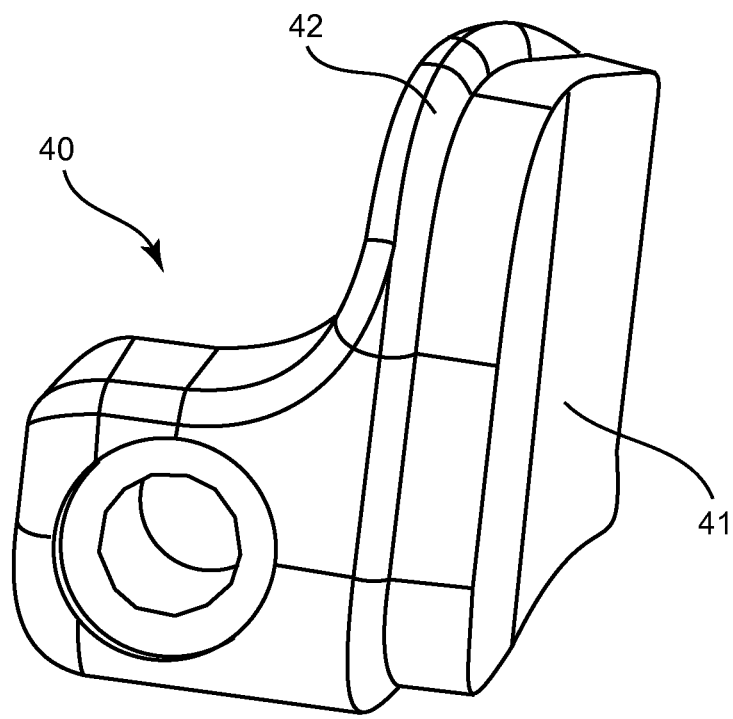
FIG. 16 is a perspective view of an alternative bearing surface for the superior facet prosthesis shown in FIG. 15.

FIG. 16 provides a perspective view of an alternative superior facet prosthesis 40 with a bearing surface 41 that mounts to substrate 42. The bearing surface 41 is a biocompatible polymeric material, such as ultra high molecular weight polyethylene. Alternatively, the bearing surface can be ceramic, such as zirconia or alumina. The substrate is a biocompatible metal alloy, such as an alloy of titanium, cobalt, and/or iron.

The bearing surface 41 may be formed separately from the remainder of the superior facet prosthesis 40, so that the bearing surface 41 and the remainder form components that can be assembled as needed. A kit of differently-sized prostheses may include multiple bearing surfaces like the bearing surface 41 that may have different thicknesses, articulating surface shapes, material selections, and the like. Such a kit may also include other differently-sized components designed such that some subset of the components can be selected and assembled together to provide a prosthesis having the desired dimensions. Prosthesis kits will be shown and described in greater detail subsequently.

Figure 17:
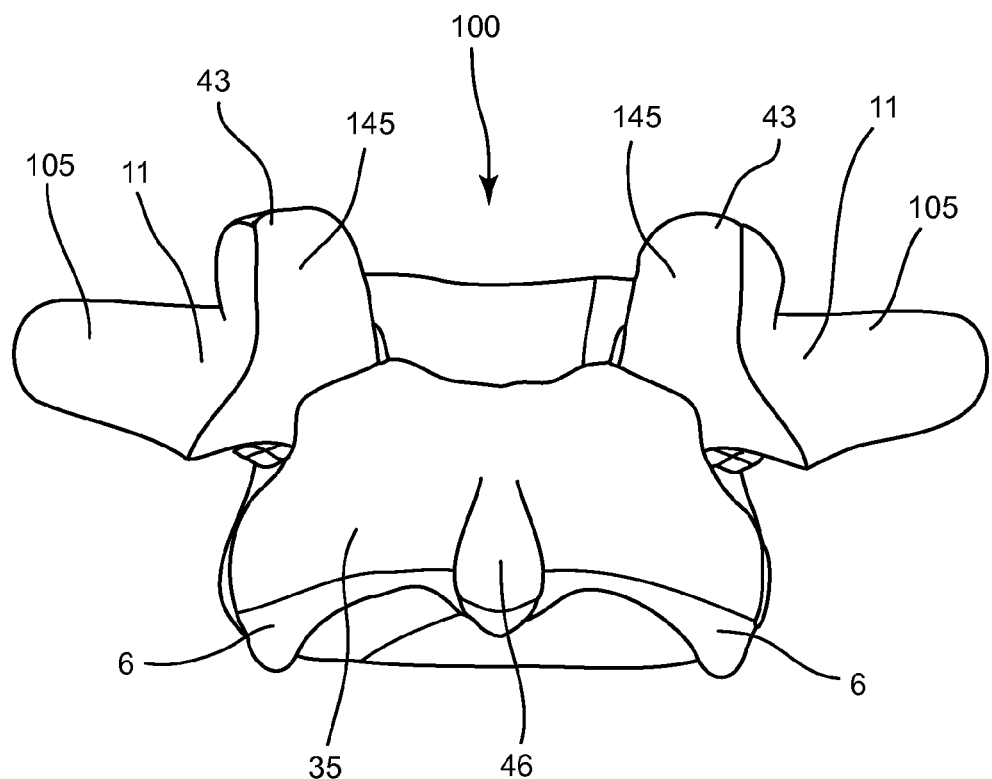
FIG. 17 is a dorsal view of a single intact vertebra.
Figure 18:
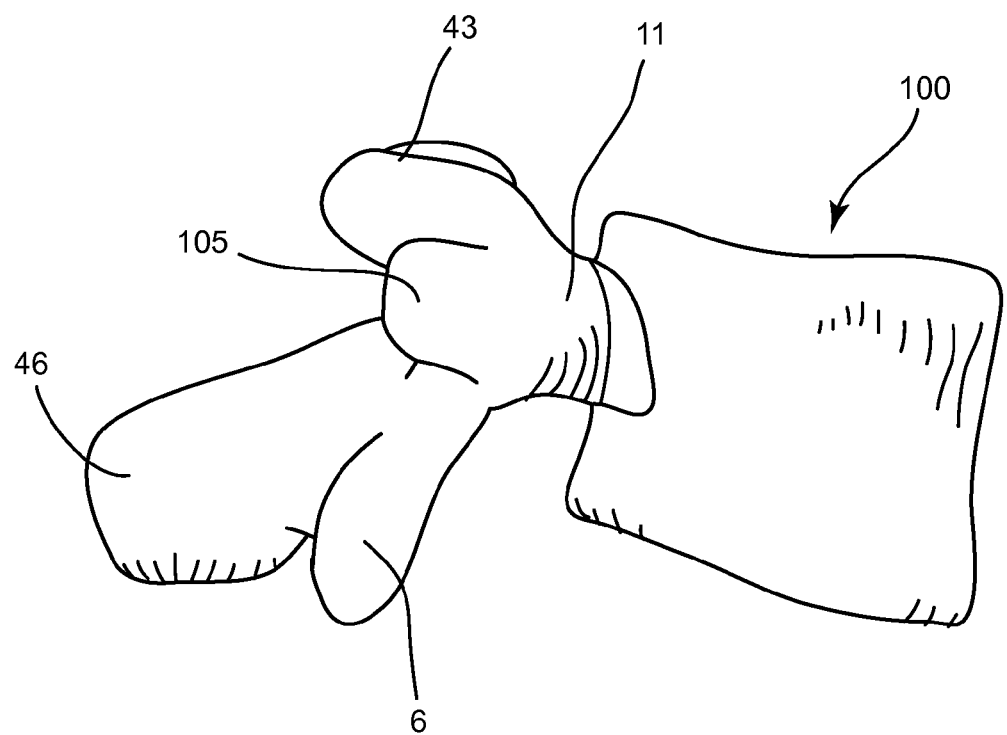
FIG. 18 is a lateral view of the same intact vertebra shown in FIG. 17.

Referring to FIG. 17 and FIG. 18, a single intact vertebra 100 is shown. FIG. 17 is a dorsal view of the vertebra 100. FIG. 18 is a lateral view of the same vertebra 100. Similar to the two vertebrae 1, 3 shown in the portion of the spine illustrated in FIGS. 1 through 3, the vertebra 100 has posterior anatomy comprising left and right superior facets 43 on the superior, or top side in this view of the dorsal vertebra 100, left and right inferior facets 6 on the inferior or bottom side of the posterior vertebra 100, left and right transverse processes 105 extending laterally from the posterior portion of vertebra 100, and left and right pedicles 11. Each of the superior facets 43 has a superior articulating surface 145. The posterior portion of vertebra 100 also has a posterior arch (or lamina) 35, and a spinous process 46 that protrudes from the lamina 35 posteriorly, out of the page in FIG. 17 and to the left in FIG. 18. In FIG. 17, the bony structure of the superior facets 43 and the inferior facets 6 are intact, as it would be presented in a vertebra without significant tissue degeneration or remodeling resulting from facet joint disease. Although the vertebra 100 is shown in FIG. 17 as a generally structurally healthy and intact vertebra, if the vertebra 100 were a diseased vertebra, the vertebra could exhibit signs of facet joint disease.

Consequently, structural pathology related to facet joint disease would likely be visible. For example, the left superior facet 43 and the right superior facet 43 of the vertebra 100 are symmetrical in FIG. 17 and FIG. 18. But in the case of a vertebra 100 with only one diseased joint, the facet on the diseased side would likely be showing pathological signs of disease such as tissue degeneration or inflammation resulting in an asymmetrical structural comparison between the two facets.

Also, in more extreme cases the facet disease could progress to a state in which the articular process of the facet is eroded or inflamed resulting in anatomic morphology that is unique to the pathology of a particular facet joint of an individual patient. This could present unusual facet morphology that could be different from what is shown in FIGS. 17 and 18.

Furthermore, the facet disease could eventually disable the biomechanics of a patient such that the facet joint is essentially non-articulating and immobile. In this case, one superior facet of a first vertebra could essentially be fused to one inferior facet of a second vertebra. Since the structural pathology of the diseased facet is variable, a surgeon may determine that the best bone apposition surface or foundation for securing a facet implant is a resected bone surface.

Figure 19:
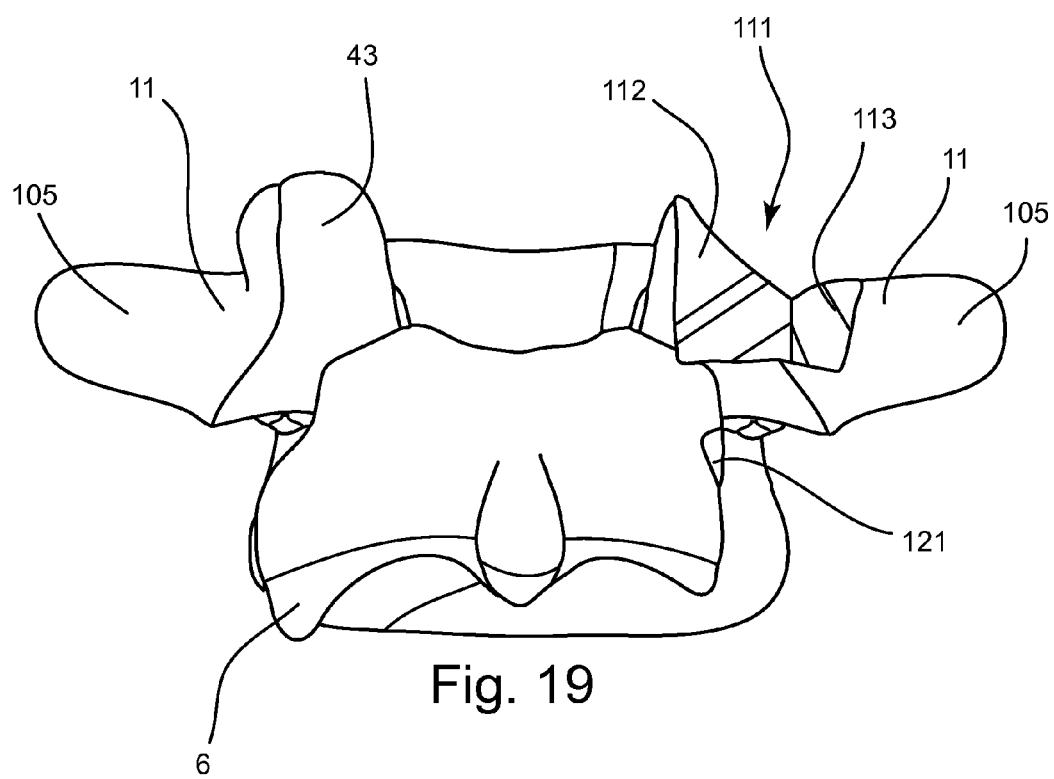
FIG. 19 is a dorsal view of the same vertebra of FIG. 17 and FIG. 18, with a portion of the superior facet resected and a portion of the inferior facet resected.
Figure 20:
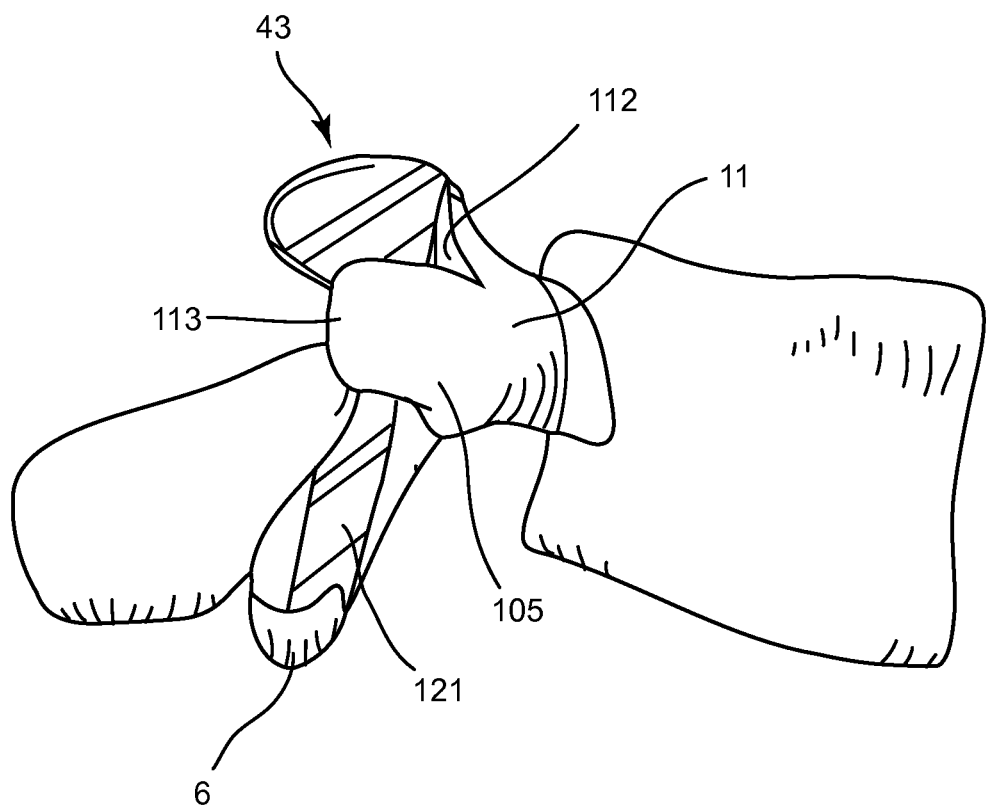
FIG. 20 is a lateral view of the resected vertebra shown in FIG. 19.

Referring to FIG. 19 and FIG. 20 which are dorsal and lateral views of the same vertebra shown in FIG. 17 and FIG. 18 after a portion of the right superior facet 43 and a portion of the right inferior facet 6 have been resected. The removal of a portion of the superior facet 43 by resection results in a superior facet resection 111. In the resection shown in FIG. 19 and FIG. 20, the superior resection 111 has two resulting faces, a first resection surface 112 and a second resection surface 113. Likewise, the inferior facet resection results in an inferior facet resection surface 121.

Figure 22:
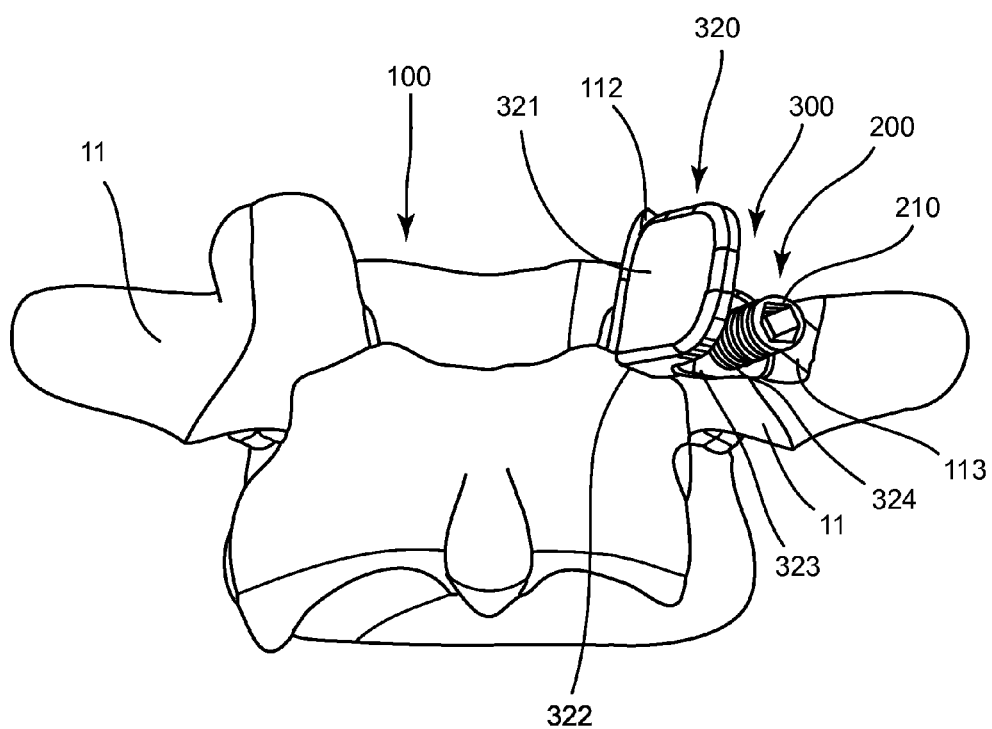
FIG. 22 is a dorsal view showing the resected vertebra, the fixation element, and a superior facet prosthesis.

Tissue removal tools (not shown) such as a bone burr, rasp, reamer, mill, saw, rounger, osteotome or similar tools designed to cut and remove bone tissue can be used to create these resection surfaces. The surgeon uses anatomic landmarks such as the pedicle 11 or transverse process 105 to align the tissue removal tools in such a way as to remove the portion of the facet necessary to provide a superior resection 111 that serves as a bone apposition surface or foundation to eventually support a superior facet prosthesis 300, as shown in FIG. 22. The left superior facet 43 is shown intact in both FIG. 19 and FIG. 20, but a portion of the right superior facet 43 is resected resulting in the first resection surface 112 and the adjacent second resection surface 113 (FIG. 19). The shape of the superior resection 111 will vary in accordance with the structure of the tissue removal tool. In the embodiment shown in FIG. 19 and FIG. 20, the first resection surface 112 and the second resection surface 113 are on approximately perpendicular planes. However, the geometry of the resection surfaces is a function of the patient anatomy, the pathology of the diseased tissue, the technique of the surgeon, and other factors such as the type of tissue removal tools used to prepare the resection. In general, the first resection surface 112 will be formed in such a way that it will serve as a foundation to support the superior facet prosthesis 300 (FIG. 22). The second resection surface 113 or other additional resection surfaces may or may not be present.

FIG. 19 and FIG. 20 also show that a portion of the inferior facet 6 is resected by tissue removal instruments resulting in an inferior resection surface 121. Such resection is preferably effected so that resection is confined to the tissue of the inferior facet 6 and does not extend into the tissue of the posterior arch (or lamina) 35. In FIGS. 19 and 20, the left inferior facet 6 is intact, while a portion of the right inferior facet 6 is resected resulting in the inferior resection surface 121 on the right side. The bone surrounding the inferior resection surface 121 is contoured by tissue removal tools in a shape designed to cradle and support an inferior facet prosthesis 400 (FIG. 23) on the medial side such that when the inferior facet prosthesis 400 is loaded on the lateral side it compresses against and is supported by the inferior resection surface 121.

Alternatively, the inferior facet 6 can be resected, and inferior facet prosthesis 400 sized and shaped, so that inferior facet prosthesis 400 does not engage the inferior resection surface 121.

Figure 21:
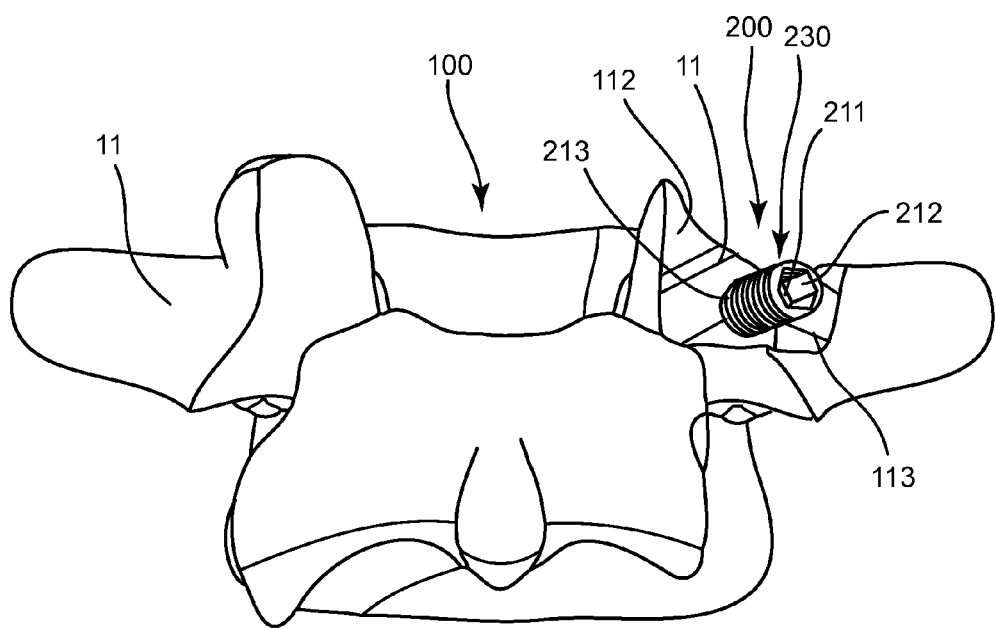
FIG. 21 is a dorsal view of the same resected vertebra shown in FIG. 18 and FIG. 19 with a fixation element placed through the first superior resection surface and into the pedicle bone.
Figure 26:
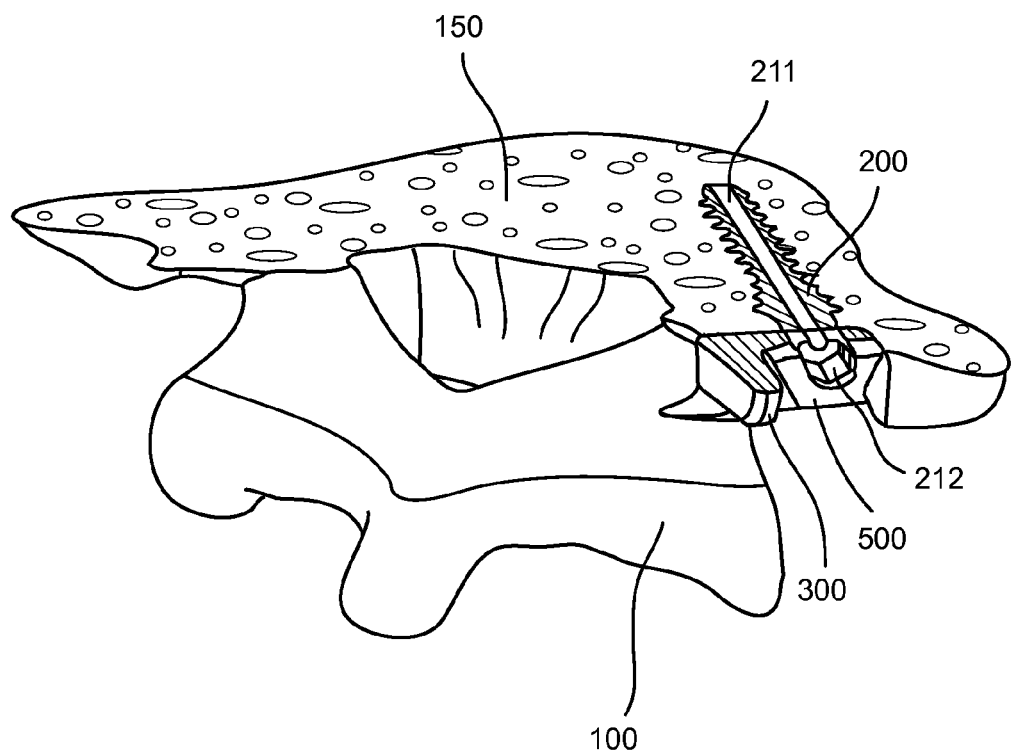
FIG. 26 is a perspective, cross-sectioned view of the same vertebra and implant of FIG. 25 with a cross section aligned with the axis of the fixation element.
Figure 27:
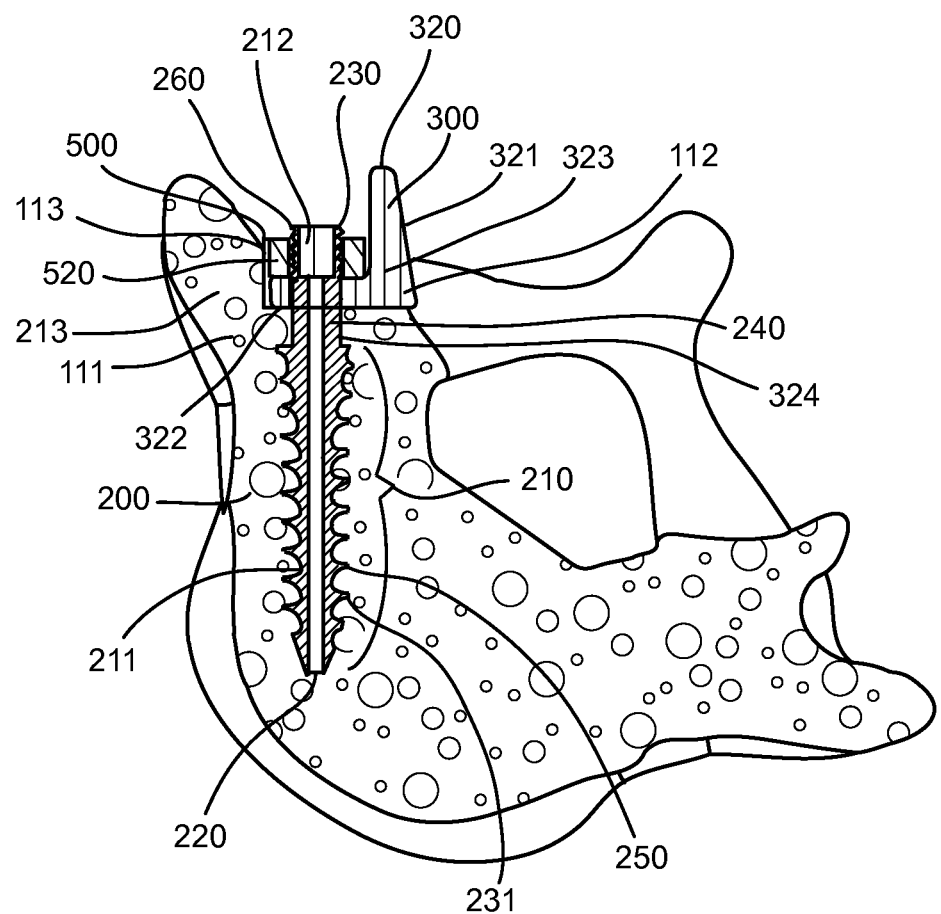
FIG. 27 is a cranial, cross-sectioned view of the vertebra and implant of FIG. 25, with the section plane positioned as in FIG. 26.

FIG. 21 is a dorsal view of the vertebra 100 with a fixation element 200 placed through the superior resection 111 and into the bone of the pedicle 11 to receive the superior facet prosthesis 300 (FIG. 22). The fixation element 200 is aligned and placed into the pedicle 11, similar to how other pedicle screws for posterior stabilization involved with vertebrae fusion are placed in the pedicle 11. In one method, a long guide wire (not shown), with a diameter sized to fit freely into a cannulation 211 (as also shown in FIG. 26 and FIG. 27) in the fixation element 200, is placed through the first resection surface 112 and into the bone of the pedicle 11. The alignment of the long guide wire can be confirmed by x-ray. The fixation element 200 is then guided over the guide wire and driven into the vertebra 100 by a driver (not shown) engaged with a drive feature 212 (FIG. 21) on a proximal post 230 of the fixation element 200. The fixation element 200 is driven into the vertebra 100 until a connection feature 213 (e.g., a screw thread) is just above the first resection surface 112. This connection feature 213 is eventually used to secure the superior facet prosthesis 300 to the vertebra 100.

In a second method for guiding the fixation element 200 into the pedicle 11, a long guide wire (not shown), with a diameter sized to fit freely into a cannulation in a bone preparation instrument (not shown) such as a tap, drill, broach or reamer, is placed through the first resection surface 112 and into the bone of the pedicle 11. The alignment of the long guide wire can be confirmed by x-ray. The bone preparation instrument is then guided over the guide wire and driven into the bone of the pedicle 11 to prepare a cavity for the fixation element 200. The guide wire and bone preparation instrument are then removed and the fixation element 200 is guided into the prepared cavity in the pedicle 11 by a driver (not shown) engaged with the drive feature 212 on the proximal post 230 of the fixation element 200. Like in the first method, the fixation element 200 is driven into the vertebra until a connection feature 213 (e.g., a screw thread) is just above the first resection surface 112. This connection feature 213 is eventually used to secure the superior facet prosthesis 300 to the vertebra 100.

In yet a third method of placing the fixation element 200 in the pedicle, the surgeon aligns the fixation element 200 with anatomic landmarks and simply drives the fixation element 200 through the first resected surface 112 and into the pedicle 11. As with the first and second methods, the fixation element 200 is driven into the vertebra 100 until a connection feature 213 (e.g., a screw thread) is just above the first superior resection surface 112.

In FIG. 22, a dorsal view illustrates a superior facet prosthesis 300 placed around the fixation element 200. The superior facet prosthesis 300 has a facet articulating component 320 that articulates against the inferior facet articulating surface of the vertebra above it. The facet articulating component 320 is preferably formed in the general shape of a blade or wing ear. The superior facet prosthesis 300 also has a bone apposition surface 322 that has been placed on the first resection surface 112 and an opening 324 in a flange 323 that surrounds the fixation element 200. The superior facet articulating component 320 has an articulating surface 321 generally adjacent to the flange 323 that is oriented in a direction that faces approximately the same direction that the original anatomic superior articulating surface 145 faced prior to resection.

This orientation of the articulating surface 321 allows the superior facet prosthesis 300 to function as either a hemiarthroplasty implant and articulate against a natural anatomic inferior facet 6 or act as a portion of a unilateral prosthesis and articulate against an inferior facet prosthesis 400 on the vertebra superior (cephalad) to it. No portion of superior facet prosthesis 300 rests on the lamina of the vertebra 100. In this application, a "unilateral prosthesis" is a prosthesis in which both facets of only one of the facet joints between adjacent vertebrae are replaced by prostheses. A "hemiarthroplasty" is a type of arthroplasty in which one side of an articulating joint surface is replaced with an artificial implant.

Figure 23:
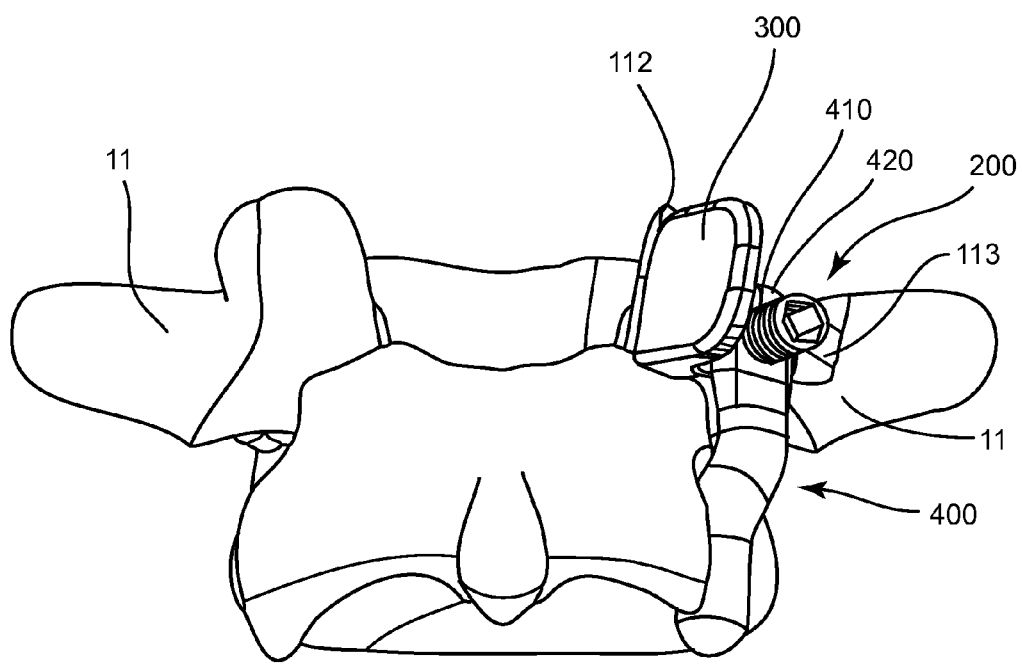
FIG. 23 is a dorsal view of the vertebra and the implant of FIG. 23 and also showing the addition of an inferior facet prosthesis.

FIG. 23 is a dorsal view showing the addition of the inferior facet prosthesis 400 to the construct described in FIG. 22. The inferior facet prosthesis 400 generally has a shape similar to a longitudinal rod that is curved to match the contour of the inferior resection 121 (FIGS. 19 and 20). The inferior facet prosthesis 400 has an opening 410 through its superior end 420 that is shaped to surround the portion of the fixation element 200 that protrudes from the first resection surface 112. In FIG. 23, the inferior facet prosthesis 400 is placed over the superior facet prosthesis 300. However, the order of the placement of the prostheses 300, 400 can be reversed such that the inferior prosthesis 400 is placed on the fixation element 200 first, followed by the superior prosthesis 300. When only the inferior facet 6 or the superior facet 43 is being replaced, only the appropriate (superior or inferior) facet prosthesis 300 or 400 is placed on the fixation element 200 without the other (inferior or superior) facet prosthesis 300 or 400.

Because the various components of the implant are modular, many combinations of configurations and implant size, structure and shapes are feasible. For example, in a patient with unusual anatomy, the inferior facet prosthesis 400 may need to be larger than expected to conform to a particularly unusual or exceptionally large morphology of the inferior resection surface 121, and the superior facet prosthesis 300 may need to have an unusual angle to its articulating surface 321 to conform to particular anatomic constraints. If this is the case, the modularity of the system allows for the surgeon to assemble an implant specifically designed to match the patient's anatomic structures during the surgery. This flexibility of a modular implant design allows the implant manufacturer to accommodate a large variation in anatomic structures with a limited selection of implant component sizes, shapes, and material types.

The modularity of the implant design also allows different components of the implant to be fabricated from different materials. Traditionally, bone fixation implants such as the fixation element 200 are fabricated from biocompatible metals or alloys that provide sufficient strength and fatigue properties, such as cobalt chrome alloys, titanium and titanium alloys, and stainless steels. However, the fixation element 200 may be fabricated from ceramics, polymers, or biological materials such as allograft bone, composites, or other biocompatible structural materials. Likewise the superior facet prosthesis 300 and the inferior facet prosthesis 400 may be fabricated from metals, alloys, ceramics, polymers, biological materials, composites, or other biocompatible structural materials.

Figure 24:
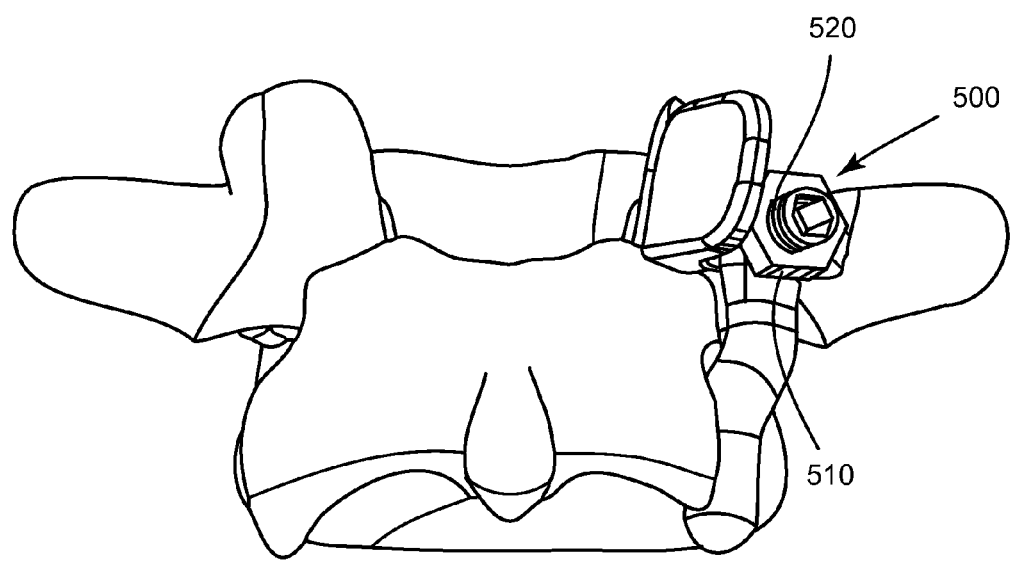
FIG. 24 is a dorsal view of the implant and vertebra of FIG. 23 and also showing the addition of an enlarged head that has the shape of a locking nut.

In FIG. 24, a dorsal view illustrates the addition of an enlarged head 500 to the fixation element 200. The enlarged head 500 is tightened down to force the prostheses 300, 400 against the bone to stabilize them. The enlarged head 500 shown in FIG. 24 has a hexagonal geometry on its external surface that is shaped to accept a driver (not shown) that is used to force an internal connection feature 520 (e.g., a screw thread) of the enlarged head 500 onto the connection feature 213 of the fixation element 200. In the case of the threaded embodiment of the connection feature 213, the enlarged head 500 is provided with a threaded connection feature 520 and is driven onto the fixation element 200 by turning the enlarged head 500 and allowing the threads to drive all components of the implant between the enlarged head 500 and the first resection surface 112 against the bone at or near the resection surface 112.

Figure 25:
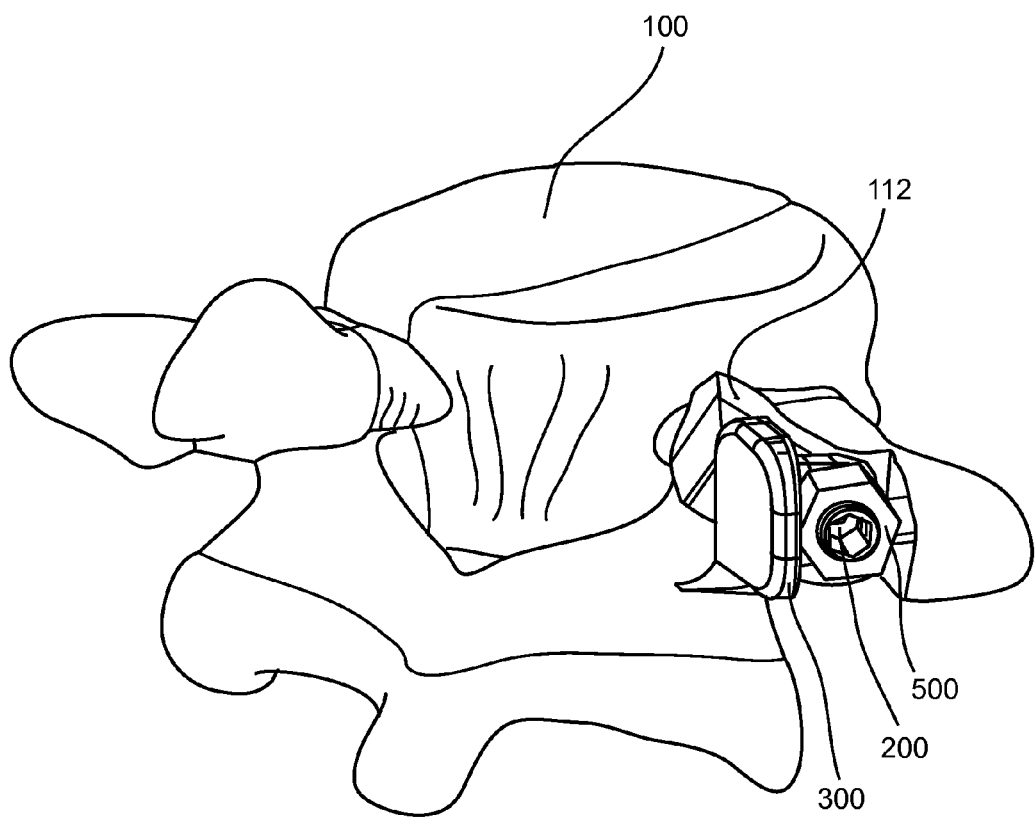
FIG. 25 is a perspective view of a vertebra with an assembled implant comprising a fixation element, superior facet prosthesis, and a locking nut.

FIG. 25 is a perspective posterior view of the assembly of the fixation element 200, the superior facet prosthesis 300, and the enlarged head 500. The enlarged head 500 has been placed on the first resection surface 112.

FIG. 26 is a perspective, cross-sectioned view of the same construct shown in FIG. 25. The superior facet prosthesis 300, the enlarged head 500, the fixation element 200, and the vertebra 100 have been cut by a cross-sectioning plane 150 placed along an axis that passes through the center of the fixation element 200. The cross-section plane 150 is shown for visualization purposes to illustrate, using a cross-sectioned view, how the vertebra 100, fixation element 200, superior facet prosthesis 300 and the enlarged head 500 engage each other. In actual surgery, it is highly unlikely that a surgeon would make a cut as illustrated by the cross-section 150 shown in FIG. 26.

FIG. 27 is a cranial, section view of the vertebra 100 and the implant, wherein the cross-section plane 150 is oriented to face the viewer. In FIG. 27, the fixation element 200 is in the vertebra 100. The embodiment of the fixation element 200 in FIG. 27 comprises a distal end 220 that is shaped to guide the fixation element 200 into bone tissue, a bone stabilizing portion 210 adjacent to the distal end, a shaft portion 240 adjacent to the bone stabilizing portion 210, a connection feature 213 adjacent to the shaft portion 240, and a drive feature 212.

The distal end 220 shown in FIG. 27 has a frusto-conical shape that allows the fixation element 200 to be driven or guided into the vertebra 100. The distal end 220 could be shaped in the form of a spade tip, trochar tip, or twist drill tip to assist in the guidance of the fixation element 200 in the vertebra 100. The fixation element 200 may also have a cutting flute (not shown) formed in the distal end 220 to help remove bone tissue and accommodate the guidance of the fixation element 200 in the vertebra 100. The bone stabilizing portion 210 helps to secure the fixation element 200 to the vertebra 100. The bone stabilizing portion 210 can include various features designed to anchor into bone such as threads, ribs, grooves, slots, fins, barbs, splines, bone ingrowth surfaces, roughened surfaces, or any geometric feature that helps to engage the fixation element 200 with the bone tissue to help stabilize the fixation element 200. In FIG. 27, the bone stabilizing portion 210 has a unitary continuous bone thread 231. However, other types of threads such as multiple lead threads, variable pitched thread, non-uniform pitch thread, buttress thread, or other thread forms used on bone screws may be used. Because FIG. 27 is a cross-sectional view, the full length of the cannulation 211 is seen passing from the distal end 220 of the fixation element 200 to the proximal post 230 of the fixation element 200.

The drive feature 212 in the embodiment shown in FIG. 27 is an internal hex. However, any shape of drive feature 212 that transmits the loads necessary to drive the fixation element 200 into the vertebra 100 can be formed on the proximal post 230 of the fixation element 200. The depth of the drive feature 212 formed in the proximal post 230 of the fixation element 200 is seen in the cross-sectional view of FIG. 27. The drive feature 212 may be an internal drive feature such as the hex socket shown in this embodiment, or an external drive feature with geometry on the periphery of the proximal post 230 of the fixation element 200 that engages with a corresponding internal drive feature on a driver tool (not shown). In this embodiment the depth of the drive feature 212 is slightly longer than its cross-section is wide. This depth can be adjusted based on the material properties of the fixation element 200 and the drive tool (not shown).

The fixation element 200 is fabricated from biocompatible base materials that provide the necessary structural rigidity and strength. Examples of base materials that may be used in the construction of the fixation element 200 include titanium, titanium alloys, cobalt-chrome alloys, stainless steel alloys, zirconium alloys, other biocompatible metal materials, biocompatible ceramics, biocompatible composites, and biocompatible polymers. The fixation element 200 may also have surface materials formed on the base material that provide material properties specific to a particular portion of the fixation element 200. For example, the bone stabilization portion 210 could be coated with materials that allow for improved bone ingrowth into the implant surface such as a hydroxylapatite, bioceramic, Bioglass®, or other calcium phosphate derived material. The tribological bearing properties of the material in the areas that the fixation element 200 interfaces with other artificial elements may be improved by applying surface hardening techniques to the material of the fixation element 200 in these areas. Surface hardening techniques known in the materials science and materials engineering arts such as anodizing, ion implantation, and other techniques could be applied to these isolated areas.

As mentioned previously, the connection feature 213 is formed on the portion of the fixation element 200 that protrudes from the first resection surface 112. This connection feature 213 is designed to connect the enlarged head 500 to the fixation element 200. In the embodiment of the connection feature 213 shown in FIG. 21, threads 260 are on the external surface of this proximal section of the fixation element 200. These threads 260 engage with the threads of the internal connection feature 520 (FIG. 27) of the enlarged head 500. Although the connection feature 213 in this embodiment is threaded, other mechanical locking features (not shown) capable of locking the fixation element 200 and the enlarged head 500 together, such as press fit, taper fit, bonding fit by cement or glue, interference fit, expansion fit and mechanical interlocking fit such as a bayonet connection, can be used as the connection feature 213. A corresponding construction may then be used as connection feature 520 of the enlarged head 500.

Also shown in FIG. 27 is a cross-sectional view of the superior facet prosthesis 300. This embodiment of the superior facet prosthesis 300 has a flange 323 that has an opening 324 that receives the fixation element 200. In the assembled and implanted configuration of this embodiment, the flange 323 is positioned such that its bone apposition surface 322 makes contact with the first resection surface 112. Although not shown in this embodiment, other embodiments of the superior facet prosthesis 300 have structures (e.g., spikes) that protrude into the first resection surface 112 to help resist torsion and other anatomic loads. Protruding from the flange 323 at a given angle α, and a given distance X from the opening 324, is the articulating component 320. The articulating surface 321 of the facet articulating component 320 replicates the natural articular surface of the replaced facet. Once the surgeon assesses the anatomy of the superior facet 43 that is being replaced, a particular superior facet prosthesis 300 is selected that has the angle α and the distance X that best fits the anatomy of the level of vertebra, the left or right side, and the size of the patient's anatomy being replaced. Thus a kit containing various sizes and shapes of superior facet prostheses 300 is provided to the surgeon and the surgeon selects the superior facet prosthesis 300 that best suits the situation.

After the fixation element 200 and the superior facet prosthesis 300 are selected and placed, they are locked to the vertebra 100 by the enlarged head 500. As shown in FIG. 24, the enlarged head 500 in this embodiment has an internal connection feature 520 and a hexagonal shaped external drive feature 510 that is used to drive the enlarged head 500 over the fixation element 200 and against the superior facet prosthesis 300. The specific shape of the external drive feature 510 is dependent on the mating shape of the driver (not shown).

Figure 28:
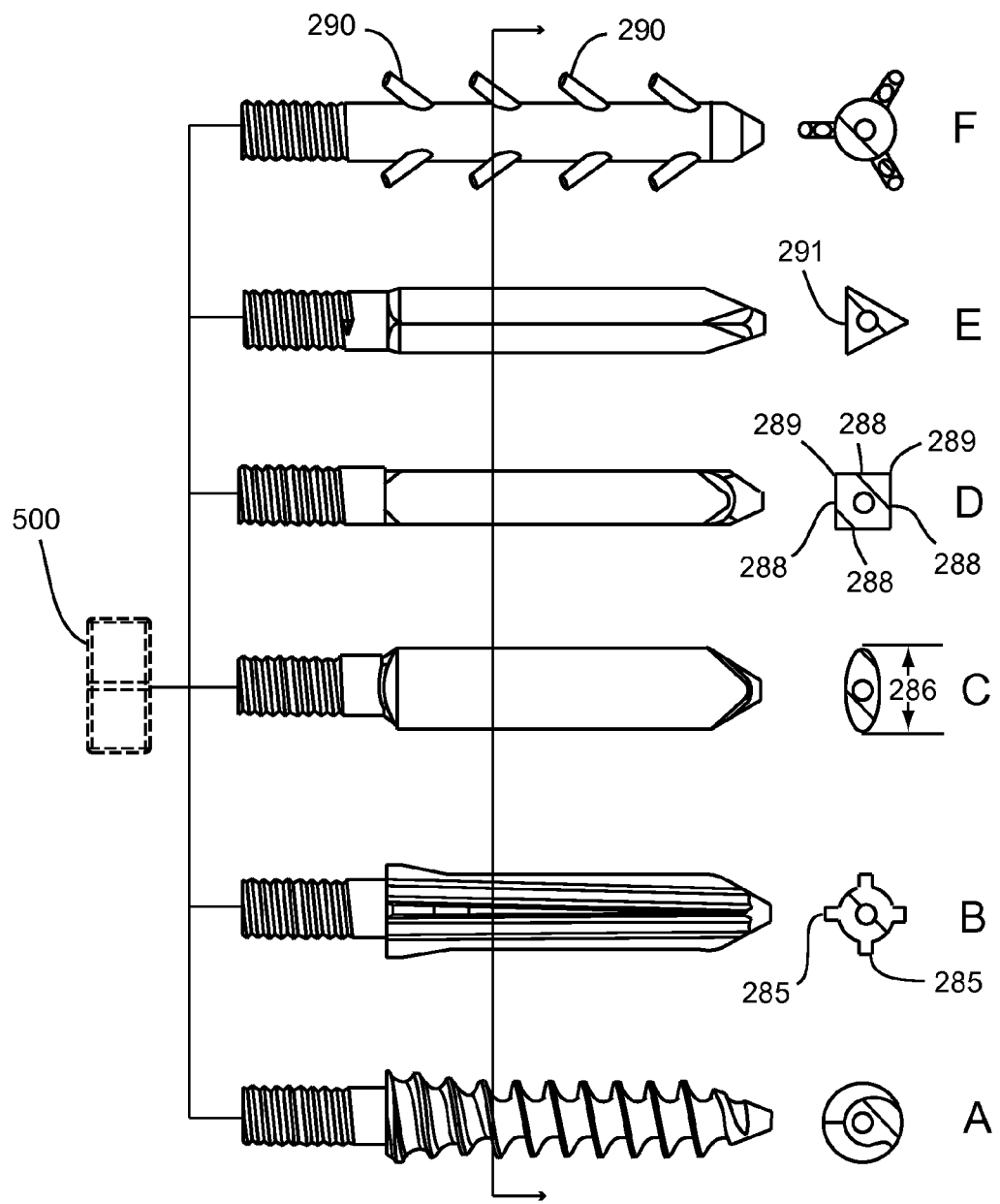
FIG. 28 is a side view of embodiments A, B, C, D, E, and F of the fixation element, a cross-sectional view of each of embodiments A, B, C, D, E, and F, and a side view of the enlarged head in the shape of a locking nut.

Referring to FIG. 28, side and cross-sectional views illustrate six different embodiments of fixation elements, which are labeled A, B, C, D, E, and F. The figure shows a side view of each fixation element embodiment and a cross-sectional view of each embodiment to the right of the respective side view. To the left of the six embodiments is a representative enlarged head 500. Embodiment A is the threaded fixation element 200 embodiment shown in FIGS. 26 and 27 and described above. Embodiments B through E are various designs of fixation elements with non-circular cross-sections. Embodiment B is a four rib cruciate design with four longitudinal fins 285 configured to resist torsion when the fixation element 200 is in the vertebra 100. Embodiment C is an oval shaped cross-section design that is wider in the first direction 286 than the second direction 287 to resist torsion. If the width in the first direction 286 is equal to the width in the second direction 287, the cross-section shape becomes more of a circle and bone stabilization portion 210 becomes more of a press-fit peg. Embodiment D is a square cross-section design with four approximately perpendicular sides 288. The corners 289 of the sides 288 help to resist torsion. Embodiment E is a triangular cross-section design with three sides 291 to resist torsion. Embodiment F is an anchor-like design that is driven into the vertebra, with the wire arches or barbs 290 being compressed against the host bone and applying a radial expansion force so as to lock the structure to the bone.

Figure 28A:
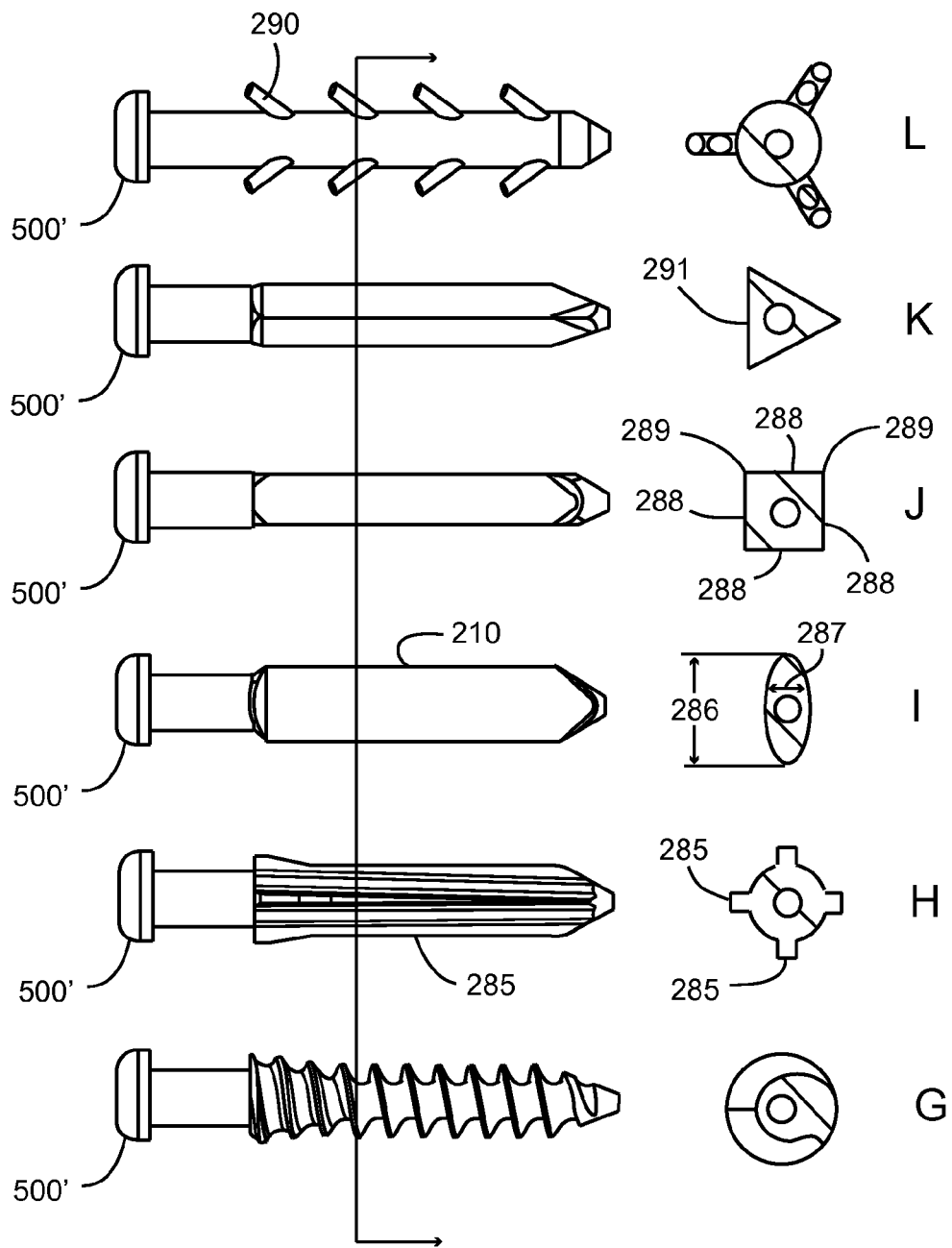
FIG. 28A is a side view of embodiments G, H, I, J, K, and L of the fixation element with attached enlarged heads, and a cross-sectional view of each of embodiments G, H, I, J, K, and L.

Referring to FIG. 28A, side and cross-sectional views illustrate six more different embodiments of fixation elements, which are labeled G, H, I, J, K, and L. FIG. 28A shows a side view of each fixation element embodiment and a cross-sectional view of each embodiment to the right of the respective side view. Each embodiment has an attached or integrally formed enlarged head 500'. Embodiment G is similar to the threaded fixation element 200 embodiment shown in FIGS. 10, 11, 12 and 24 and described above. Embodiments H through K are various designs of fixation elements with non-circular cross-sections. Embodiment H is a four rib cruciate design with four longitudinal fins 285 configured to resist torsion when the fixation element is in the vertebra 100. Embodiment I is an oval shaped cross-section design that is wider in a first direction 286 than in a second direction 287 to resist torsion. If the width in the first direction 286 is equal to the width in the second direction 287, the cross-section shape becomes more of a circle and the bone stabilization portion 210 becomes more of a press-fit peg. Embodiment J is a square cross-section design with four approximately perpendicular sides 288. The corners 289 of the sides 288 help to resist torsion. Embodiment K is a triangular cross-section design with three sides 291 to resist torsion.

Embodiment L is an anchor-like design that is similar to Embodiment F in FIG. 28, but with an attached or integrally formed enlarged head 500'. As embodiment L is driven into the vertebra, wire arches or barbs 290 are compressed and apply radial expansion force against the wall of the prepared bone and into the pedicle 11, resulting in a locking anchor.

Figure 29:
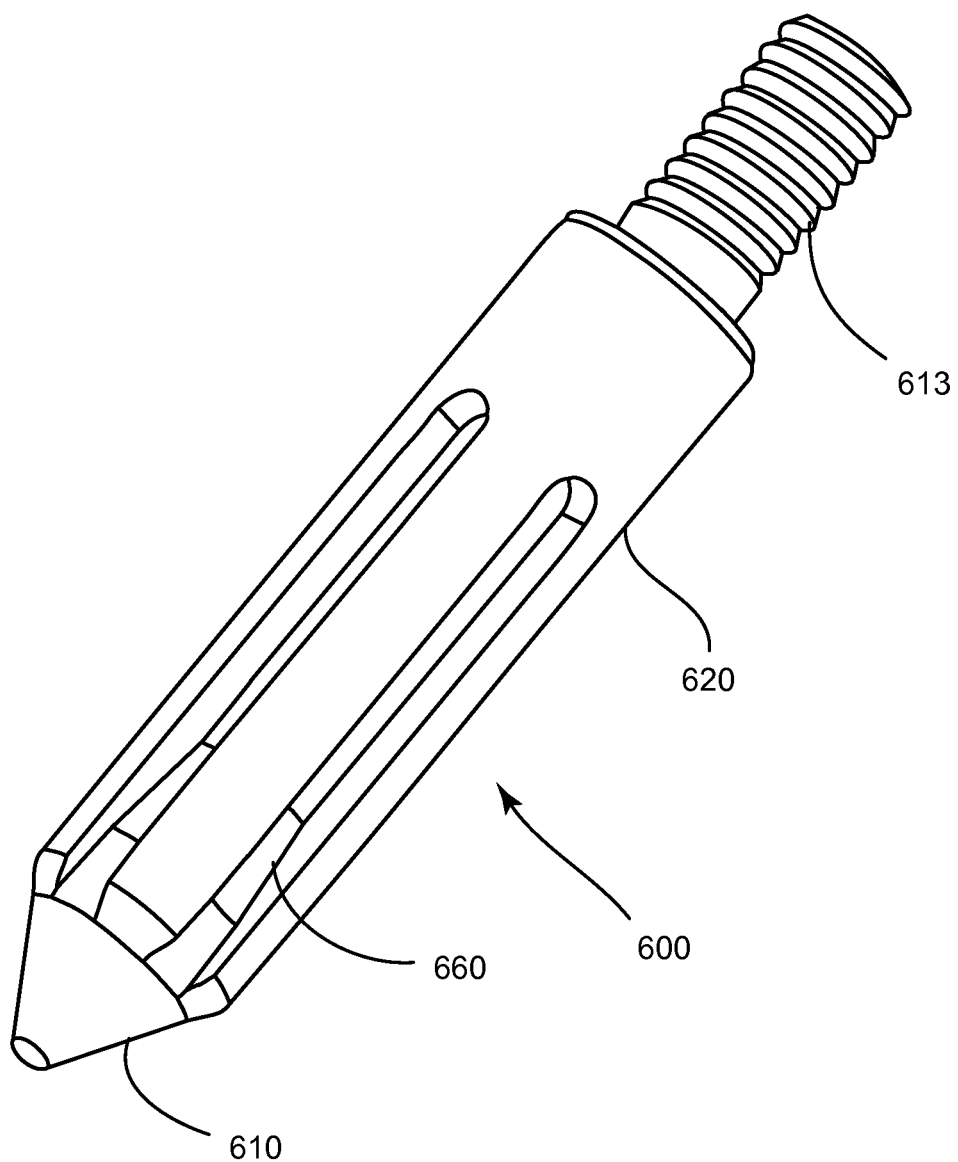
FIG. 29 is a perspective view of a radially expanding fixation element in its unexpanded state.

FIG. 29 is a perspective view of a radially expanding fixation element 600. The radially expanding fixation element 600 comprises two main elements, an expansion sleeve 620 and a central element 610 that is inside of the expansion sleeve 620. The radially expanding fixation element 600 is placed into the vertebra 100 and then the central element 610 is drawn outward relative to the expansion sleeve 620 resulting in radial expansion of the fixation element 600. This is shown in FIG. 30.

Figure 30:
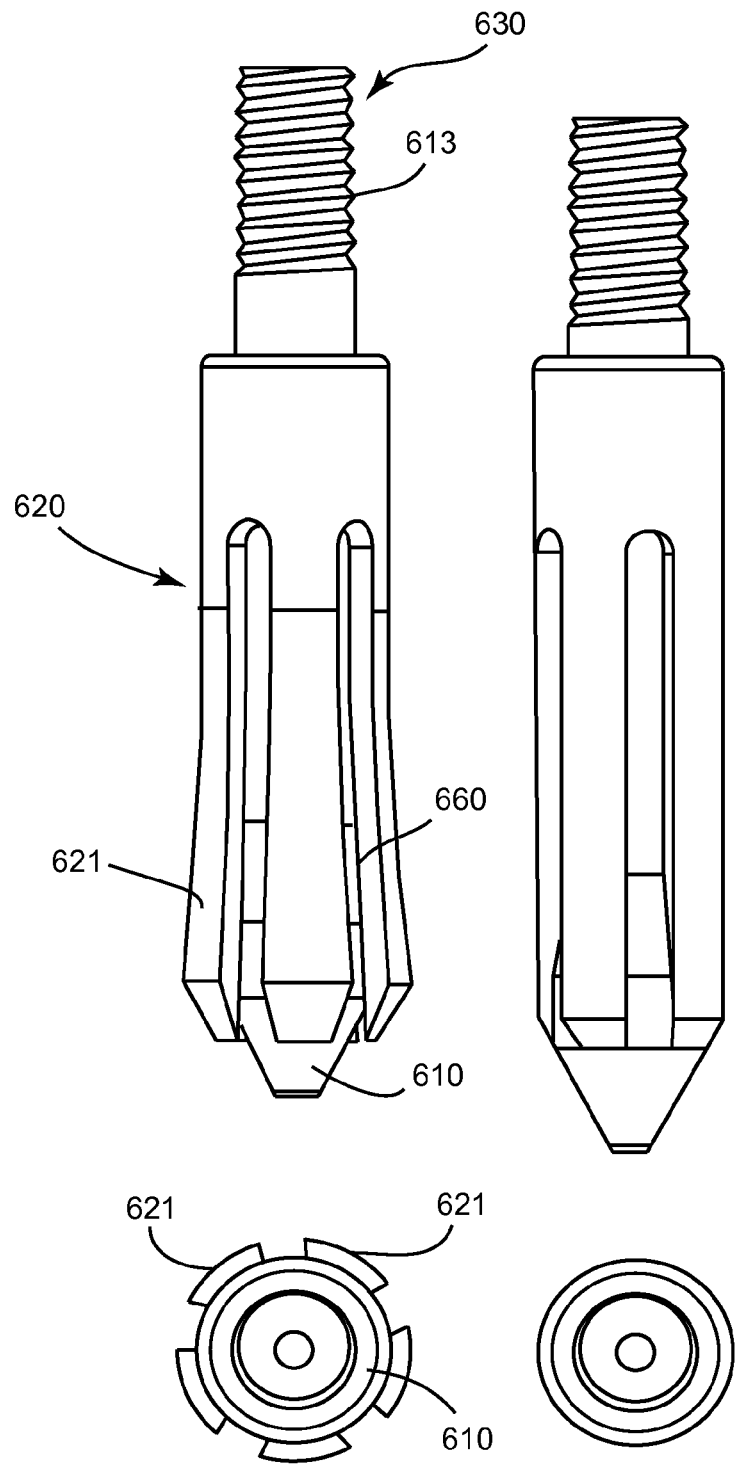
FIG. 30 is a side view and a bottom view of (i) an expanded radially expanding fixation element and (ii) an unexpanded radially expanding fixation element.

Referring to FIG. 30, side and bottom views illustrate the fixation element 600 of FIG. 29. As a proximal post 630 of the central element 610 is pulled axially along its longitudinal axis, and the expansion sleeve is held axially in the bone by compression fit, talons 621 on the expansion sleeve 620 are radially expanded outward by a mandrel 660 on the central element 610. The talons or fingers 621 provide both torsional and axial stability to the radially expanding fixation element 600. This provides a secure fixation element for fixation of the remaining implant components. Furthermore, expansion of the fixation element 600 may cause the fixation element 600 to center itself within the pedicle 11.

Figure 31:
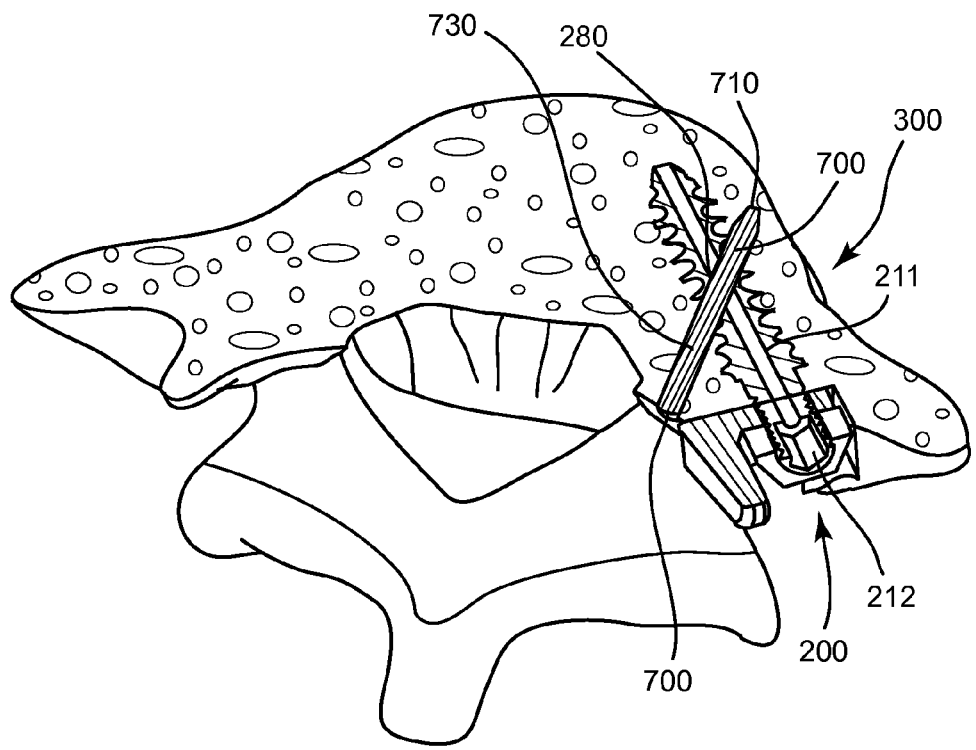
FIG. 31 is a perspective cross-sectional view of a vertebra and a facet implant showing a cross-pin torsionally and axially securing the fixation element.

FIG. 31 is a perspective, cross-sectional view of a cross-pin element 700 engaged with the fixation element 200 to help secure the fixation element 200 both torsionally and axially. The cross-pin element 700 is columnar in shape having a distal end 710, a midsection 730 (with a length along its longitudinal axis that is longer than its transverse cross-sectional width), and a proximal post 720. The distal end 710 is shaped to penetrate through bone tissue and into a cross hole 280 formed in the fixation element 200. Instrumentation (not shown) is used to align the cross-pin element 700 with the cross-hole 280 via fixation of the instrumentation to the drive feature 212 or the cannulation 211 on the fixation element 200 and alignment of the direction of insertion of the cross-pin element 700 with the cross-hole 280. Once the cross-pin element 700 is in place in the bone and through the fixation element 200, the torsional and axial stability of the fixation element 200 is improved.

The various embodiments of the fixation element 200 described above and shown in FIG. 28 through FIG. 31 function in conjunction with the enlarged head 500 to hold the inferior facet prosthesis 400 and/or the superior facet prosthesis 300 to their respective resection surfaces 112, 113, and/or 121. Various combinations of this modular implant will be described below and shown in FIGS. 32 through 37. Although these figures illustrate the use of the fixation element 200 and the enlarged head 500 as the mechanism for securing the prostheses 300, 400 to the vertebra 100, other clamping devices such as the screw fastener 17 (FIG. 10) may be used to mount the prostheses 300, 400 to the bone. For example, the screw prostheses 17 shown in FIGS. 10 through 12 may pass through either the opening 324 (FIG. 22) in the superior facet prosthesis 300 or the opening 410 (FIG. 23) in the inferior facet prosthesis 400 or through both of these openings 324, 410. The head of the screw fastener 17 acts as the securing mechanism by pressing the inferior facet prosthesis 400 and the superior facet prosthesis 300 against their respective resection surfaces 112, 113, and/or 121.

FIGS. 32 through 37 demonstrate different combinations of assemblies of facet replacement prostheses. The basic components of the prosthesis are the fixation element 200, the superior facet prosthesis 300, the inferior facet prosthesis 400, and the enlarged head 500. However, as described above, a screw fastener 17 can replace the fixation element 200 and the enlarged head 500.

Figure 32:
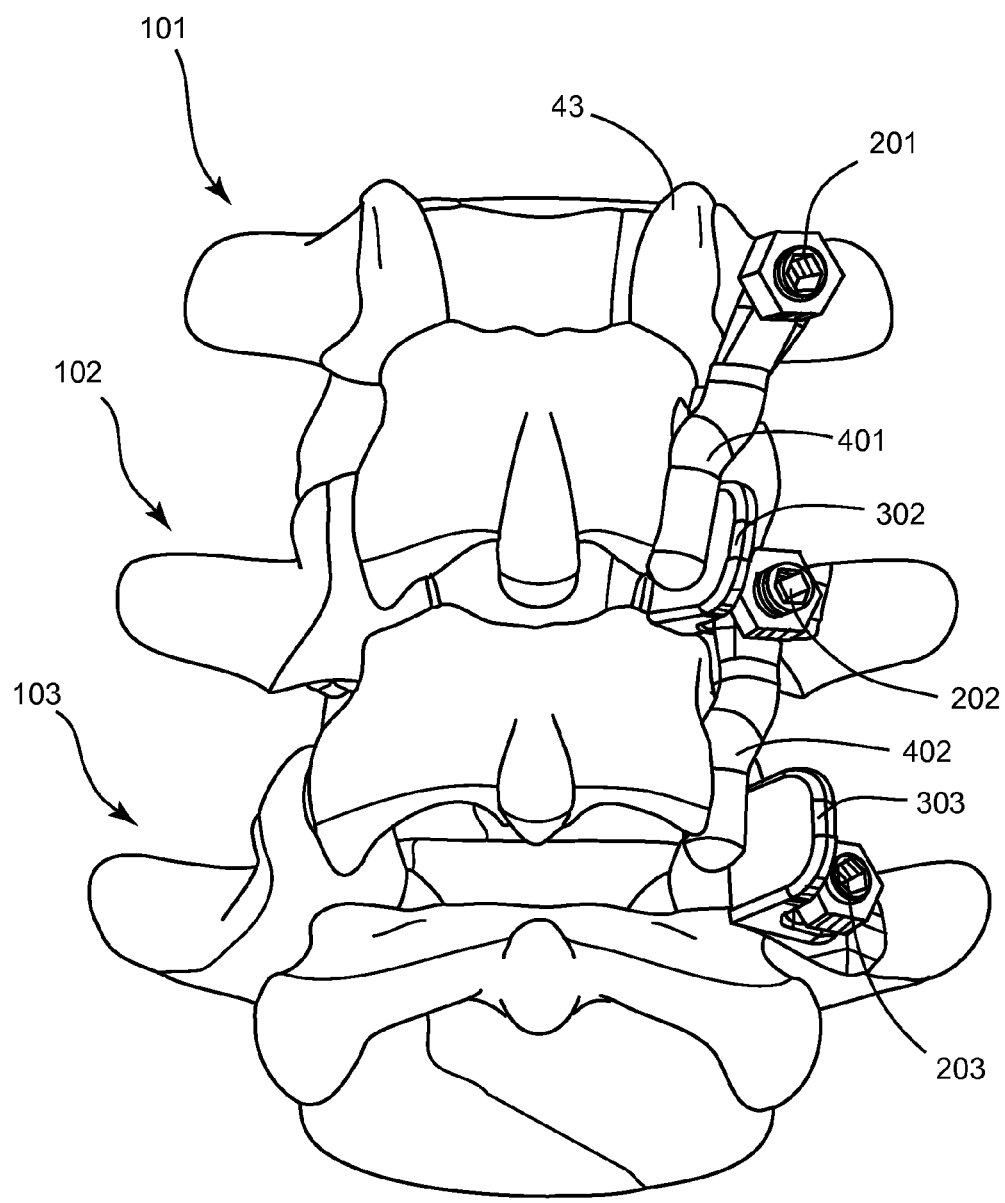
FIG. 32 is a dorsal view of a spinal section showing a top, middle, and bottom vertebra with unilateral facet replacements on the right side of the spine section, both between the top and middle vertebra, and between the middle and bottom vertebra.

Referring to FIG. 32, a dorsal view illustrates three sequential layers of vertebrae. A top vertebra 101 is above a middle vertebra 102, and the middle vertebra 102 is above a bottom vertebra 103. Portions of some of the facets on the right side of the vertebrae are replaced by prostheses. With regard to the facet joint between the top vertebra 101 and the middle vertebra 102, an inferior facet prosthesis 401 is articulating against a superior facet prosthesis 302 to form an artificial unilateral joint. The inferior facet of the middle vertebra 102 is replaced by an inferior facet prosthesis 402 and the superior facet of the bottom vertebra 103 is replaced by superior facet prosthesis 303. Thus, a second unilateral prosthetic joint is formed that is also on the right side and is located at the level between the middle vertebra 102 and the bottom vertebra 103. FIG. 32 demonstrates the difference in shape of the inferior facet prosthesis 401 that is implanted around the fixation element 201 without a superior facet prosthesis 300 and an inferior facet prosthesis 402 that is implanted around a fixation element 202 and over a superior facet prosthesis 302. The opening 410 (not visible) of the inferior facet prosthesis 401 on the top vertebra 101 in this assembly is offset more laterally than the opening 410 (not visible) in the inferior facet prosthesis 402 for the middle vertebra 102. This is because the fixation element 201 is implanted more laterally on the top vertebra 101 to preserve more of the superior facet since it is not replaced by a prosthesis at this level.

Figure 33:
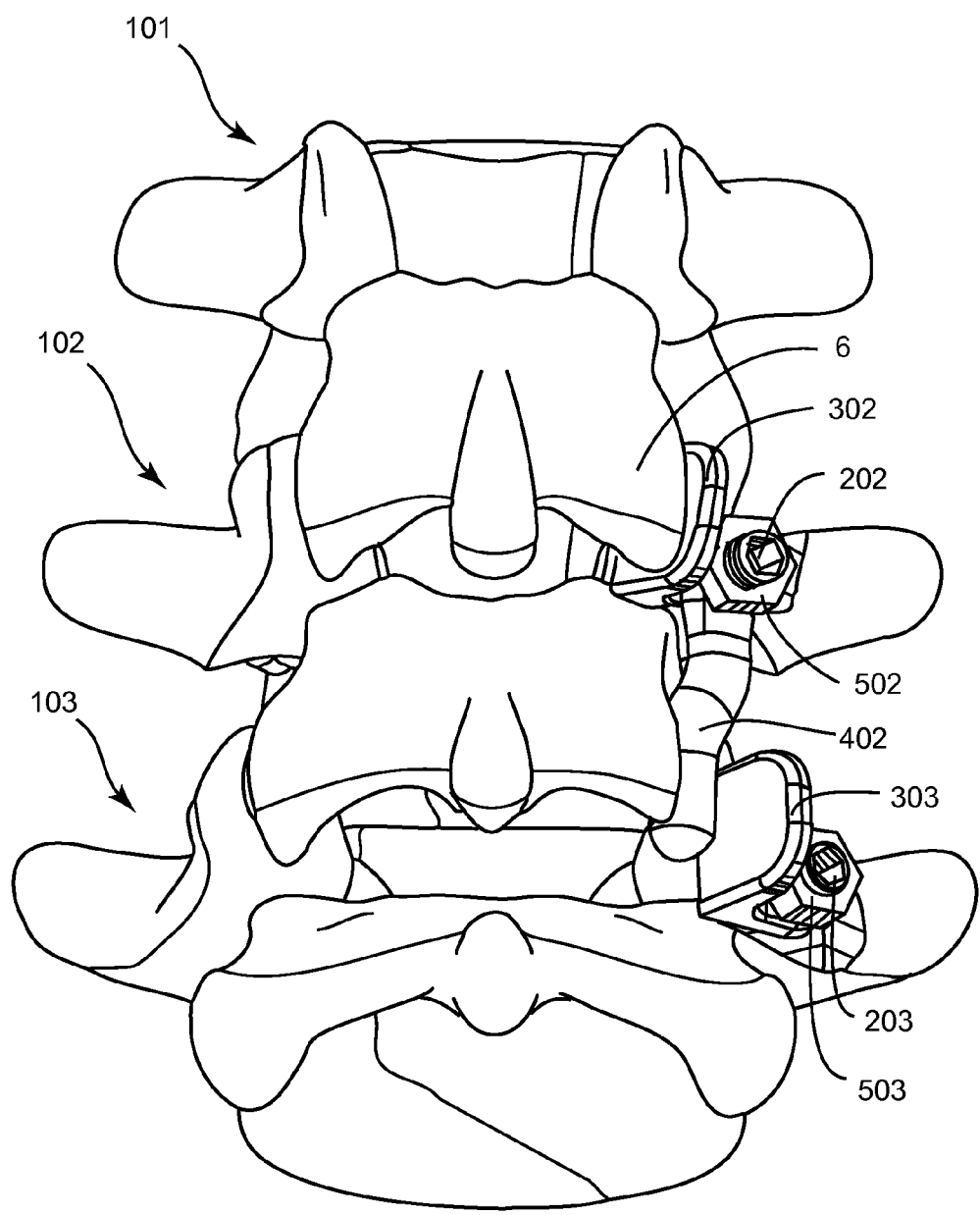
FIG. 33 is a dorsal view of a spine section showing a superior hemiarthroplasty facet replacement between the top and the middle vertebra and unilateral replacement between the middle and the bottom vertebra.

Referring to FIG. 33, a dorsal view illustrates the top vertebra 101 in intact form, without resection of the facets. Portions of both the superior and inferior facets on the right side of the middle vertebra 102 are replaced by a superior facet prosthesis 302 and an inferior facet prosthesis 402. Only the right superior facet of the bottom vertebra 103 is replaced (i.e., by a superior facet prosthesis 303) in FIG. 33. Thus, a hemiarthroplasty replacement has been performed on the right facet joint between the top vertebra 101 and the middle vertebra 102 and a unilateral replacement has been performed between the middle vertebra 102 and the bottom vertebra 103. The assembly shown in FIG. 33 demonstrates how the superior facet prosthesis 302 can articulate against the natural inferior facet 6 and the superior facet prosthesis 303 can articulate against the inferior facet prosthesis 402.

Figure 34:
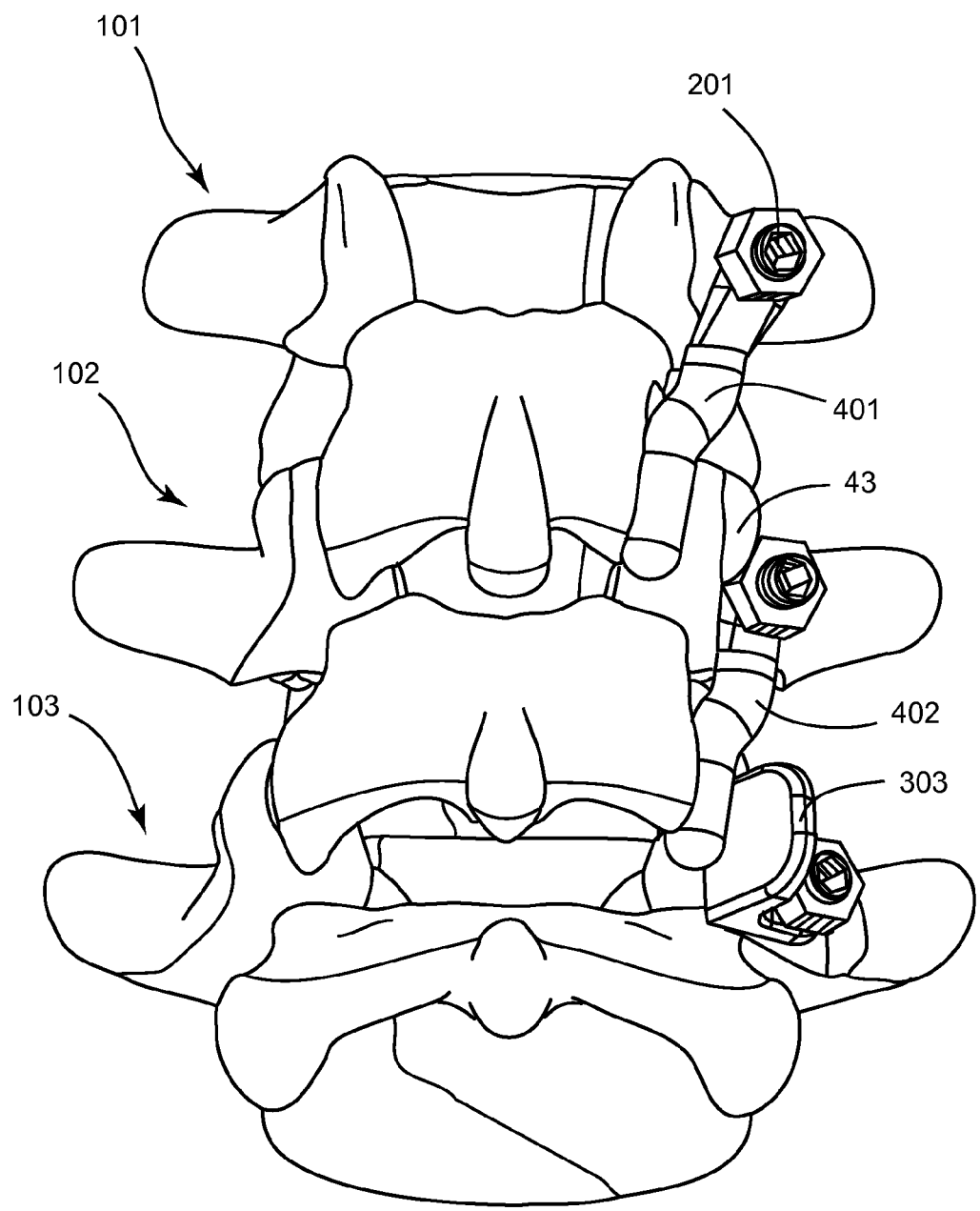
FIG. 34 is a dorsal view of a spinal section showing an inferior facet hemiarthroplasty replacement between the top and the middle vertebra and a unilateral replacement on the right side between the middle and the bottom vertebra.

FIG. 34 is a dorsal view illustrating how the inferior facet prosthesis 401 can articulate against the natural superior facet 43, or the inferior facet prosthesis 402 can articulate against the superior facet prosthesis 303. The right facet joint between the top vertebra 101 and the middle vertebra 102 is a hemiarthroplasty replacement with the inferior facet replaced by the inferior facet prosthesis 401. The right facet joint between the middle vertebra 102 and the bottom vertebra 103 is a unilateral replacement with the inferior facet replaced by the inferior facet prosthesis 402 and the superior facet of the bottom vertebra 103 replaced by the superior facet prosthesis 303.

Figure 35:
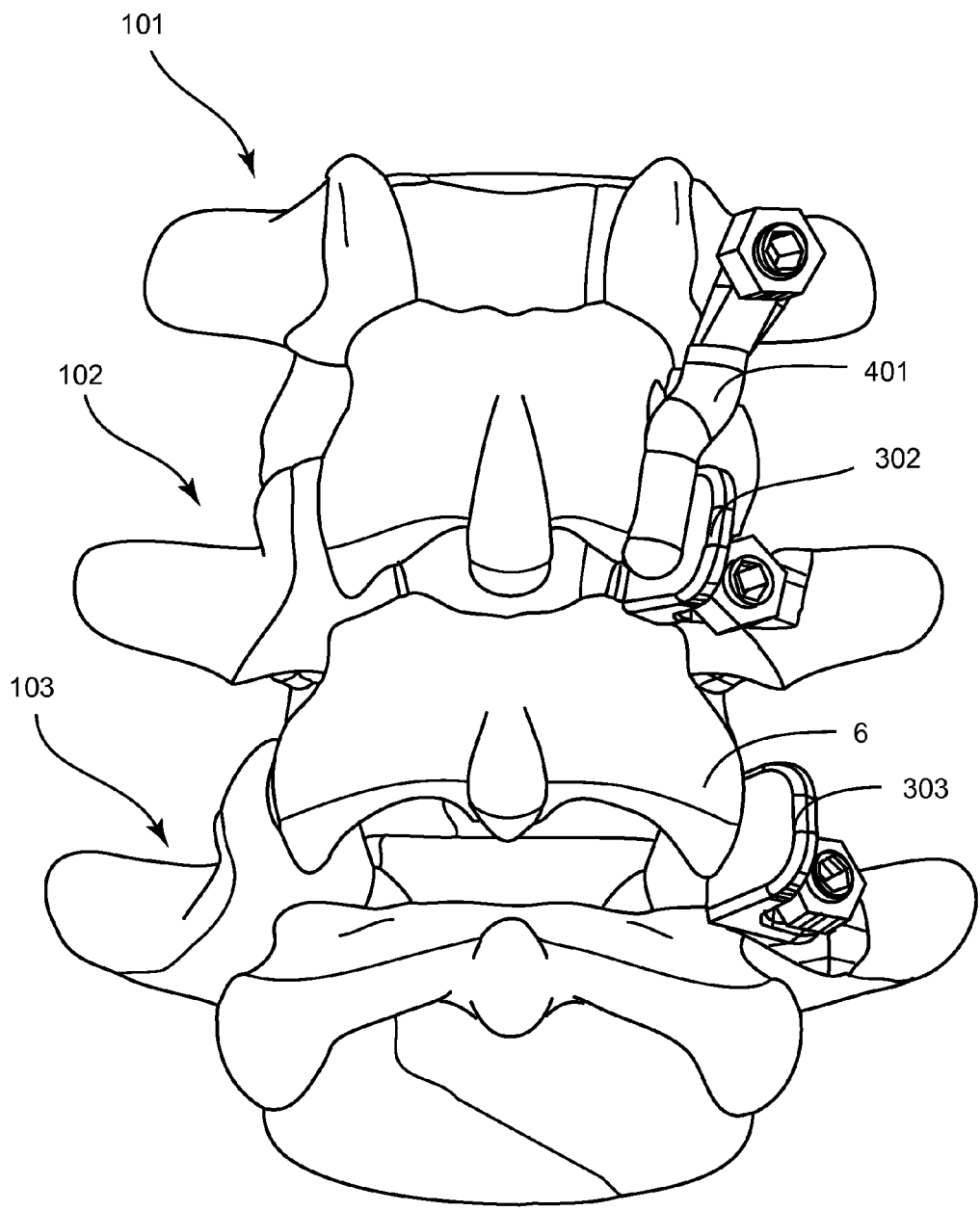
FIG. 35 is a dorsal view of a spinal section showing a unilateral replacement between the top and middle vertebrae on the right side, and an inferior facet hemiarthroplasty replacement between the middle and bottom vertebrae on the same side.

Referring to FIG. 35, a dorsal view shows another example of how the superior facet prosthesis 303 can articulate against the natural inferior facet 6 or the superior facet prosthesis 302 can articulate against the inferior facet prosthesis 401. In this assembly of the implant, the right side between the top vertebra 101 and the middle vertebra 102 is a unilateral replacement and the right side between the middle vertebra 102 and the bottom vertebra 103 is a hemiarthroplasty replacement.

Figure 36:
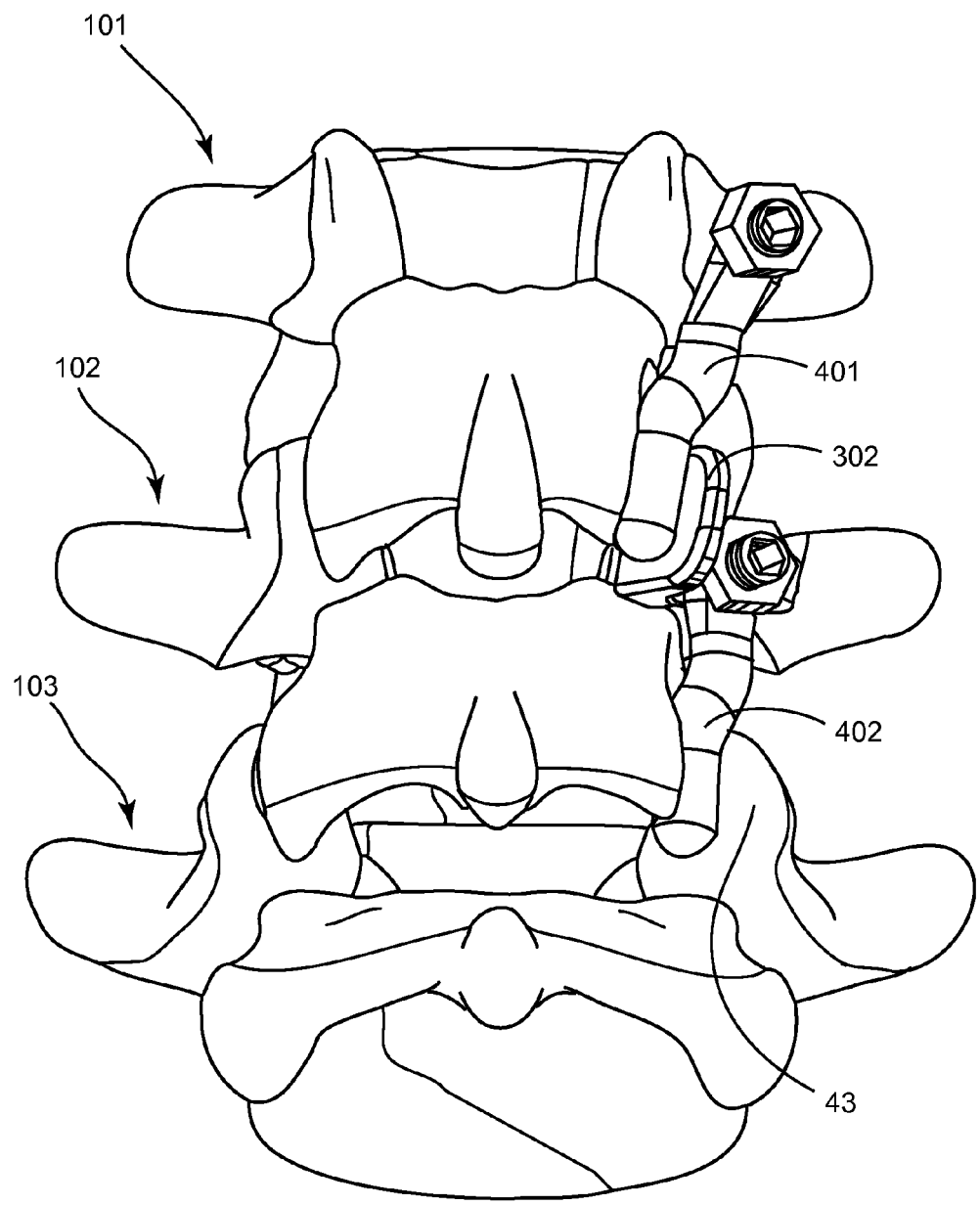
FIG. 36 is a dorsal view of a spinal section showing a unilateral replacement between the top and middle vertebrae on the right side and a superior facet hemiarthroplasty replacement on the right side between the middle and bottom vertebrae on the same side.

Referring to FIG. 36, a dorsal view shows another example of how the inferior facet prosthesis 402 can articulate against the natural superior facet 43, or the inferior facet prosthesis 401 can articulate against the superior facet prosthesis 302. The right facet joint between the top vertebra 101 and the middle vertebra 102 is a unilateral replacement with the inferior facet of the top vertebra 101 replaced by the inferior facet prosthesis 401 and the superior facet of the middle vertebra 102 replaced by the superior facet prosthesis 302. The right facet joint between the middle vertebra 102 and the bottom vertebra 103 is a hemiarthroplasty replacement with the inferior facet replaced by the inferior facet prosthesis 402.

Figure 37:
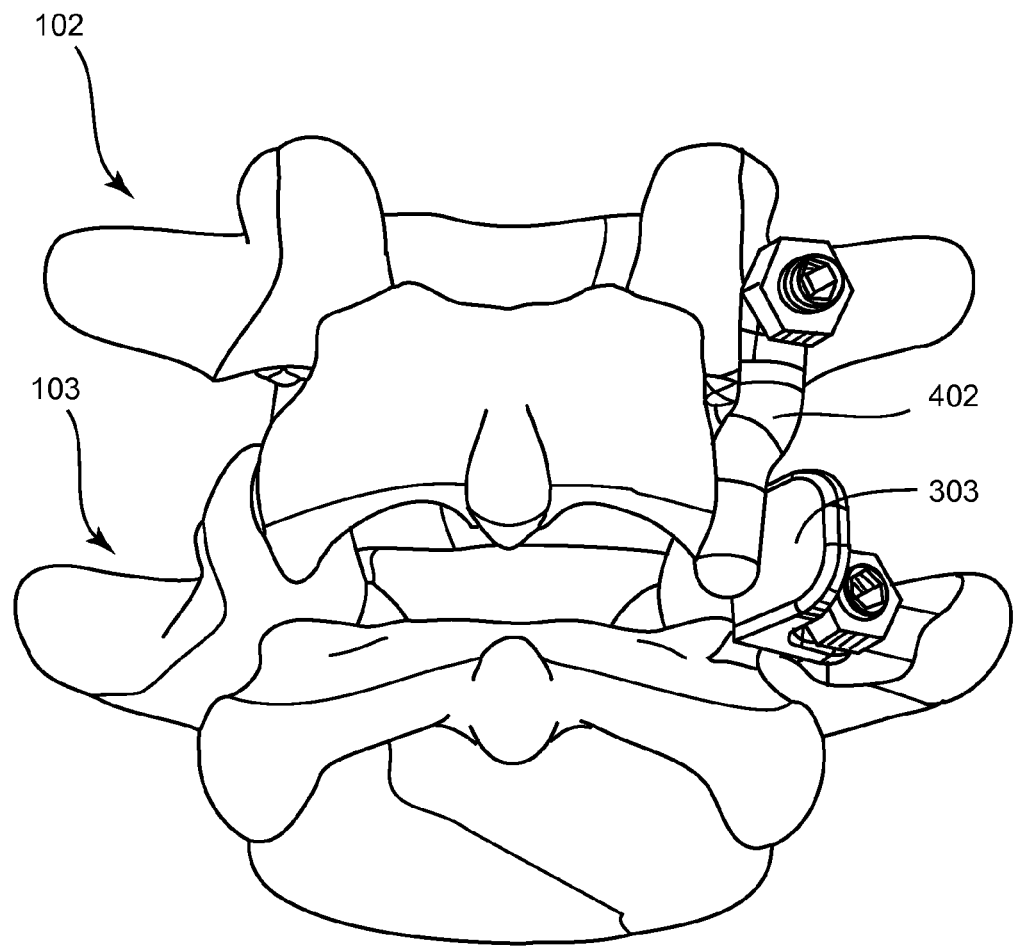
FIG. 37 is a spinal section of two vertebrae showing one inferior facet of the top vertebra and the adjoining superior facet of the bottom vertebra replaced by an articulating facet implant.

Referring to FIG. 37, a dorsal view illustrates only one level, that between the middle vertebra 102 and the bottom vertebra 103, being replaced on the right side. The right facet joint between the middle vertebra 102 and the bottom vertebra 103 is a unilateral replacement with the inferior facet of the middle vertebra 102 replaced by the inferior facet prosthesis 402 and the superior facet of the bottom vertebra 103 replaced by the superior facet prosthesis 303.

Figure 38:
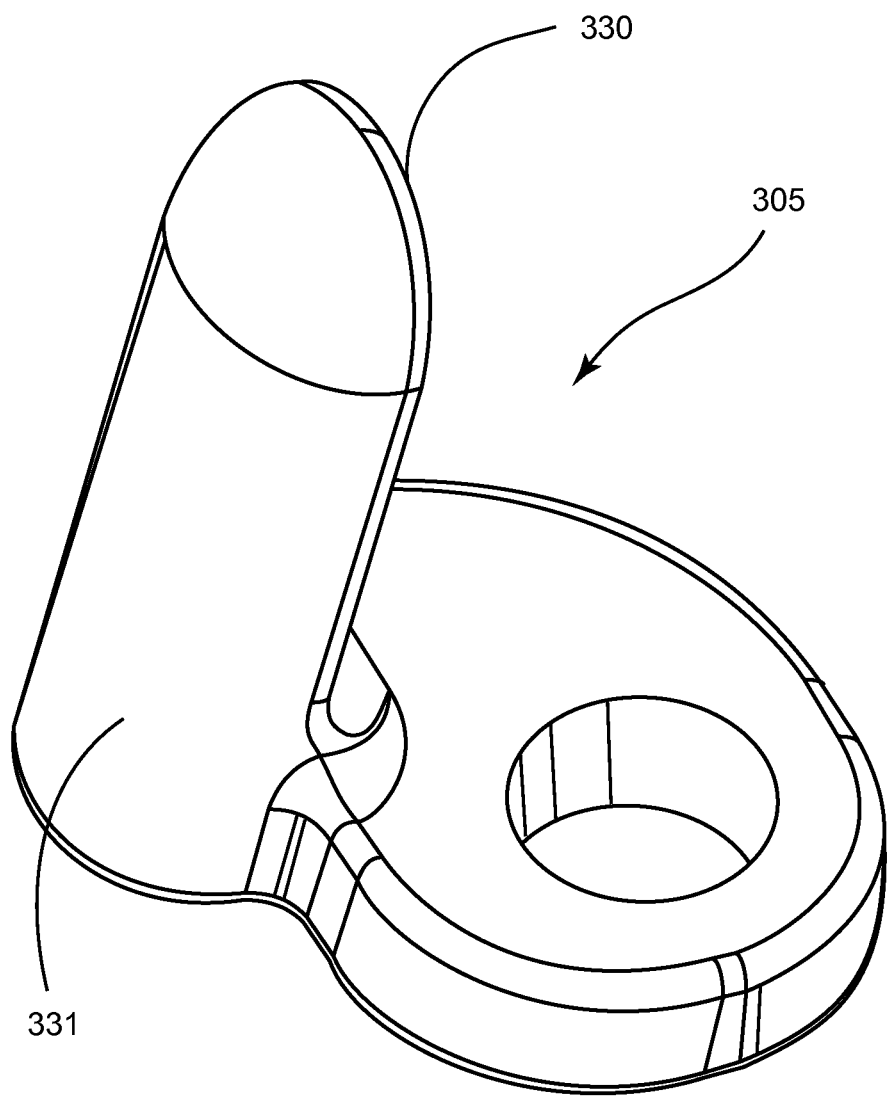
FIG. 38 is a perspective view of a curved superior facet prosthesis.
Figure 39:
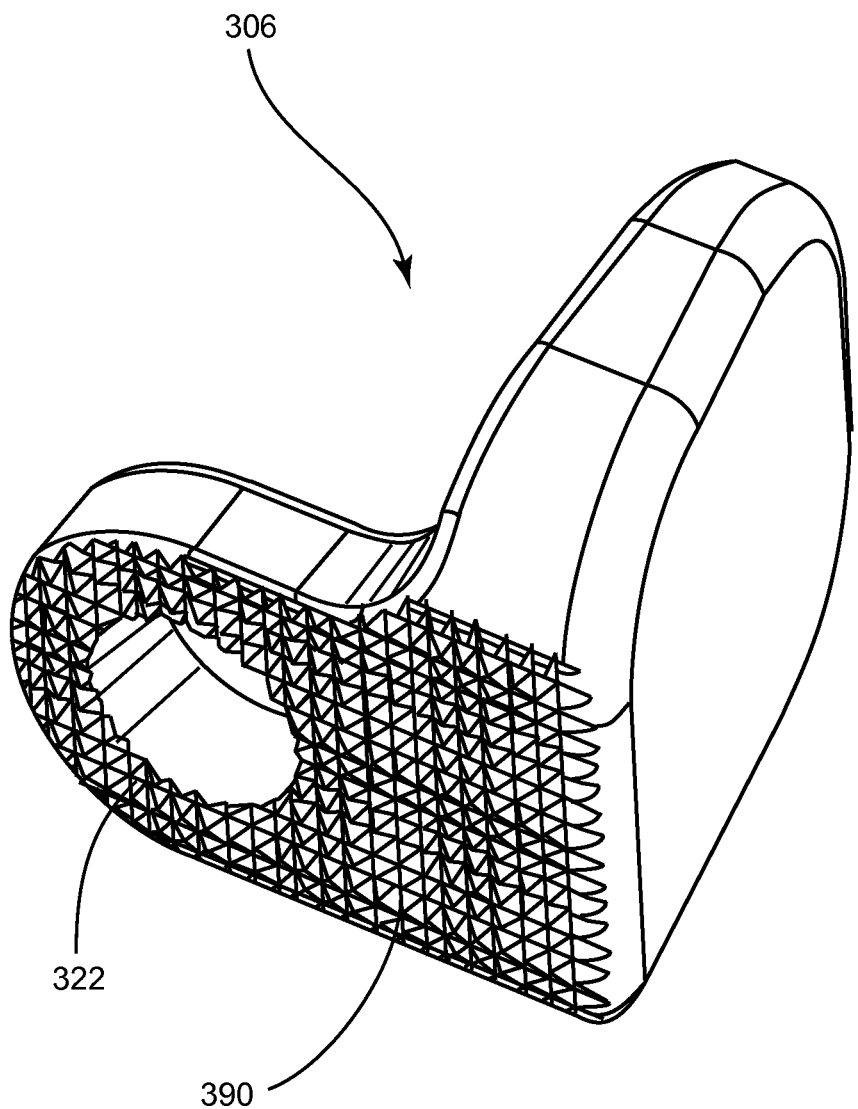
FIG. 39 is a perspective view of a superior facet prosthesis with a bone ingrowth surface.

FIG. 38 and FIG. 39 show two embodiments of the superior facet prosthesis. In FIG. 38, a perspective view illustrates an embodiment in which a curved superior facet prosthesis 305 with a curved articulating component 330 has a curved articulating surface 331. This curved articulating surface 331 allows for a more distributed contact load between an inferior facet prosthesis, such as the inferior facet prosthesis 400 of FIG. 23, and the curved articulating surface 331. This allows slightly more flexibility in the position that the surgeon places the curved superior facet prosthesis 305 than the superior facet prosthesis 300 previously described. The articulating surface 321 of the superior facet prosthesis 300 previously described is relatively flat. The articulating surface 331 of the curved superior facet prosthesis 305 is curved. Since the bearing portion of the inferior facet prosthesis 400 is columnar, the two prosthesis can be aligned on a slight mismatch and make more of an anatomic contact if the articulated surface is curved as in FIG. 38.

Referring to FIG. 39 a perspective view illustrates a bone ingrowth feature 390 on a superior facet prosthesis 306. The bone ingrowth feature 390 can be any surface that allows bone to grow into the implant between the first resection surface 112 of the vertebra 100 and the apposition surface 322 of the implant. Examples of bone ingrowth features 390 include porous coating of beads or meshes, electrochemically etched shapes and porous pads pressed onto the implant surface made from tantalum, titanium, cobalt chrome alloys and/or other biocompatible material such as hydroxylapatite or calcium phosphate ceramics.

Figure 40:
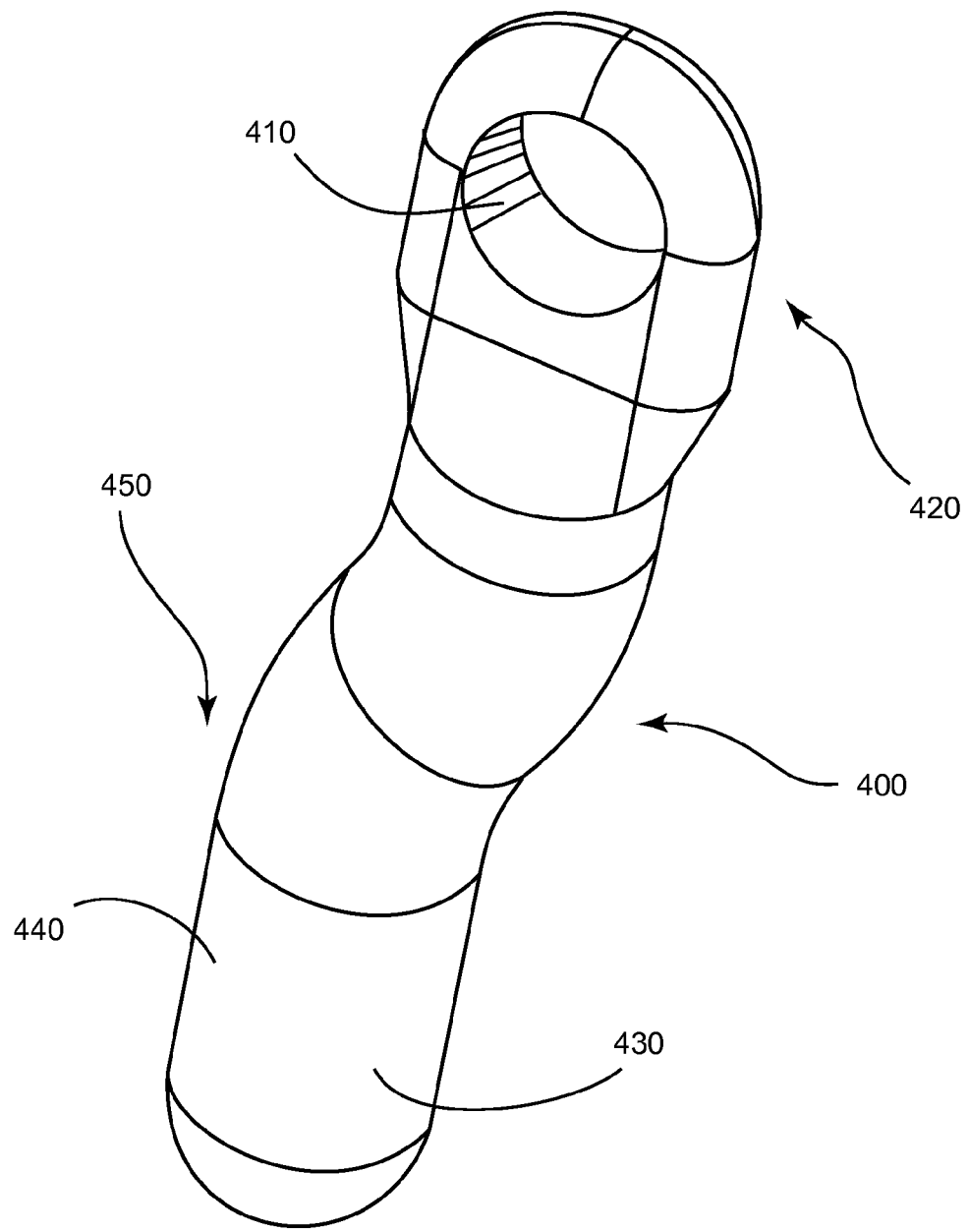
FIG. 40 is a perspective view of an inferior facet prosthesis.

Referring to FIG. 40, a perspective view shows the inferior facet prosthesis 400, which is formed in the general shape of a finger or talon. More particularly, the inferior facet prosthesis 400 is formed with a flange 420 on its superior side shaped to fit between the enlarged head 500 and either the superior facet prosthesis 300 or the first resection surface 112. The flange 420 has an opening 410 that is dimensioned to allow the inferior facet prosthesis 400 to fit over the proximal post 230 of the fixation element 200 and around the shaft portion 240 of the fixation element 200. The inferior facet prosthesis 400 also has an inferior portion 450 on the opposite side of the flange 420 that has a bone apposition side 440 that is shaped to contact the surface of the inferior facet resection surface 121 (FIG. 19) and a joint articulation side 430 that is shaped to articulate against a natural or prosthetic superior facet.

Figure 41:
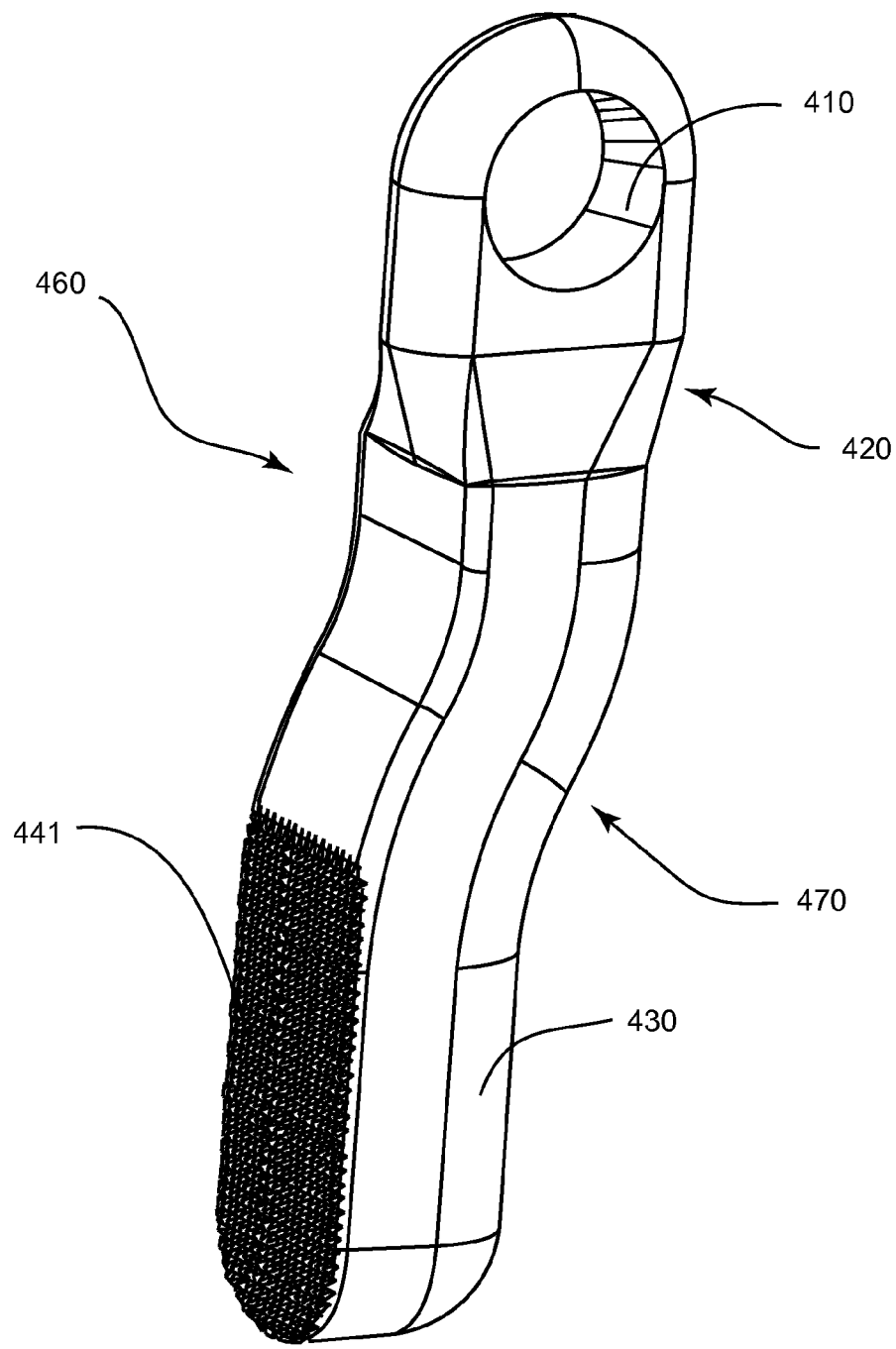
FIG. 41 is a perspective view of an inferior facet prosthesis with a bone ingrowth surface.

Referring to FIG. 41, a perspective view shows an inferior facet prosthesis 460 also formed in the general shape of a finger or talon. The inferior facet prosthesis 460 is formed with a superior end 420 having an opening 410 that is dimensioned and shaped to accept the fixation element 200. The inferior facet prosthesis 460 is generally columnar in shape, having a curved length designed to conform to the prepared anatomy of the vertebra 100. The inferior facet prosthesis 460 of FIG. 41 has an inferior portion 470, which is shown opposite the superior end 420, and slightly medially offset from the superior end 420. This medial offset of the opening 410 relative to the inferior portion 470 allows the inferior facet prosthesis 400 to be anchored to the bone by the fixation element 200 and secured to the bone by the enlarged head 500, or the superior facet prosthesis 300 in combination with the enlarged head 500, at an anatomical position that allows optimal bone fixation. The inferior facet prosthesis 460 of FIG. 41 has a bone ingrowth surface 441 and a joint articulating side 430 on its inferior end 470. In this embodiment, the bone ingrowth surface 441 is a textured structure that permits bone cells to grow into the implant surface. The shape of the bone ingrowth surface 441 can be a uniform textured surface as shown in FIG. 41, or can be a non-uniform randomized structure such as a open cell foam structure, a porous beaded structure, a wire mesh structure, an electrochemical etched structure, or other bone ingrowth structures known in the design of orthopedic implants. The bone ingrowth surface 441 is shaped to mate with the inferior resected bone surface 121 shown in FIG. 19 and FIG. 20.

Figure 42:
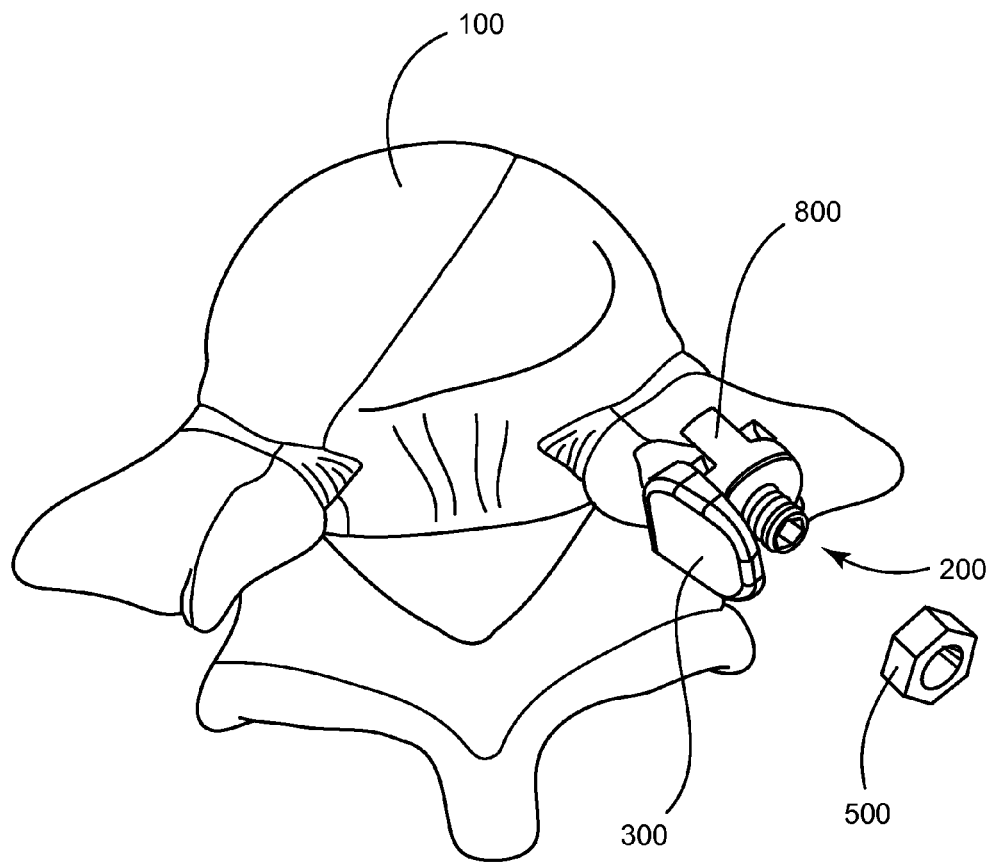
FIG. 42 is an exploded, perspective view illustrating the addition of a locking washer to the construction of the implant shown in FIG. 25.

FIG. 42 shows an exploded, perspective view of the vertebra 100 with the superior facet prosthesis 300 installed. An additional locking washer 800 is used to assist in stabilizing the attachment of the superior facet prosthesis 300 to the first resection surface 112. The construction of the implant assembly shown in FIG. 42 is similar to that of the assembly shown in FIG. 25 with the addition of the locking washer 800 that is placed over and around the proximal post 230 of the fixation element 200.

Figure 43:
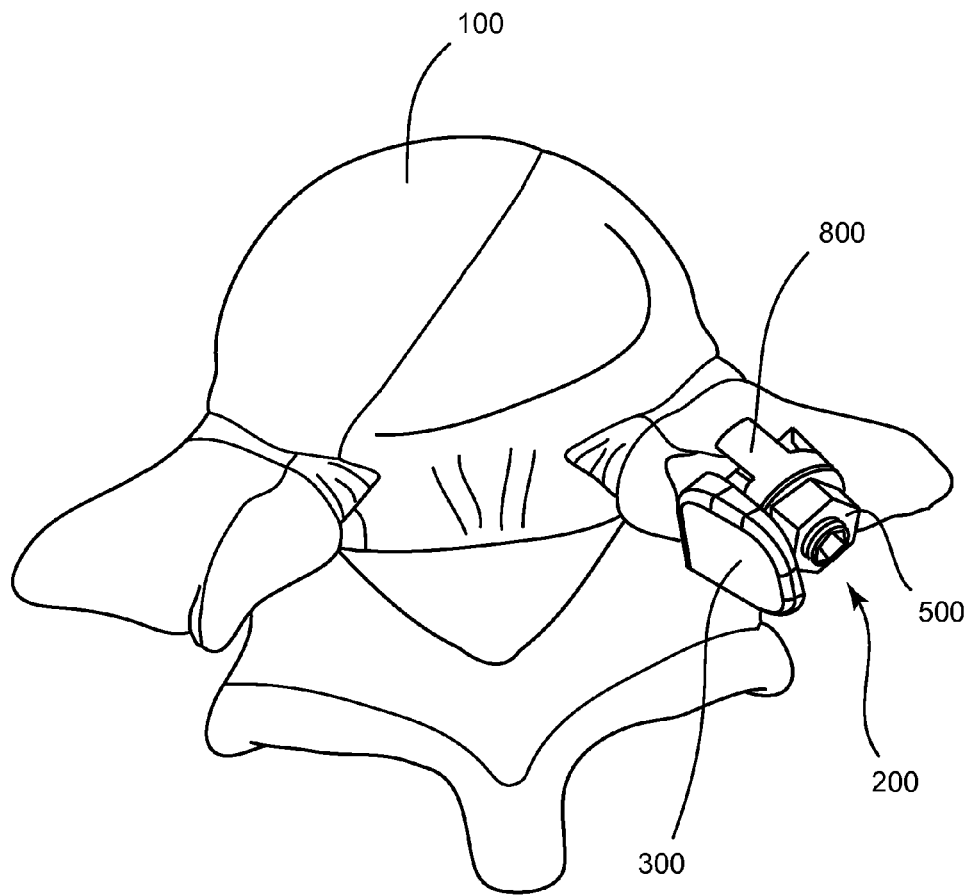
FIG. 43 is a perspective view illustrating the implant of FIG. 25 with a locking washer fully installed.

Referring to FIG. 43, a perspective view shows the same implant of FIG. 42 with the enlarged head 500 locked onto the fixation element 200 and pushing the locking washer 800 against the superior facet prosthesis 300 and into the bone tissue. This added bone penetration of the locking washer 800 helps to fix the superior prosthesis 300 such that the entire assembly is more mechanically stable with respect to the vertebra 100.

FIG. 43 shows a further step in the assembly of the implant construct described in FIG. 42. In FIG. 43, the locking washer 800 is secured over the fixation element 200 and into the bone tissue by the enlarged head 500. Although this embodiment of the locking washer 800 is only shown with the superior facet prosthesis 300, the locking washer 800 can alternatively be used to mechanically secure the inferior facet prosthesis 400, or the combination of the inferior facet prosthesis 400 and the superior facet prosthesis 300. In the embodiment of the locking washer 800 shown in FIG. 42 and FIG. 43, the locking washer 800 is placed over the superior facet prosthesis 300. However, the locking washer 800 may be placed under the superior facet prosthesis 300, under the inferior facet prosthesis 400 and the superior facet prosthesis 300, or between the superior facet prosthesis 300 and the inferior facet prosthesis 400 to stabilize the implant construct.

Figure 44:
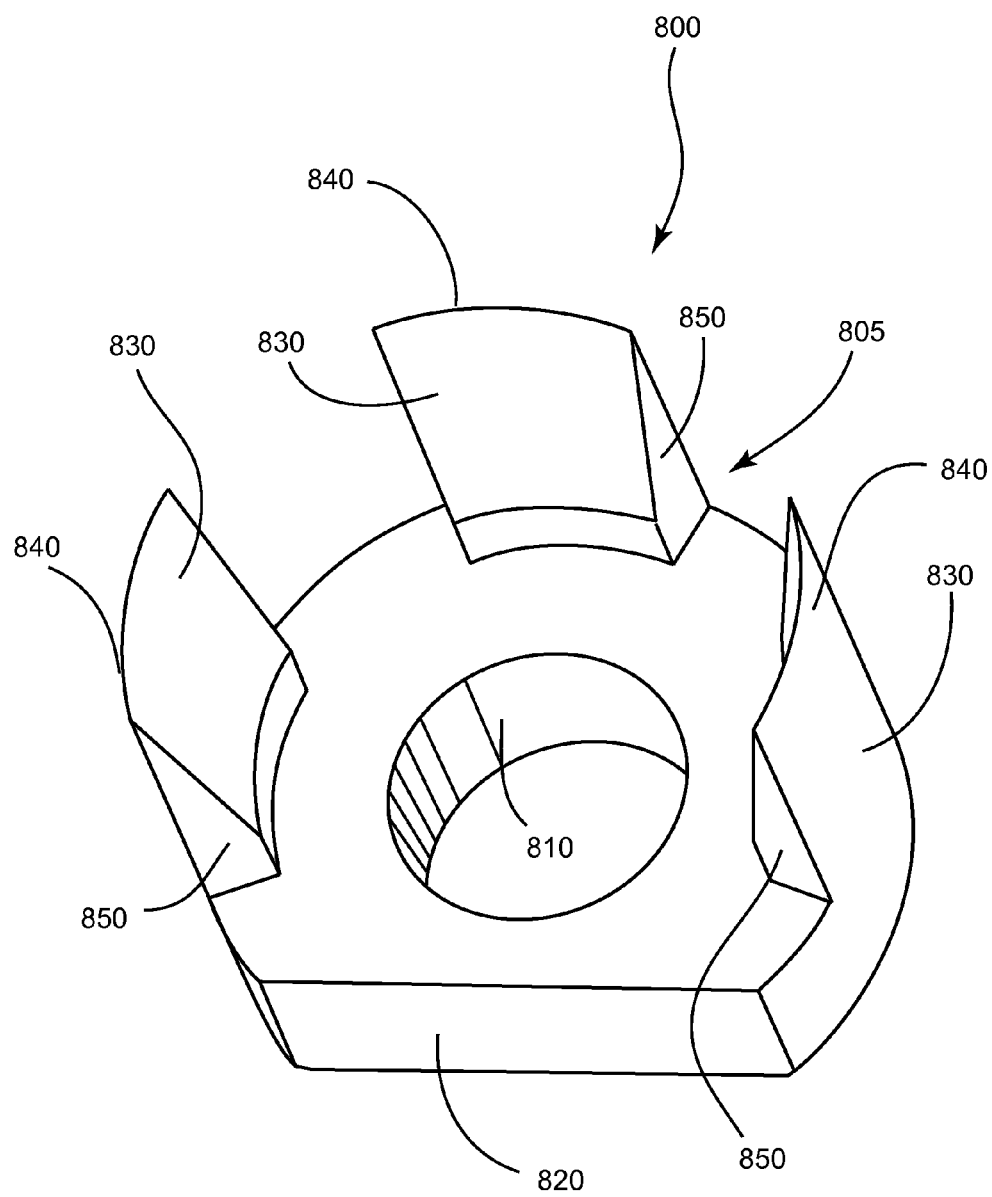
FIG. 44 is a perspective view of the locking washer shown in FIG. 42.

FIG. 44 shows a perspective view of the locking washer 800. The locking washer 800 has a body 805 with an opening 810 that is dimensioned to fit over the proximal post 230 of the fixation element 200. The locking washer 800 also has an anti-rotation feature 820 that mates with either the superior facet prosthesis 300 or the inferior facet prosthesis 400 or a combination of both the inferior facet prosthesis 400 and the superior facet prosthesis 400. The anti-rotation feature 820 shown in this embodiment is a flat surface, however, any feature that would rotationally constrain the locking washer 800 to the other components of the implant (such as a tab, groove, taper or other geometric shape) can be formed on the locking washer 800 as an anti-rotation feature. The locking washer 800 also has prongs 830 that pass into the bone tissue of the vertebra 100 to help stabilize the implant construct. The prongs 830 in this embodiment of the locking washer 800 are elongated protrusions that taper to a tissue penetration tip 840. The prongs have sidewalls 850 that provide a surface to resist torsion once the locking washer 800 penetrates the bone tissue. The prongs 830 may also be simple spikes that are either symmetrical or asymmetrical in cross-section that protrude from the locking washer body 805. The shape and length of the locking washer prongs 830 are dependent on how the locking washer 800 is used. The prongs 830 of the locking washer 800 that holds only one of the inferior facet prosthesis 400 or the superior facet prosthesis 300 to the vertebra 100 may be shorter than prongs of a locking washer that holds both the inferior facet prosthesis 400 and the superior facet prosthesis 300 to the vertebra 100.

Figure 45:
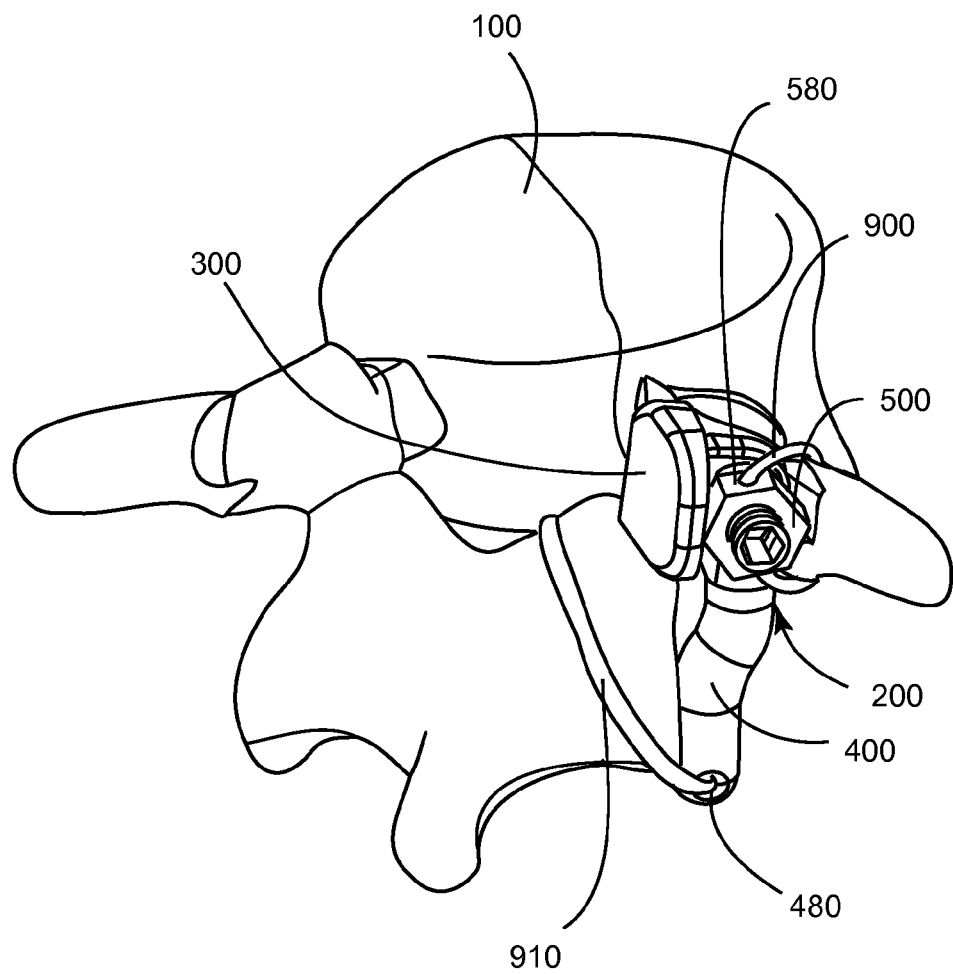
FIG. 45 is a perspective view of superior and inferior facet prostheses held against a vertebra by flexible fixation elements.

FIG. 45 shows a perspective view of the superior facet prosthesis 300 and inferior facet prosthesis 400 held to the vertebra 100 by an adjunctive flexible fixation element 900 and a secondary flexible fixation element 910. These flexible fixation elements 900 and/or 910 may be made from such constructs as suture, braided cable, wire, ribbon, and/or other constructs that have longer lengths than cross-sections and withstand larger loads in tension than in compression. The flexible fixation elements 900 and/or 910 may be manufactured from biocompatible metals, alloys such as cobalt chrome alloys, titanium alloys, stainless steel alloys, polymers, bioabsorbable materials, composites, or other materials that are biocompatible and can be formed into a flexible element structure 900 and/or 910 such as those shown in FIG. 45. The adjunctive flexible element 900 shown in FIG. 45 is shown attached to and securing the elongated head 500. A flexible element attachment portion 580 (e.g., including an opening) mates the flexible element 900 to the elongated head. However, the adjunctive flexible fixation element 900 may alternatively or additionally be attached to the fixation element 200, the superior facet prosthesis 300, the inferior facet prosthesis 400 or any combination of the above listed elements. A flexible fixation attachment portion 480 (e.g., including an opening) in the inferior facet prosthesis 400 allows the secondary flexible fixation element 910 to secure the inferior facet prostheses 400 to the vertebra 100. The flexible fixation elements 900 and/or 910 may be secured to the vertebra 100 by physically wrapping them around anatomic features such as the posterior arch 35, the spinous process 46, transverse process 105, or a combination of these anatomic features. The flexible element 900 and the secondary flexible element 910 may also be secured to the vertebra 100 by bone anchors such as anchors designed to anchor flexible fixation elements (such as suture, not shown) to bone. Suture anchors such as threaded suture anchors, barbed suture anchors, toggle suture anchors or any other means of anchoring a flexible fixation element to bone may be used to anchor the flexible fixation element 900 and/or the secondary flexible fixation element 910 to the vertebra 100.

Figure 46:
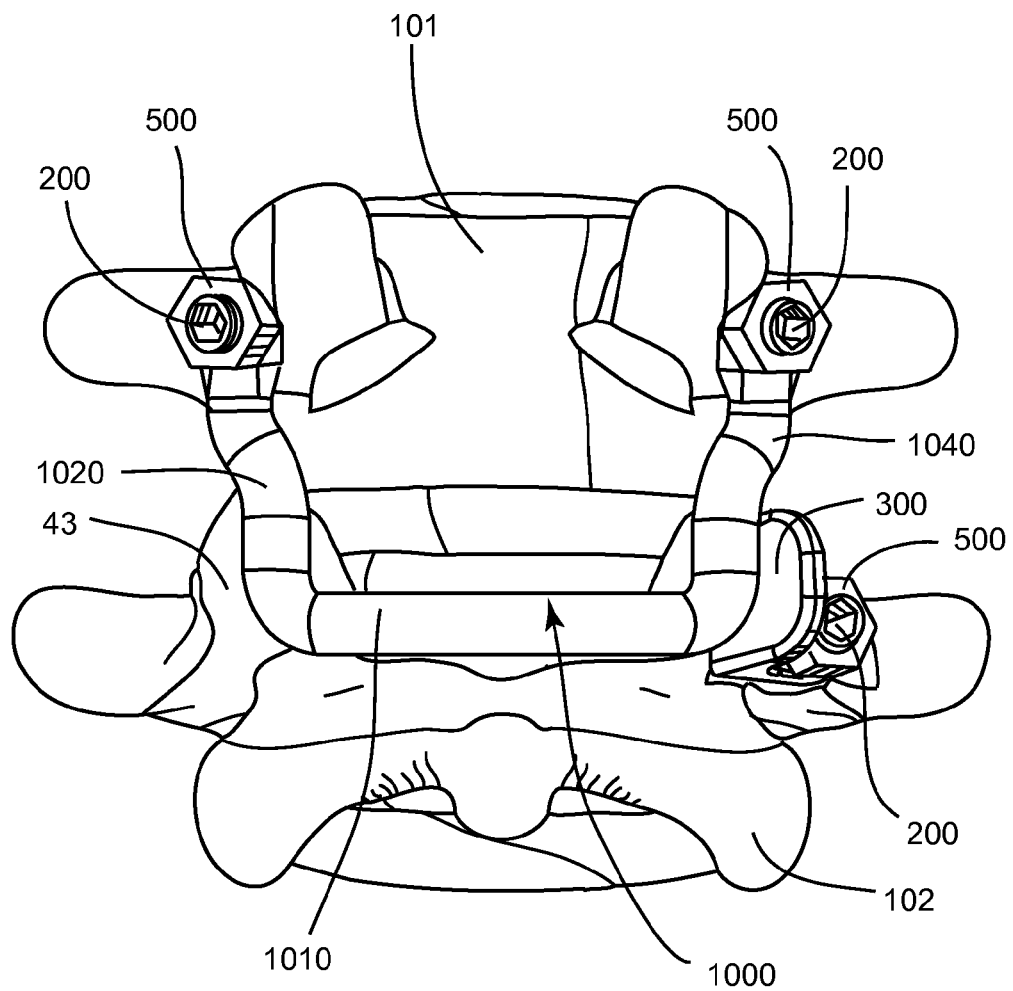
FIG. 46 is a dorsal view of a bilateral inferior implant.

FIG. 46 is a dorsal view of a bilateral inferior facet prosthesis 1000. The bilateral inferior facet prosthesis 1000 is a one-piece inferior facet prosthesis that has both a right inferior side 1040 and a left inferior side 1020 connected by a stabilizing bar 1010. Both the right inferior side 1040 and the left inferior side 1020 are designed to fix to the top vertebra 101 at the respective inferior resection surface 121 (FIG. 19) and at the first resection surface 112. The bilateral inferior facet prosthesis 1000 allows replacement of both the left and the right inferior facets. In this embodiment, the bilateral inferior facet prosthesis 1000 is placed over the left and right fixation elements 200 which extend into the bone of the top vertebra 101. In the embodiment shown in FIG. 46, the right inferior side 1040 is articulating against the right superior facet prosthesis 300 attached to the bottom vertebra 102. Also in this embodiment, the left inferior side 1020 is articulating against the left natural superior facet 43 of the bottom vertebra 102. The stabilizing bar 1010 of the bilateral inferior prosthesis 1000 is designed to stabilize the left side 1020 and the right side 1040 so that they are secure.

Figure 47:
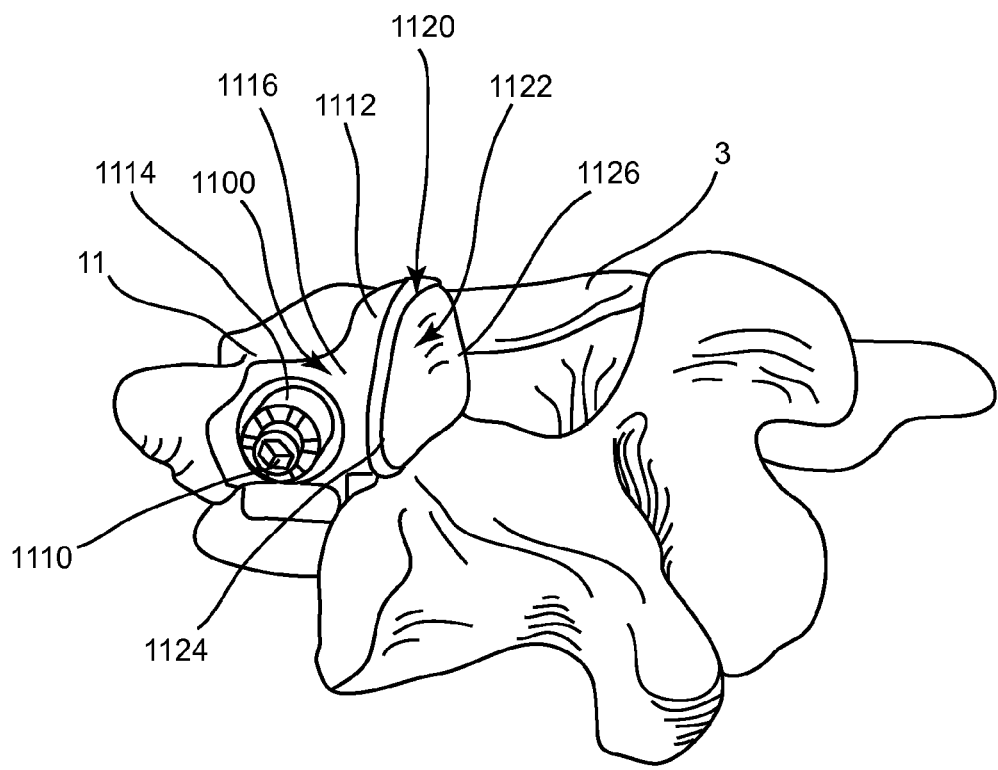
FIG. 47 is perspective view of a vertebra with an alternative embodiment of a superior facet prosthesis fixed to the bone by one embodiment of a fixation element.

FIG. 47 illustrates a perspective view of a left superior facet prosthesis 1100 coupled to the left pedicle 11 on the vertebra 3. The superior facet prosthesis 1100 has a bone apposition surface (not shown) that has been placed on a first resection surface 1112 and an opening (not shown) in a flange 1116 that surrounds a fixation element 1110, and coupled thereto by a locking fastener such as a castle nut 1114 or the like. The superior facet prosthesis 1100 has a superior facet articulating component 1120 with an articulating surface 1122 generally adjacent to the flange 1116. The articulating surface 1122 is oriented in a direction that faces approximately the same direction that the original anatomic superior articulating surface faced prior to resection. This orientation of the articulating surface 1122 allows the superior facet prosthesis 1100 to function as either a hemiarthroplasty implant by articulating against a natural anatomic inferior facet 6 or as a unilateral prosthesis by articulating against an inferior facet prosthesis on the vertebra superior (cephalad) to it, such as the inferior facet prosthesis 4 shown in FIG. 5, the inferior facet prostheses 10 shown in FIGS. 8 and 9, and the inferior facet prosthesis 400 shown in FIG. 40, as well as those described below.

The facet articulating component 1120 is preferably formed in the general shape of a blade or wing ear, wherein the articulating surface 1122 has a concave shape. In the embodiment shown, the articulating surface 1122 curves from an orientation generally perpendicular to the flange 1116 towards an orientation generally parallel to the flange 1116 from a distal end 1124 thereof to a proximal end 1126 thereof.

The concave shape of the articulating surface 1122 provides more tolerance for a miss-match with the natural anatomic inferior facet 6 or with the inferior facet prosthesis 4 on the vertebra superior to it. Functionally, the clearance between the concave shape of the articulating surface 1122 and the adjacent inferior facet 6 or inferior facet prosthesis 4 increases as the patient bends forward (flexion) and decreases as the patient bends backward (extension). Thus in flexion the patient has more facet movement allowing for more torsion (twisting) and lateral bending (side to side movement) than in a neutral stance. As the patient extends, the articulating members are more constrained in torsion and lateral bending. This mimics the natural anatomic constraints of the spinal facets.

Figure 48:
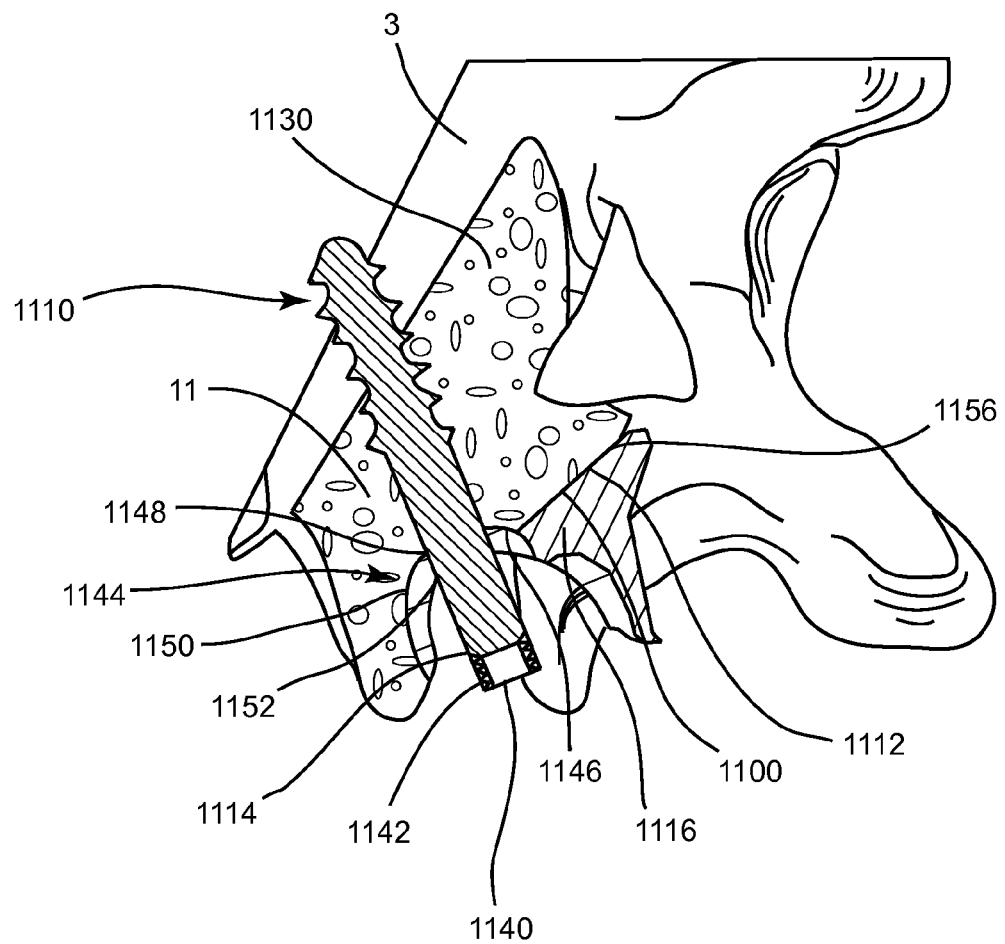
FIG. 48 is a perspective, cross-sectional view of the embodiment of the superior facet prosthesis and fixation element of FIG. 47 showing the semispherical shape of the resection and the approximately similarly semispherical shape of the apposition side of the superior facet prosthesis, as well as an angled resection and corresponding angled flat on the apposition side of the superior facet prosthesis in combination with the semispherical resection.

FIG. 48 is a perspective view of the same construct shown in FIG. 47, but with the implants and the vertebra 3 cut by a cross-sectioning plane 1130 placed along an axis that passes through the center of the fixation element 1110. The cross-section plane 1130 shown cutting through the vertebra 3 and the implant of FIG. 47 is shown for visualization purposes to illustrate, using a cross-sectioned view, how the vertebra 3, fixation element 1110, and superior facet prosthesis 1100 engage each other.

The fixation element 1110 provides a mechanism that affixes the superior facet prosthesis 1100 to vertebra 3. Fixation element 1110 is implanted into the interior bone space of the left pedicle 11 (FIG. 6) on the vertebra 3 and may or may not extend into the vertebral body of vertebra 3 to provide additional stability. The fixation element 1110 can take the form of a screw (as shown), or any of the devices shown in FIGS. 28-30. The fixation element 1110 has a drive feature 1140, which is an internal hex in the embodiment shown in FIG. 48. However, any shape of drive feature that transmits the loads necessary to drive the fixation element 1110 into the vertebra 3 can be formed on a proximal post 1142 of the fixation element 1110.

The depth of the drive feature 1140 formed in the proximal post 1142 of the fixation element 1110 is seen in the cross-sectional view of FIG. 48. The drive feature 1140 may be an internal drive feature such as the hex socket shown in this embodiment, or an external drive feature with geometry on the periphery of the proximal post 1142 of the fixation element 1110 that engages with a corresponding internal drive feature on a driver tool (not shown). The flange 1116 of the superior facet prosthesis 1100 is secured to the fixation element 1110 by the castle nut 1114 or the like.

The flange 1116 of the superior facet prosthesis 1100 includes a coupling portion 1144 having a generally semispherical bone engaging surface 1150 on the apposition side of the superior facet prosthesis 1100 that engages a corresponding semispherical resection 1146 in the bone bed of the left pedicle 11 on the vertebra 3. The term semispherical relates to a surface that includes some sectorial portion of a sphere, which may be less than a hemisphere. A semispherical surface may be concave or convex. A surface that is semispherical or generally semispherical may have some deviations from a precise semispherical shape.

The semispherical resection 1146 may be said to be "inversely shaped" with respect to the coupling portion because the semispherical resection 1146 has a generally concave surface that matches the generally convex surface of the coupling portion 1144. Although the coupling portion 1144 and the semispherical resection 1146 are semispherical in the embodiment of FIGS. 47 and 48, in alternative embodiments, they may have a variety of other matched shapes, including three-dimensional parabolas, ellipsoids, and other regularly or irregularly curved or flat-sided shapes. Furthermore, although the coupling portion 1144 is convex and the semispherical resection 1146 is concave in the embodiment of FIGS. 47 and 48, in alternative embodiments, the shapes may be reversed so that a coupling portion is concave and a resection is convex.

In the embodiment of FIGS. 47 and 48, the coupling portion 1144 is integrally formed with the articulating surface 1122 of the superior facet articulating component 1120. The coupling portion 1144 may be said to be "attached to" the articulating surface 1122 because in this application, the term "attached" is used broadly to include parts that are integrally formed with each other as well as parts that are formed separately and subsequently coupled together.

The semispherical resection 1146 in the bone bed allows for less transverse process to be resected (vs. a flat bone bed resection). The semipherical resection 1146 in the bone bed also allows for more stable support of the superior facet prosthesis 1100, than does a flat bone bed resection, as the superior facet prosthesis 1100 is polyaxially supported in such a way as to resist any shear forces applied between the semispherical resection 1146 and the coupling portion 1144. In this application, "polyaxial" refers to a linear or angular force or motion acting with respect to at least two perpendicular axes. The coupling portion 1144 may seat directly against the semispherical resection 1146. In this application, an item that "seats directly against" another is positioned to abut the other item so that surfaces of the two items are in contact with each other.

The coupling portion 1144 has a fixation element receiving aperture 1148 that can be made slightly larger than a circumferential diameter of the fixation element 1110 taken in a direction perpendicular to a longitudinal axis thereof to provide accurate polyaxial seating of the implant 1100 in relation to the resected bone bed and fixation element 1110, as well as to provide increased tolerance for miss-match. An implant engaging end 1154 of the castle nut 1114 (or other fastener) also has a semispherical shape for engaging a semispherical nut engaging side of the coupling portion 1144 of the superior facet prosthesis 1100 at the final position of the superior facet prosthesis 1100.

The semispherical shape of the coupling portion 1144 enables the coupling portion 1144 to move polyaxially against the semispherical resection 1146. Movement "against" the semispherical resection refers to movement in which the coupling portion 1144 remains substantially continuously in contact with the semispherical resection 1146 so as to slide against the semispherical resection 1146. Accordingly, during installation, a surgeon can position the coupling portion 1144 against the semispherical resection 1146 and then pivot the coupling portion 1144 along three perpendicular axes, without removing the coupling portion 1144 from the semispherical resection 1146. The coupling portion 1144 simply rotates against the semispherical resection 1146.

The phrase "polyaxial motion" refers to any combination of translation and/or rotation along at least two perpendicular axes. Since the coupling portion 1144 is pivotable with respect to the semispherical resection 1146 along three perpendicular axes, the coupling portion 1144 is "tri-axially pivotable" with respect to the semispherical resection 1146.

When the superior facet prosthesis 1100 has been rotated to the proper orientation, the articulating surface 1122 is positioned for proper articulation against the corresponding inferior facet or inferior facet prosthesis. The orientation of the coupling portion 1144 may then be fixed with respect to the semispherical resection 1146 by tightening the castle nut 1114 (or another fastener) on the fixation element 1110, thereby firmly gripping the coupling portion 1144 against the semispherical resection 1146. Accordingly, the coupling portion 1144 is "selectively polyaxially movable" with respect to the semispherical resection 1146 because the coupling portion 1144 is movable with respect to the semispherical resection 1146 along multiple perpendicular axes until the surgeon decides to fix its disposition.

In alternative embodiments (not shown) of the invention, tri-axial pivotal movement need not be provided. Rather, a coupling portion and a corresponding resection surface may have a cylindrical, flat-sided, splined, or other shape designed to enable relative translation in addition to or in place of rotation. In place of the fixation element receiving aperture 1148, an elongated fixation element receiving aperture may be used to accommodate relative translation between the coupling portion and a fixation element. Alternatively, a coupling portion and a resection surface may be shaped to provide relative pivotal motion along only one or two axes.

In an alternative embodiment the implant engaging end 1154 of the castle nut 1114 (or other fastener) can be deformable such that the implant engaging end 1154 conforms under pressure to the adjacent surface of the coupling portion 1144 regardless of the angle of the surface with respect to the axis of the castle nut 1114. The deformable end can be formed of a plastic such as polyethylene attached to the metal body of the castle nut 1114, but is preferably formed of a substance that hardens over time, such as a fast-curing and biocompatible resin or a material that is heated prior to insertion into the patient and hardens upon cooling to the patient's body temperature. The material that hardens over time provides more stability than the deformable material, though both provide acceptable results.

FIG. 48 also shows an angled resection 1112 and corresponding angled flat 1156 on the apposition side of the superior facet prosthesis 1100 in combination with the semispherical resection 1148.

The surfaces of the apposition side of the coupling portion 1144 and flat 1156, as well as fixation element 1110, may or may not include porous coatings to facilitate bone ingrowth to enhance the long-term fixation of the implant. Furthermore, such porous coatings may or may not include osteoinductive or osteoconductive substances to further enhance the bone remodeling into the porous coating.

Figure 49:
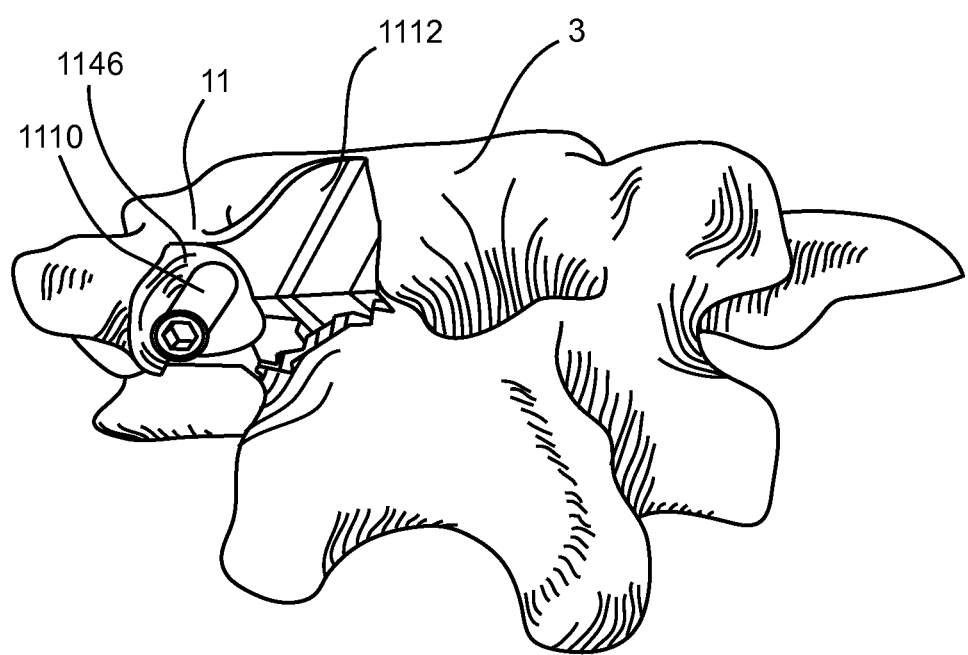
FIG. 49 is a perspective view of the resected vertebra without the superior facet prosthesis attached to the vertebra, in which the fixation element is installed in the vertebra.

FIG. 49 shows a perspective view of the vertebra 3 with a fixation element 1110 portion implant placed through the semispherical resection 1146 in the resection surface 1112 and into the bone of the left pedicle 11. The fixation element 1110 is aligned and placed into the pedicle 11 in a manner similar to that of other pedicle screws for posterior stabilization vertebrae fusion procedures.

Figure 50:
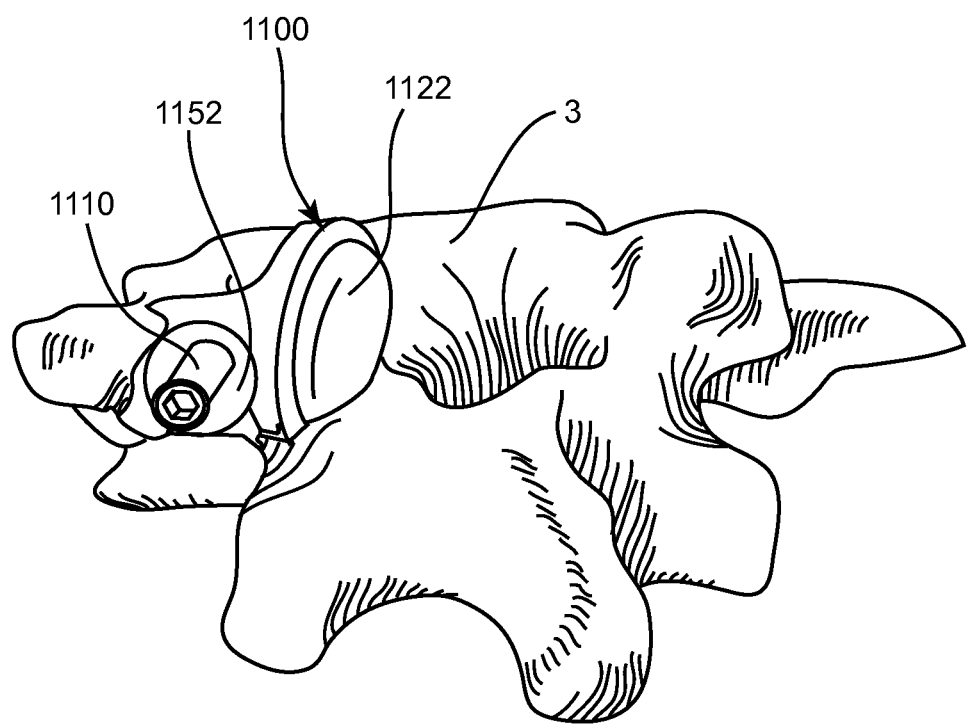
FIG. 50 is a perspective view of the resected vertebra with the superior facet prosthesis attached to the vertebra, with the fixation element installed in the vertebra, but without the locking fastener shown in FIG. 47.

In FIG. 50, a perspective view illustrates the superior facet prosthesis 1100 in place around the fixation element 1110. The castle nut 1114 has not yet been installed. As shown, the coupling portion 1144 has a semispherical nut engaging surface 1152.

Figure 51:
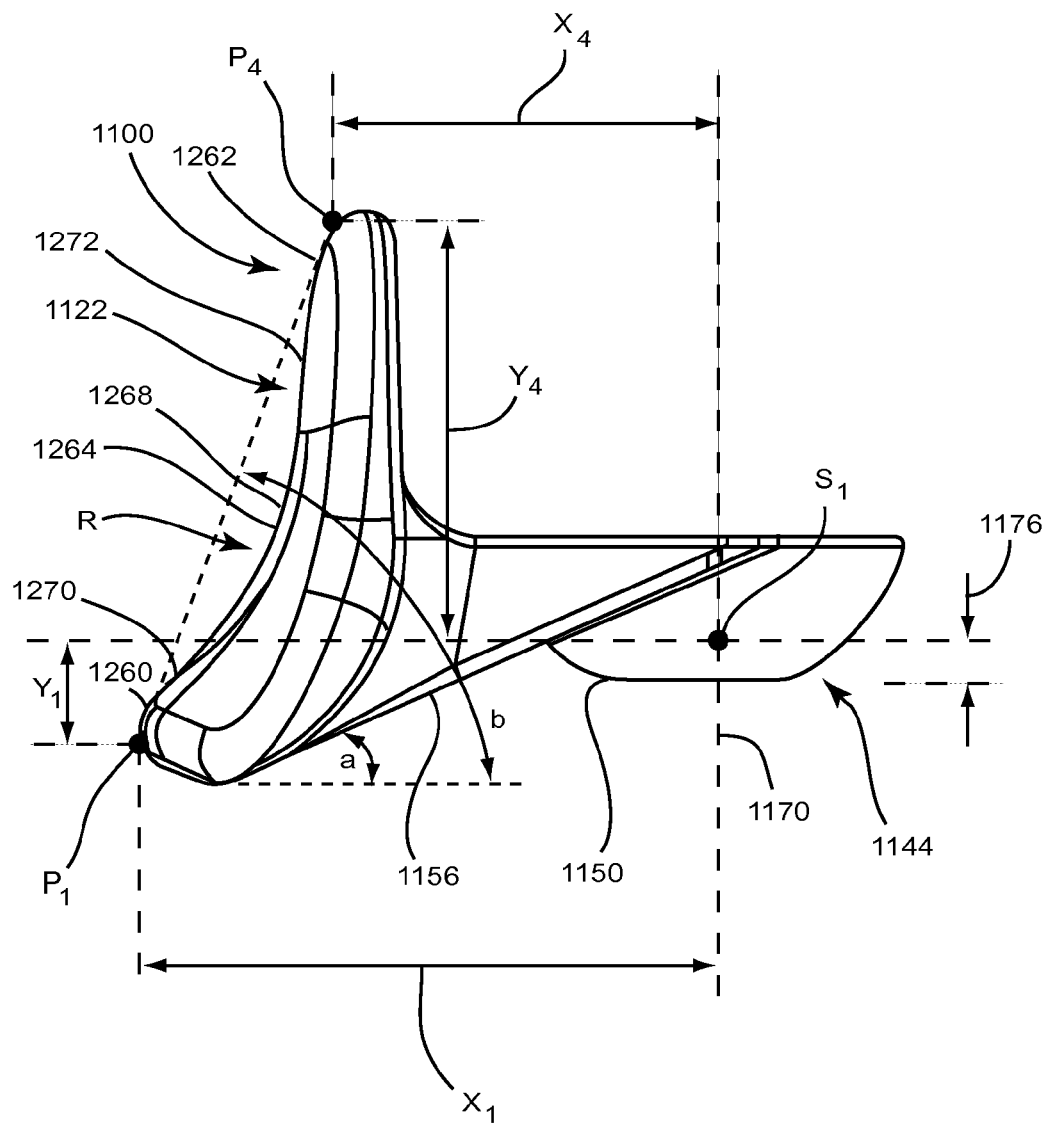
FIG. 51 is a top view of the superior facet prosthesis showing the semispherical shape of the bone apposition side in combination with the angled flat on the bone apposition side.

FIG. 51 is a top view of the superior facet prosthesis 1100, particularly showing the curved shape of the articulating surface 1122 and the semispherical bone engaging surface 1150 of the coupling portion 1144. Additionally, FIG. 51 more clearly illustrates the angled flat 1156 on the apposition side of the superior facet prosthesis 1100.

Figure 52:
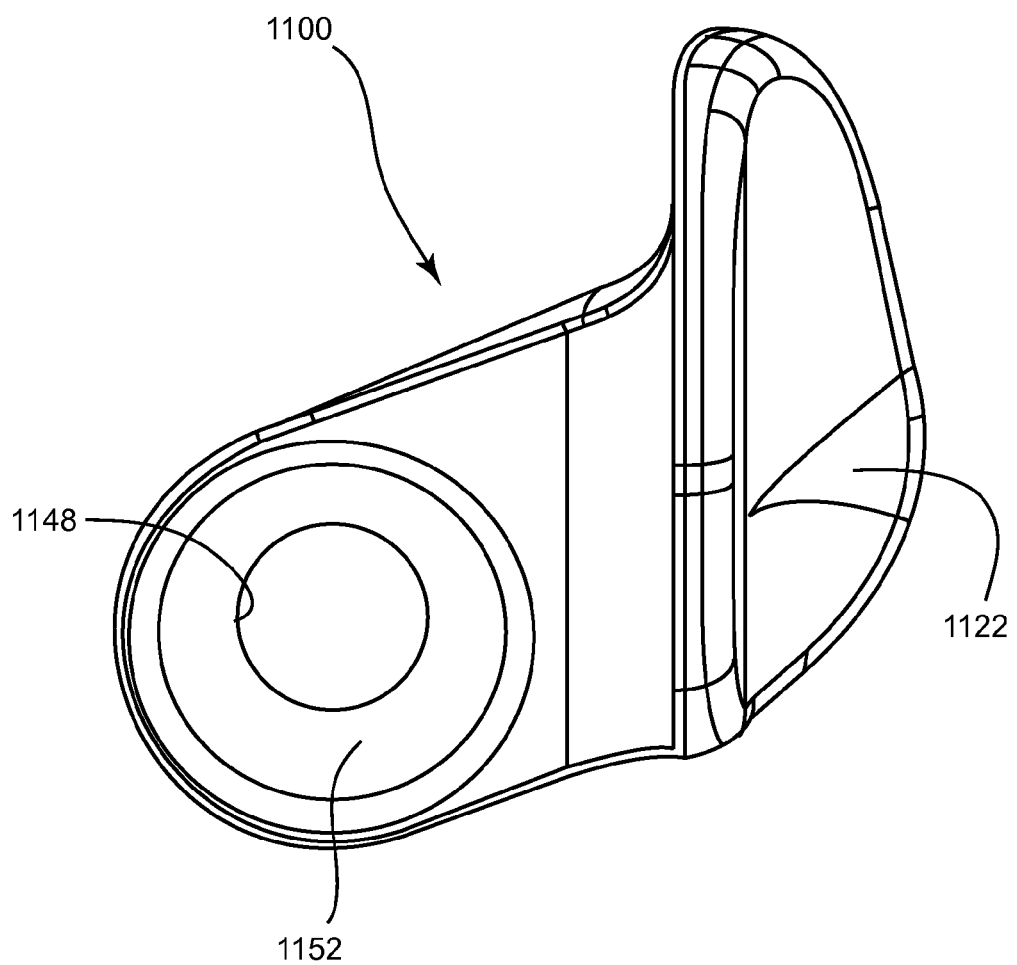
FIG. 52 is a rear view of the superior facet prosthesis showing the semispherical nut engaging surface on the top of the area that is design to connect to the fixation element and the locking nut, or the inferior prosthesis and the fixation element.

FIG. 52 is an illustration of a rear view of the superior facet prosthesis 1100. In this context, "rear" means as viewed from along the axis of the fixation element receiving aperture 1148. FIG. 52 particularly shows the curved shape of the articulating surface 1122 and the semispherical nut engaging surface 1152 of the coupling portion 1144.

Figure 53A:
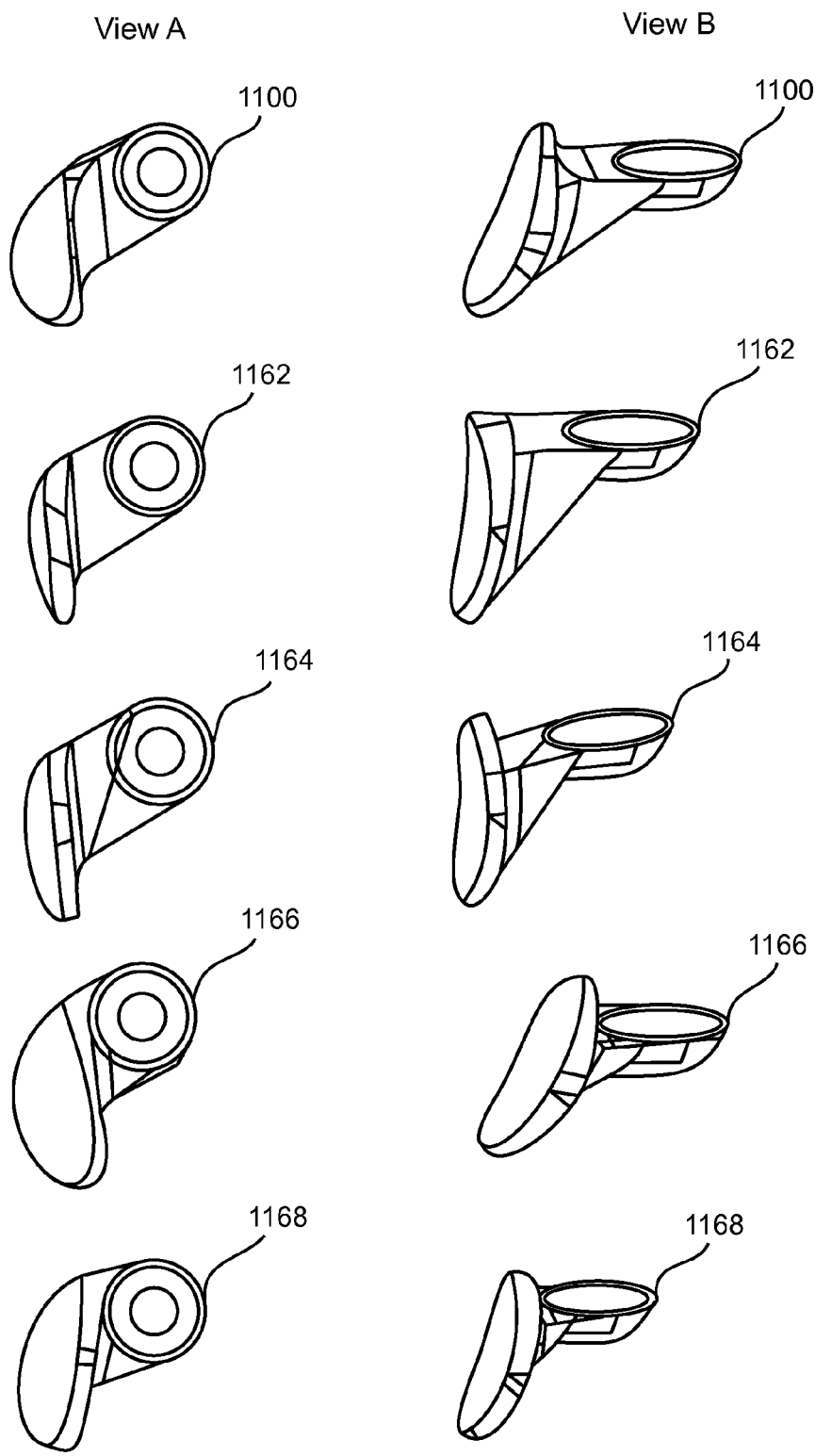
FIG. 53A is a rear view and a perspective view of a plurality of superior facet prostheses of a kit.

FIG. 53A shows a kit including a plurality of differently configured left superior facet prostheses 1100, 1162, 1164, 1166, 1168. View A is a rear view of the superior facet prostheses 1100, 1162, 1164, 1166, 1168, while View B illustrates a perspective view of the laterally adjacent prosthesis 1100, 1162, 1164, 1166, 1168 rotated 90.degree. As shown, the superior facet prostheses 1100, 1162, 1164, 1166, 1168 have differing physical dimensions.

Referring again to FIG. 51, which shows a single superior facet prosthesis 1100, some of the physical dimensions that change between the differently sizes superior facet prostheses 1100, 1162, 1164, 1166, 1168 in the kit (FIG. 53A) are a resection angle ($\alpha$), an x offset ($X_1$), a y offset ($Y_1$), a facet angle ($\beta$), and a facet articulation radius (R). Exemplary values for the foregoing will be provided below. Although the exemplary values relate primarily to L5 superior and L4 inferior, they may apply to other combinations of vertebrae in the lower back and/or the sacrum. One or more of these variables can change between the different superior facet prosthesis sizes.

P1 is the most medial and anterior point on the articulating surface 1122. The superior pedicle axis 1170 is the axis that is collinear with the longitudinal axis of the fixation element 1110 that is positioned through the pedicle 11 nearest to the resected superior facet (not shown). The superior pedicle axis 1170 extends through a saddle point S1, which is offset as shown, by an offset 1176, which may be about 2 mm, from the fixation element receiving aperture 1148. The superior pedicle axis 1170 is parallel with the direction of the y offset (Y.sub.1). The direction of the x offset (X.sub.1) is perpendicular to the direction of the y offset (Y.sub.1). The direction of the x offset (X.sub.1) is generally, but not precisely, lateral to medial with respect to the central axis of the patient's spine.

P4 is the most posterior point on the articulating surface 1122. As shown, P4 is displaced from the saddle point S1 by an x offset ($X_4$) and a y offset ($Y_4$). The direction of the $X_4$ offset is parallel to that of the $X_1$ offset, and the direction of the $Y_4$ offset is parallel to that of the $Y_1$ offset.

The resection angle ($\alpha$) for the superior facet prostheses 1100 can range from 50 to 85°. However, the optimal range of the resection angle ($\alpha$) for the majority of patients will range from 30° to 70°. Thus, by way of example, a family containing nine sets of superior facet prostheses 1100 can be provided with the resection angles ($\alpha$) varying in increments of 5°. Sets of superior facet prostheses 1100 would be provided with resection angles ($\alpha$) at 30°, 35°. 40°, 45°, 50°, 55°, 60°, 65° and 70°.

The x offset ($X_1$) for the superior facet prosthesis 1100 can range from 5 mm to 30 mm. However, for the majority of patients, the x offset ($X_1$) will range from 10 mm to 20 mm. Therefore a family of superior facet prostheses 1100 can be provided with the x offset ($X_1$) varying in increments of 5 mm. Thus, sets of superior facet prostheses 1100 would be provided with x offset ($X_1$) at 10 mm, 12 mm, 14 mm, 16 mm, 18 mm, and 20 mm to provide superior facet prostheses 1100 that cover the statistical range for the majority of the population of patients needing superior facet prostheses 1100.

The y offset ($Y_1$) for the superior facet prosthesis 1100 can range from 2 mm to 20 mm. However, for the majority of patients, the y offset ($Y_1$) will range from 5 mm to 15 mm. Therefore a family of superior facet prostheses 1100 can be provided with the y offset ($Y_1$) varying in increments of 2 mm. Thus, sets of superior facet prostheses 1100 would be provided with y offset ($Y_1$) at 5 mm, 7 mm, 9 mm, 11 mm, 13 mm, and 15 mm to provide superior facet prostheses 1100 that cover the statistical range for the majority of the population of patients needing superior facet prostheses 1100.

The x offset ($X_4$) for the superior facet prosthesis 1100 can range from about 5 mm to about 25 mm. However, for the majority of patients, $X_4$ will range from about 8 mm to about 20 mm. A family of superior facet prostheses may be provided with $X_4$ values varying in increments of 2 mm. Thus, sets of superior facet prostheses 1100 would be provided with $X_4$ values of 8 mm, 10 mm, 12 mm, 14 mm, 16 mm, 18 mm, and 20 mm to provide superior facet prostheses 1100 that cover the statistical range for the majority of the population of patients needing superior facet prostheses 1100.

The y offset ($Y_4$) for the superior facet prosthesis 1100 can range from about −5 to about 15 mm. However, for the majority of patients, $Y_4$ will range from about −2 mm to about 10 mm. A family of superior facet prostheses may be provided with $Y_4$ values varying in increments of 2 mm. Thus, sets of superior facet prostheses 1100 would be provided with $Y_4$ values of −2 mm, 0 mm, 2 mm, 4 mm, 6 mm, 8 mm, and 10 mm to provide superior facet prostheses 1100 that cover the statistical range for the majority of the population of patients needing superior facet prostheses 1100.

The facet angle ($\beta$) for the superior facet prosthesis 1100 can range from 50° to 120°. However, for the majority of patients, the facet angle ($\beta$) will range from 60° to 100°. Therefore a family of superior facet prostheses 1100 can be provided with the facet angle ($\beta$) varying in increments of 5°. Thus, sets of superior facet prostheses 1100 would be provided with the angle ($\beta$) at 60°, 65°, 70°, 75°, 80°, 85°, 90°, 95°, and 100° to provide superior facet prostheses 1100 that cover the statistical range for the majority of the population of patients needing superior facet prostheses 1100.

Once the surgeon assesses the anatomy of the superior facet that is being replaced, a particular superior facet prosthesis 1100 is selected that has the curvature and overall angle of the articulating surface 1122, with respect to the flange 1116 that best fits the anatomy of the level of vertebra, the left or right side, and the size of the patient's anatomy being replaced. Thus a kit containing various sizes and shapes of superior facet prostheses 1100 is provided to the surgeon and the surgeon selects the superior facet prosthesis 1100 that best suits the situation.

According to one example, such a kit may contain nine left superior facet prostheses, which may be dimensioned to provide a variety of combinations of values for a, X.sub.1, Y.sub.1, .beta., X.sub.4, Y.sub.4, and R, within the ranges listed above. If desired, one or more of the above-listed variables may remain constant over the entire kit. For example, R may have a constant value, such as 11.5 mm, for all members of the kit.

The prostheses 1100, 1162, 1164, 1166, 1168 of the kit of FIG. 53A are not simply scaled up or down, but are varied according to a number of carefully selected parameters to cover the vast majority of morphologies occurring in the L5 vertebra. In a similar manner, a plurality of inferior facet prostheses adapted to replace inferior facets can be provided either as a separate kit, or in combination with the kit of FIG. 53A. Such a kit will be shown and described in connection with FIG. 53D.

Figure 53B:
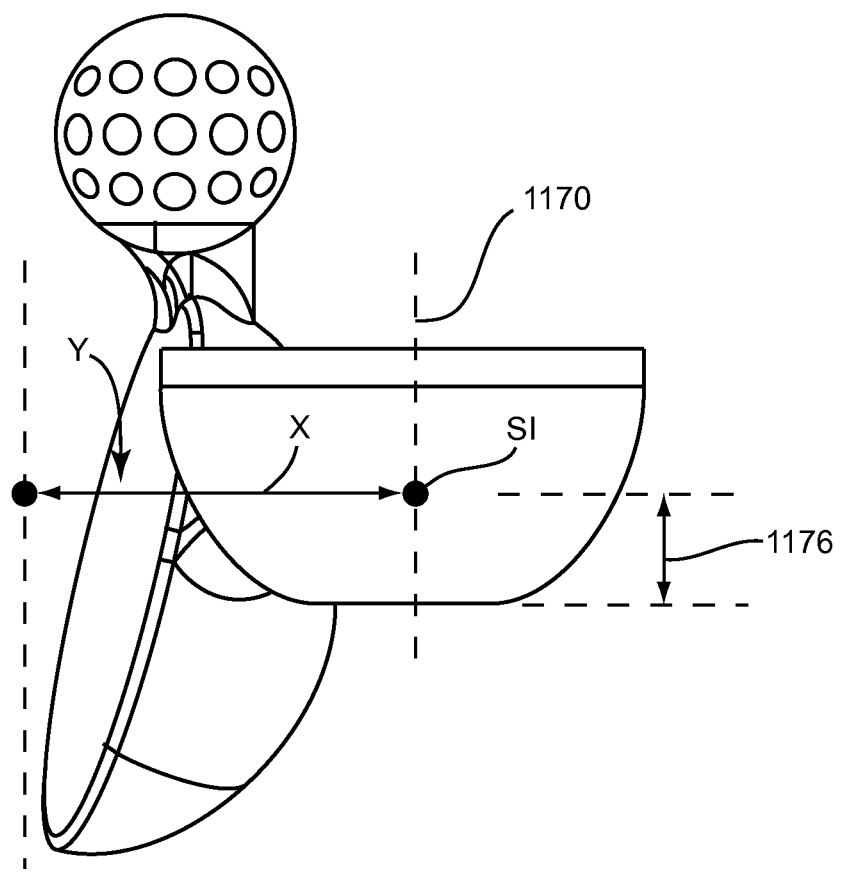
FIG. 53B is a top view of an inferior facet prosthesis according to one embodiment of the invention.
Figure 53C:
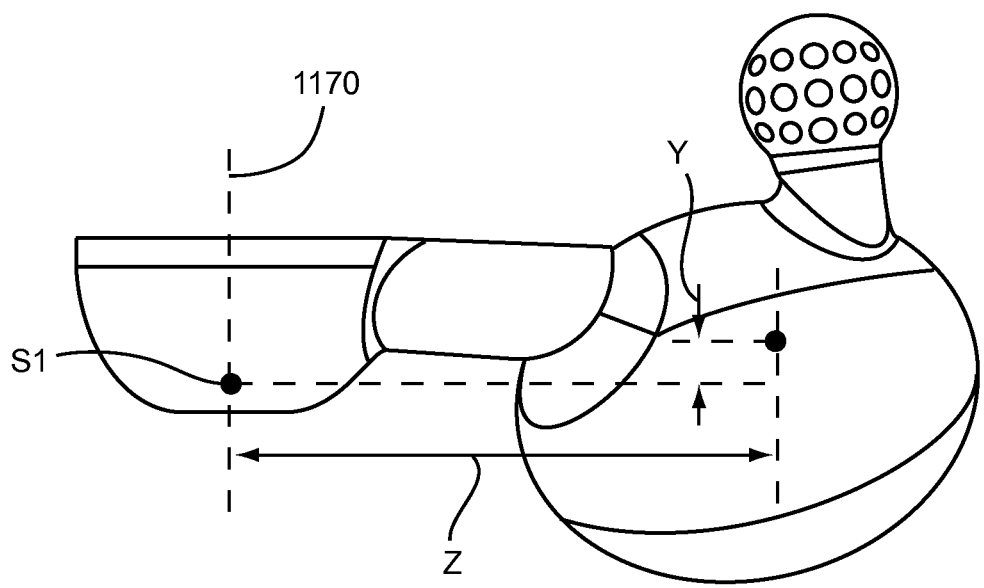
FIG. 53C is a side view of the inferior facet prosthesis of FIG. 53B.

FIGS. 53B and 53C illustrate top and side views, respectively, of an exemplary inferior facet prosthesis 1172. The inferior facet prosthesis 1172 has an x offset (X), a y offset (Y), and a z offset (Z), which are illustrated in FIGS. 53B and 53C. As shown, the offsets X, Y, and Z run between a saddle point S1 of the inferior facet prosthesis 1172 and a center point C1 of the articulation surface 1174. The saddle point S1 of FIGS. 53B and 53C is defined in a manner similar to that of the superior facet prosthesis 1100 of FIG. 51.

As shown in FIGS. 53B and 53C, the inferior facet prosthesis 1172 has a semispherical coupling portion similar to the coupling portion 1144 of the superior facet prosthesis 1100 introduced in the description of FIG. 47. Accordingly, the inferior facet prosthesis 1172 provides the same type of tri-axial pivotal motion during installation as the coupling portion 1144, as described previously. The coupling portion of the inferior facet prosthesis 1172 may also be nested in the coupling portion 1144 of the superior facet prosthesis 1100, or vice versa, to enable independent polyaxial adjustment of the prostheses 1100, 1170 when positioned in engagement with a single semispherical resection 1146.

Figure 53D:
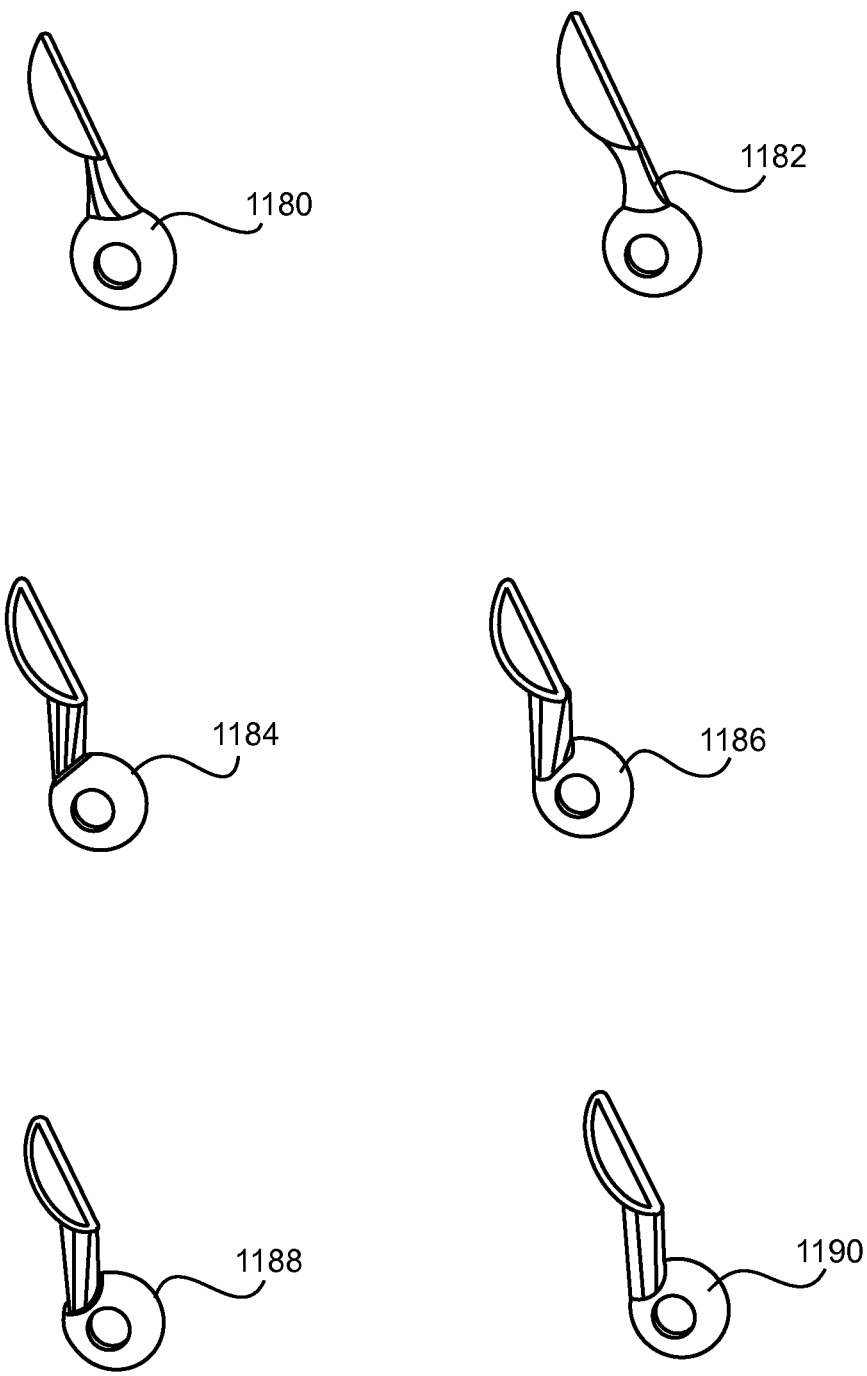
FIG. 53D is a perspective view of a plurality of inferior facet prostheses of a kit.

Referring to FIG. 53D, a perspective view illustrates a kit of left inferior facet prostheses 1180, 1182, 1184, 1186, 1188, 1190. Again, the physical dimensions can vary between the various inferior facet prostheses 1180 in the kit of FIG. 53D. These dimensions may include an inferior resection angle (I.alpha.), an inferior x offset (X), an inferior y offset (Y), an inferior facet angle (I.beta.), an inferior facet articulation radius (IR), and an inferior z offset (Z, from the center of fixation to the center of the articulation radius).

The inferior resection angle Iα is the angle of the flat resection to be made in the vertebra, for example, the vertebra 101 illustrated in some of the preceding drawings, to serve as a backing for the articulating surface of the selected inferior facet prosthesis 1180, 1182, 1184, 1186, 1188, or 1190. When measured according to the coordinate system established for the superior facet prosthesis 1100, as illustrated in FIG. 51, the inferior resection angle Iα may be approximately the same as the facet angle β for the superior prosthesis 1100 because the articulation surfaces 1122, 1174 are to be positioned generally parallel to each other. Due to the clearance between the articulating surfaces 1122, 1174 and the generally concave and convex shapes thereof, as long as the selected inferior facet prosthesis 1180, 1182, 1184, 1186, 1188, or 1190 is placed so that the articulating surfaces 1122, 1174 are generally parallel to each other, proper articulation may be expected to occur.

Thus, the inferior facet prosthesis 1180, 1182, 1184, 1186, 1188, or 1190 may be dimensioned such that Iα is nearly the same as β, and the orientation of the articulating surface 1174 may be adjusted as needed to permit the inferior facet prosthesis 1180, 1182, 1184, 1186, 1188, or 1190 to be attached to the corresponding vertebra 101. Accordingly, Iα need not be determined based on measurement of the vertebra 101, but may instead be inferred based on the selection of the superior facet prosthesis 1100, 1162, 1164, 1166, or 1168 and adjusted during installation.

The inferior facet angle Iβ may be defined as the angle of the surface to which the articulating surface 1174 is most nearly parallel. Due to the shape of the inferior facet prostheses 1180, 1182, 1184, 1186, 1188, or 1190, this angle is the same as the inferior resection angle Iα, when measured according to the coordinate system of the superior facet prosthesis 1100 of FIG. 51.

The inferior pedicle axis 1170 is the axis that is collinear with the longitudinal axis of the fixation element 1110 that is positioned through the pedicle 11 nearest to the resected inferior facet (not shown). This axis is parallel with the direction of the inferior y offset (Y). The direction of the inferior x offset (X) is perpendicular to the direction of the inferior y offset (Y). The direction of the inferior x offset (X) is generally lateral to medial with respect to the central axis of the patient's spine. The direction of the inferior y offset (Y) is generally anterior to posterior. The direction of the inferior z offset (Z) is generally cephalad to caudal.

The inferior x offset (X) for the inferior facet prosthesis 1180 can range from 0 mm to 20 mm. However, for the majority of patients, the inferior x offset (X) will range from 2 mm to 16 mm. Therefore a family of inferior facet prostheses 1180 can be provided with the inferior x offset (X) varying in increments of 2 mm. Thus, sets of inferior facet prostheses 1180 would be provided with inferior x offset (X) at 2 mm, 4 mm, 6 mm, 8 mm, 10 mm, 12 mm, 14 mm, and 16 mm to provide inferior facet prostheses 1180 that cover the statistical range for the majority of the population of patients needing inferior facet prostheses 1180.

The inferior y offset (Y) for the inferior facet prosthesis 1180 can range from −15 mm to 5 mm. However, for the majority of patients, the inferior y offset (Y) will range from −12 mm to 4 mm. Therefore a family of inferior facet prostheses 1180 can be provided with the inferior y offset (Y) varying in increments of 2 mm. Thus, sets of inferior facet prostheses 1180 would be provided with inferior y offset (Y) at −12 mm, −10 mm, −8 mm, −6 mm, −4 mm, −2 mm, 0 mm, 2 mm, and 4 mm to provide inferior facet prostheses 1180 that cover the statistical range for the majority of the population of patients needing inferior facet prostheses 1180.

The inferior facet articulation radius (IR) for the inferior facet prosthesis 1180 can range from 5 mm to 30 mm. However, for the majority of patients, the inferior facet articulation radius (IR) will range from 10 mm to 15 mm. A family of incremented inferior prostheses may be provided to cover the aforementioned range. Alternatively, the inferior facet articulation radius (IR) may be set at a given value, for example, 12 mm, and such a value may be used in substantially all cases.

The inferior z offset (Z) for the inferior facet prosthesis 1180 can range from 20 mm to 40 mm. However, for the majority of patients, the inferior z offset (Z) will range from 25 mm to 31 mm. Therefore a family of inferior facet prostheses 1180 can be provided with the inferior z offset (Z) varying in increments of 1 mm. Thus, sets of inferior facet prostheses 1180 would be provided with inferior z offset (Z) at 25 mm, 26 mm, 27 mm, 28 mm, 29 mm, 30 mm, and 31 mm to provide inferior facet prostheses 1180 that cover the statistical range for the majority of the population of patients needing inferior facet prostheses 1180.

If desired, a kit having ten left inferior facet prostheses may be assembled. Like the prostheses 1100, 1162, 1164, 1166, 1168 of the kit of FIG. 53A, the prostheses 1180, 1182, 1184, 1186, 1188, 1190 of FIG. 53D are not simply scaled up or down, but are varied according to a number of carefully selected parameters to cover the vast majority of morphologies occurring in the L4 vertebra and/or other vertebrae.

The parameters of the prostheses 1100, 1162, 1164, 1166, 1168 of FIG. 53A and/or the prostheses 1180, 1182, 1184, 1186, 1188, 1190 of FIG. 53D may include at least two dimensions that vary among the members of the kit independently of each other. Dimensions that vary independently of each other need not change according to any established relationship between the dimensions, but instead, one may change while the other remains the same between any two prostheses of the kit.

Figure 53E:
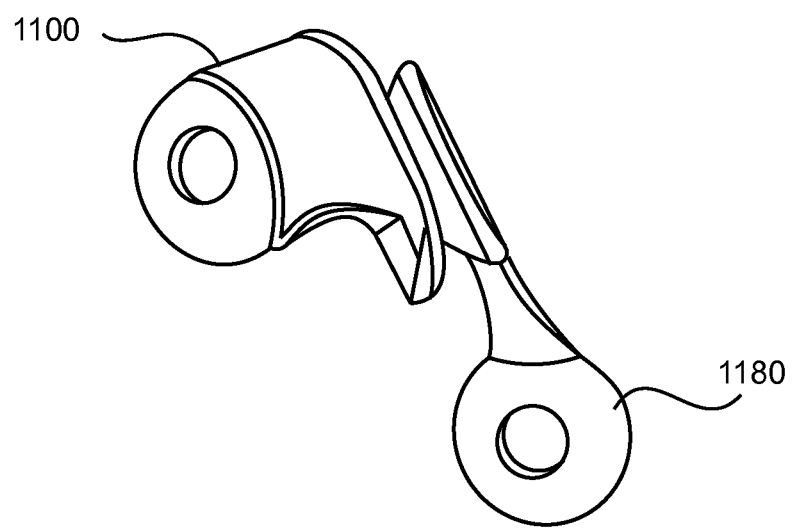
FIG. 53E is a perspective view showing how a superior facet prosthesis and an inferior facet prosthesis may fit together.

FIG. 53E is a perspective view illustrating how a superior facet prosthesis 1100 and an inferior facet prosthesis 1180 fit together. The surgeon selects an inferior facet prosthesis that, in addition to most adequately meeting the anatomy of the patient, has an articulating surface adapted for articulating with the articulating surface of the superior facet prosthesis selected.

Figure 53F:
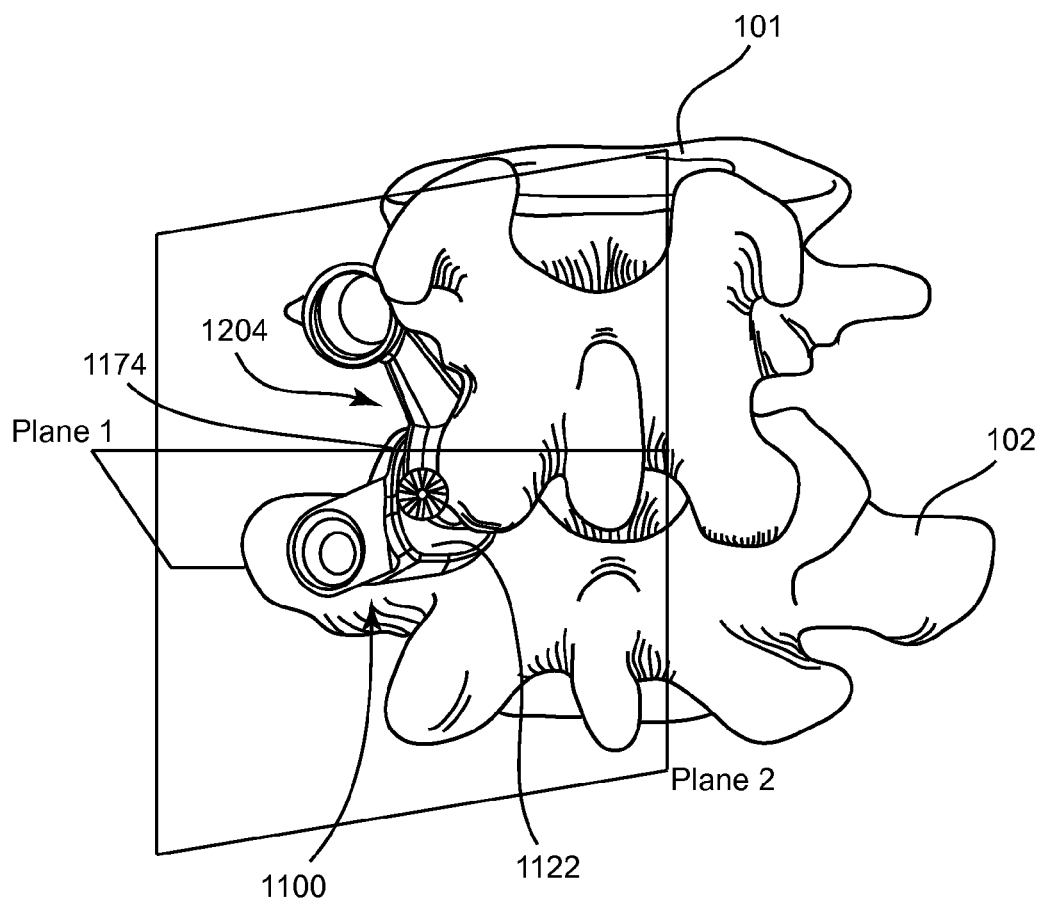
FIG. 53F is a dorsal view of an L5 superior facet prosthesis and an L4 inferior facet prosthesis fit on adjacent vertebrae to articulate against each other.

FIG. 53F is a dorsal view of a superior facet prosthesis 1100 and an inferior facet prosthesis 1204 attached to the L5 and L4 lumbar vertebrae 102, 101. In FIG. 53F, the superior facet prosthesis 1100 is attached to the left side of the L5 vertebra 102 and the inferior facet prosthesis 1204 is attached to the left L4 vertebra 101. The two prostheses 1100, 1204 are positioned on respective bone resections and oriented such that they articulate together through the range of motion naturally exhibited between the L4 and L5 vertebrae 1100, 1204. This range of motion includes flexion-extension, lateral left and right bending, torsion along a sagittal axis and combinations and coupling of all these ranges of motion.

FIG. 53F shows the prostheses 1100, 1204 and vertebrae 101, 102 in a natural position. The articulation surface 1174 of the inferior prosthesis 1204 and the articulation surface 1122 of the superior prosthesis 1100 are in contact in the neutral position. However, the prostheses 1100, 1204 are shaped to allow anatomic contact and articulation between the inferior facet articulation surface 1174 and the superior facet articulation surface 1122 throughout various anatomic ranges of motion.

Also shown in FIG. 53F are two planes labeled "Plane 1" and "Plane 2" that that intersect along an axis (not shown) that passes through the contact areas of the superior facet articulation surface 1122 and the inferior facet articulation surface 1174. Plane 1 is parallel to the page of FIG. 53F, and Plane 2 is perpendicular to the page.

Figure 53G:
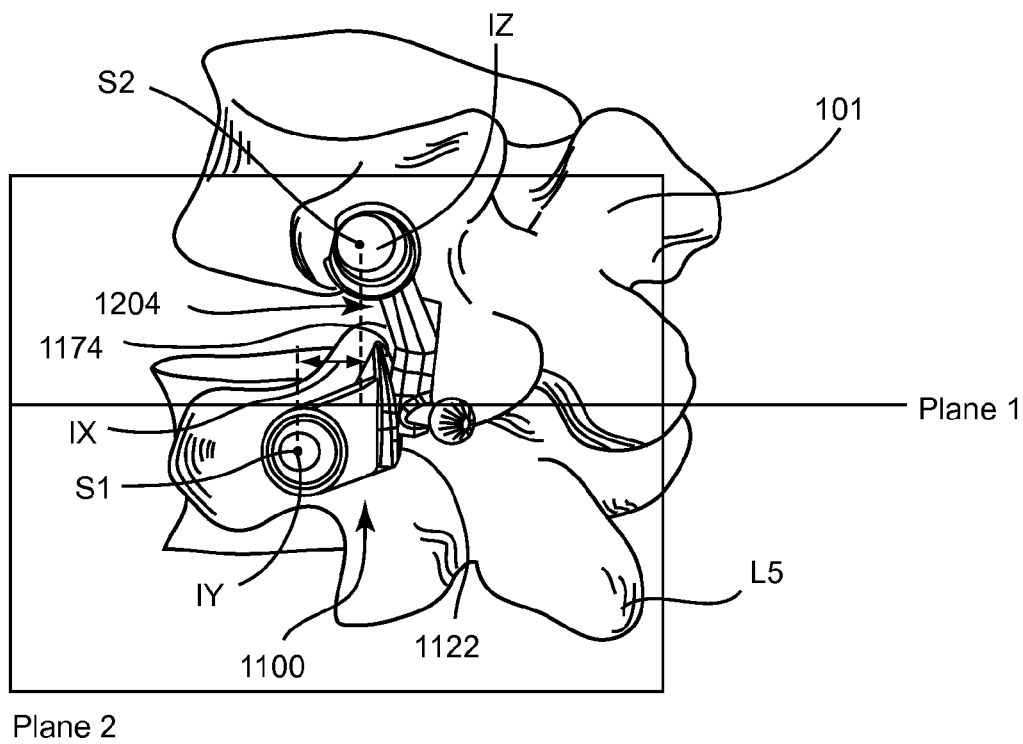
FIG. 53G is a posteriolateral view of the implants and vertebrae shown in FIG. 53F.

FIG. 53G is a posteriolaterial view of the same inferior and superior facet prostheses 1100, 1204 with the planes shown in FIG. 53F. In FIG. 53G, Plane 2 is oriented parallel to the page and plane 1 is oriented perpendicular to the page. FIG. 53G illustrates the saddle point (S1) of the vertebra 102 to which the superior facet prosthesis 1100 is coupled, and the saddle point (S2) of the vertebra 101 to which the inferior facet prosthesis 1204 is coupled. The saddle points S1, S2 are displaced from each other along an x offset (IX) parallel to the axis at which Plane 1 and Plane 2 intersect, a y offset (IY) extending perpendicular to Plane 2, or out of the page with respect to FIG. 53G, and a z offset (IZ) extending perpendicular to Plane 1. The offsets IX, IY, and IZ may be used for implant sizing and/or selection, as will be discussed subsequently.

Figure 53H:
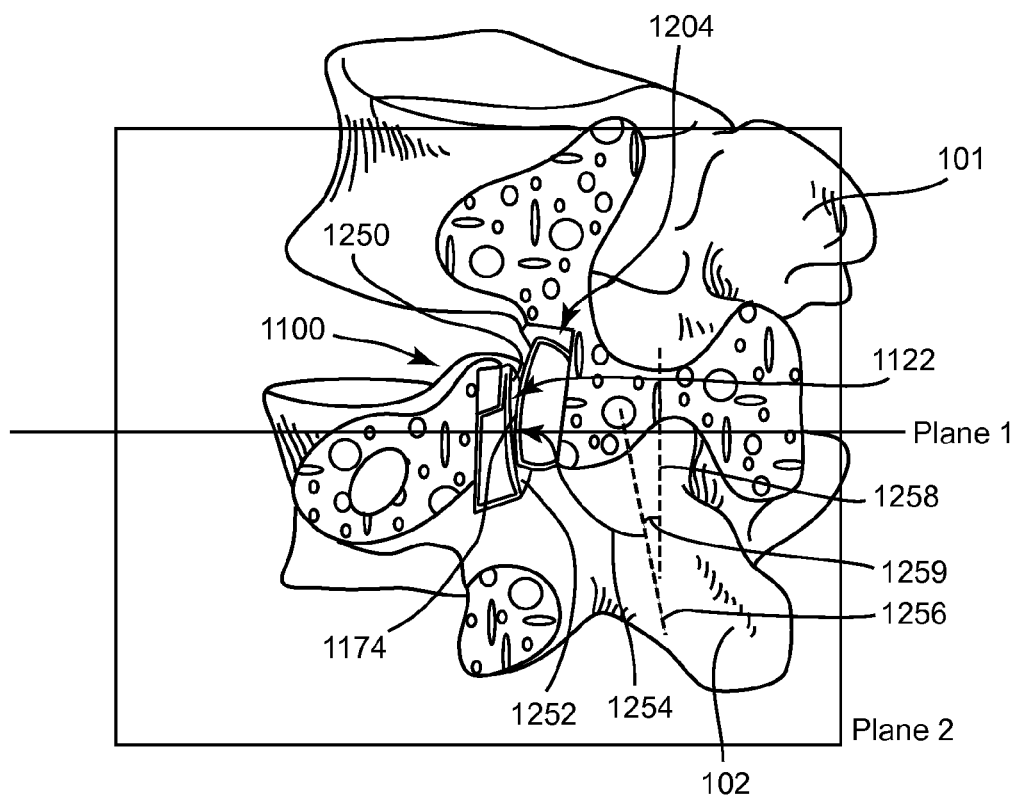
FIG. 53H is a posteriolateral view showing a cross-section along a first plane cut through the articulation of the implants of FIG. 53F.

FIG. 53H is a posteriolateral view showing a cross-section along Plane 2. This cross-section view cuts through the articulation surfaces 1122, 1174 of the prostheses 1100, 1204, thereby showing the convex shape of the inferior articulation surface 1174 against the concave shape of the superior articulation surface 1122.

FIG. 53H also illustrates the cephalad and caudal ends 1250, 1252 of the articulation surface 1122 of the superior facet prosthesis 1100. The articulation surface 1122 has a radius of curvature 1254 generally about an axis 1256. However, since the radius of curvature 1254 changes along the articulating surface 1122, the axis 1256 may be the center of curvature for only a portion of the articulation surface 1122. The radius of curvature 1254 is shown extending from the axis 1256 to the articulation surface 1122 in FIG. 53H. Furthermore, FIG. 53H illustrates a longitudinal axis 1258 of the spine in general. The axis 1256 is angled from the axis 1258 by an offset angle 1259. Since the axis 1256 and the axis 1258 may not both be precisely parallel to Plane 2, the offset angle 1259 may have a component that extends out of the page with respect to the view of FIG. 53H.

Figure 53I:
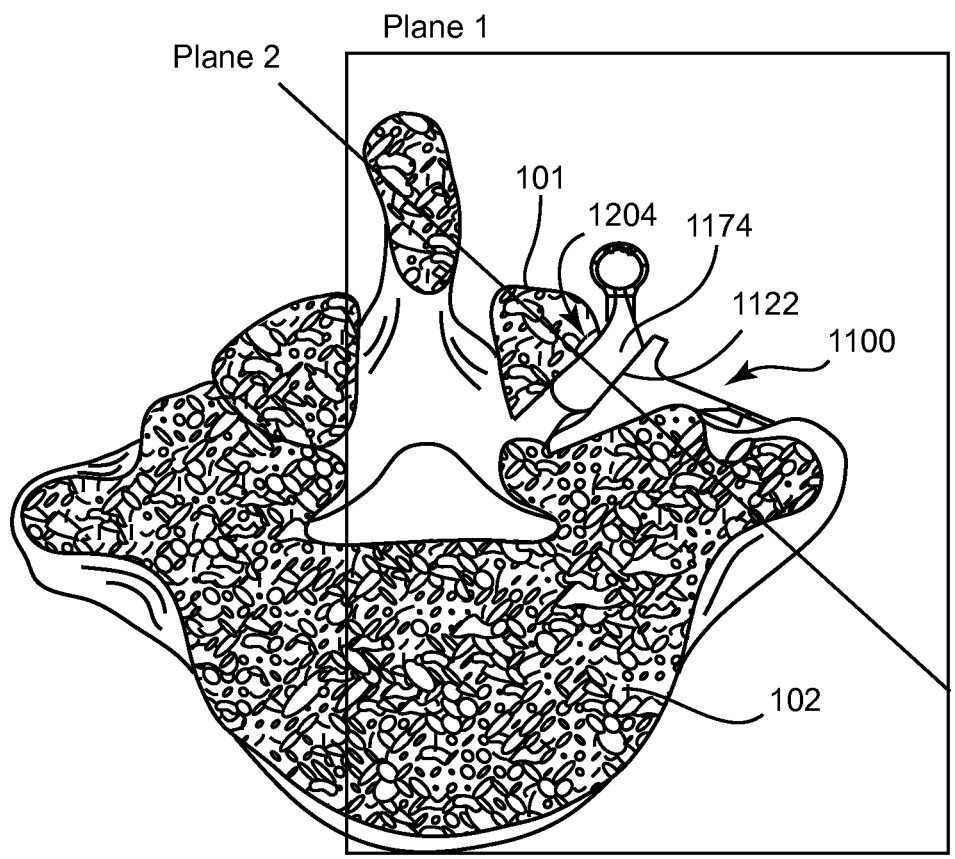
FIG. 53I is a cephalad view showing a cross-section along a second plane cut through the articulation of the implants shown in FIG. 53F.

FIG. 53I is a cephalad view showing a cross-section along Plane 1. This cross-section cuts through the articulation surfaces 1122, 1174 of the prostheses showing the convex shape of the inferior articulation surface 1174 against the concave shape of the superior articulation surface 1122. Each of the articulating surfaces 1122, 1174 has a curved shape. The articulating surfaces 1122, 1174 of the superior and inferior prostheses 1100, 1204, respectively, are shaped and relatively positioned to articulate against each other such that a medial-lateral range of relative motion between the first and second vertebrae 101, 102 increases significantly with flexion (i.e., forward bending) of the spine.

A "significant" increase in the medial-lateral range of motion refers to a difference in the range of motion that approximates the natural motion of the spine to a degree sufficient to be noticeable by the patient. More precisely, a "significant" increase may refer to the existence of at least one additional millimeter of clearance between articulating surfaces of a facet joint under flexion, as compared to the same facet joint under extension. Furthermore, a "significant" increase in the medial-lateral range of motion may refer to the existence of two additional millimeters of clearance between the articulating surfaces.

As shown in FIG. 53H, one of the articulating surfaces 1122, 1174, for example, the articulating surface 1122 of the superior facet prosthesis 1100, has a cephalad end 1250 and a caudal end 1252. The articulating surface 1122 also has a radius of curvature 1254 about an axis 1256 extending generally from the cephalad end 1250 end to the caudal end 1252. The radius of curvature 1254 changes along the axis 1256 to provide greater clearance between the articulating surfaces 1122, 1174 when the spine is under flexion. Similarly, the changing radius of curvature 1254 provides less clearance between the articulating surfaces 1122, 1174 when the spine is extended.

In this embodiment, the articulating surface 1122 is shaped such that, when the superior facet prosthesis 1100 is coupled to the vertebra, the axis 1256 is significantly anteriorly inclined at the cephalad end 1250 to provide greater clearance between the articulating surfaces 1122, 1174 when the spine is under flexion. In addition to or in the alternative to variation of the radius of curvature 1254 from the cephalad end 1250 to the caudal end 1252, the radius of curvature 1254 could vary along a medial-lateral direction of the articulating surface.

More precisely, with brief reference to FIG. 51 again, the radius of curvature may be larger toward a medial end 1260 and a lateral end 1262 of the articulating surface 1122 than at a central portion 1264 thereof. The radius of curvature could also be substantially infinite toward the medial and lateral ends, such that the articulating surface of the superior prosthesis has a curved region 1268 proximate the central portion 1264, a first tangent flat 1270 disposed medially of and tangent to the curved region 1268, and a second tangent flat 1272 disposed laterally of and tangent to the curved region 1268.

If desired, the inferior facet prosthesis may have an articulating surface with a three-dimensionally curved, generally elliptical shape. A three-dimensionally curved, generally elliptical shape may have the appearance of a stretched spheroid or the like. Accordingly, a three-dimensionally curved, generally elliptical shape has a first cross section having a generally elliptical shape and a second cross section perpendicular to the first cross section, having a semicircular shape. Alternatively, an inferior facet prosthesis may have an articulating surface with a generally cylindrical or semispherical shape, as illustrated in connection with FIGS. 40, 53B, and 53C, for example.

According to one alternative embodiment, the articulating surface of the superior facet prosthesis may have a uniform, substantially unchanging radius of curvature. The relative medial-lateral motion between the vertebra and the adjacent vertebra may still increase significantly with flexion of the spine due to the curvature of the inferior facet prosthesis. The radius of curvature of the articulating surface of the inferior facet prosthesis may change along an axis thereof, either along the cephalad-caudal direction or along the medial-lateral direction, to provide greater clearance between the articulating surfaces when the spine is under flexion. According to yet another alternative, the variation in motion in the medial-lateral direction may be obtained, not through a variable radius of curvature, but rather, through the relative positioning of the superior and inferior facet prostheses.

Returning to FIGS. 53F, 53G, 53H, and 53I, the materials used to construct the articulating surfaces of the prostheses 1100, 1174 may be selected from a group consisting of a polymeric material, a polymeric bearing material attached to a metal substrate, a ceramic bearing material, a metal bearing material, and combinations thereof. A variety of surface coatings, treatments, and the like may be used to enhance the performance and/or longevity of the prostheses 1100, 1174.

The superior facet prosthesis 1100 may be shaped such that, when the superior facet prosthesis 1100 is coupled to the vertebra 102, the axis 1256 is significantly anteriorly inclined from a longitudinal axis (not shown) of the spine to provide greater clearance between the articulating surfaces 1122, 1174 when the spine is under flexion. In this application, "significantly anteriorly inclined" refers to the presence of a deliberate offset, from the longitudinal axis of the spine, that has a meaningful effect on the facet joint of which the corresponding prosthesis is a part. The offset angle 1259 between the axis 1256 and the longitudinal axis 1258 of the spine may range from about −2.5° to about 14.5°. More precisely, the offset angle 1259 may range from about 5° to about 10°. Yet more precisely, the offset angle 1259 may be about 7.25°.

Referring briefly again to FIG. 51 and FIG. 53G, one method of selecting inferior and superior facet prosthesis will be described. The appropriate prosthesis of the kit of superior facet prostheses may be selected by, for example, forming a semicircular resection centered at a position along the pedicle axis 1170 of the vertebra 102, at a known displacement from the saddle point S1. Certain offsets, such as $X_{1\ and\ X2}$, as shown in FIG. 51, may be measured with between the saddle point S1 and the most medial and anterior point P1.

Based on $X_1$ and $X_2$, values of the resection angle α and the facet angle β may be obtained. The values of α and β may be used to select the appropriate superior facet prosthesis of the kit by, for example, looking up the values of α and β on a lookup table or the like. The remaining dimensions of the selected superior facet prosthesis may thus be determined based on the combination of α and β.

The appropriate prosthesis of the kit of inferior facet prostheses may also be selected by making a limited number of measurements. More precisely, a semicircular resection may be formed at a position centered along the pedicle axis of the vertebra 101, at a known displacement from the saddle point S2. One or more of the offsets IX, IY, and IZ may be measured between the resections of the saddle points S1 and S2.

Based on the values of IX, IY, and/or IZ obtained, the values of Iα and Z (as illustrated in FIG. 53C) are determined. The values of Iα and Z may be used to select the appropriate inferior facet prosthesis of the kit by, for example, looking up the values of Iα and Z on a lookup table or the like. The remaining dimensions of the selected inferior facet prosthesis may thus be determined based on the combination of Iα and Z.

The above-described selection method is beneficial because a relatively small number of linear measurements may be made to determine which set of prostheses is most appropriate for a given patient. Ease of measurement is important because the measurements must generally be performed during surgery. Accordingly, easier, more rapid measurements enable surgery to be more rapidly and safely carried out. In alternative embodiments, different measurement schemes may be carried out, and may include different linear measurements, angular measurements, and the like. In this application, measuring the "relative positions" of bony landmarks may include measurement of linear displacements, angular displacements, or any combination thereof.

In alternative embodiments, a kit of superior and/or inferior prosthesis need not have multiple one-piece prostheses, but may instead have multiple components designed to be assembled together to provide a prosthesis having the necessary parameters. For example, each of a plurality of semispherical bone contacting portions may be connectable to any of a plurality of articulating surfaces, via a plurality of connecting members. Selecting a prosthesis may then entail selecting a bone contacting portion, an articulating surface, and a connecting member. The bone contacting portion, articulating surface, and connecting member may then be coupled together via set screws, adhesives, interference fits, or the like.

If desired, the manner in which the various components are attached together may also be adjustable to enable further adjustability of the dimensions of a selected prosthesis. Such a kit of components may also include additional components such as bearing surfaces, as described in connection with FIG. 16. As yet another alternative, a single prosthesis may be adjustably deformed, for example, through the use of a lever-operated manual press, a hydraulic press, or the like, to provide the desired dimensions prior to attachment to a patient's vertebra.

After a semispherical resection 1146 has been formed in a vertebra and the corresponding prosthesis has been selected, a flat resection, such as the first resection surface 1112 of FIG. 48, may be formed. The flat resection may be contiguous with the semispherical resection 1146, or may be separated from the semispherical resection 1146 by an expanse of unresected bone. The determination of which prosthesis to use may also indicate to the surgeon the proper placement of the flat resection to properly receive the selected prosthesis. After the flat resection has been formed, the selected prosthesis may be attached to the vertebra. The procedure may be the same as or similar to that described above for installation of the inferior and superior facet prostheses.

Figure 54:
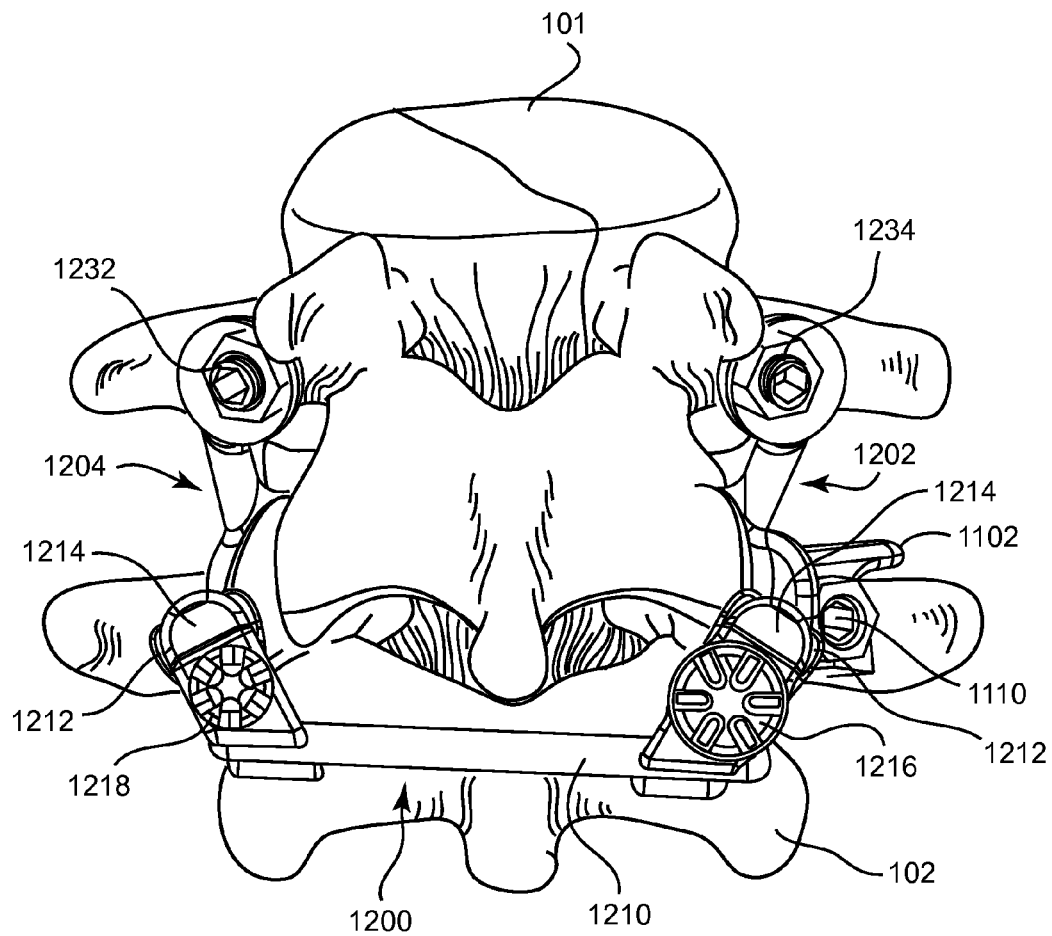
FIG. 54 is a dorsal view of a bilateral inferior facet prosthesis system and a superior facet prosthesis in situ.

FIG. 54 is a dorsal view of a bilateral inferior facet prosthesis system 1200 in situ. The bilateral inferior facet prosthesis system 1200 is a multi-piece inferior and superior facet prosthesis that has both a right inferior facet prosthesis 1202 and a left inferior facet prosthesis 1204 connected by a crosslink, which may take the form of a stabilizing bar 1210. Both the right inferior facet prosthesis 1202 and the left inferior facet prosthesis 1204 are designed to be affixed to the top vertebra 101 at the respective inferior facet resection surfaces 121 (FIG. 19).

The bilateral inferior facet prostheses 1202, 1204 allow replacement of both the left and the right inferior facets. In this embodiment, the inferior prostheses are placed over left and right fixation elements 1232, 1234 that extend into the top vertebra 101. In the embodiment shown in FIG. 54, the right inferior side is articulating against a right superior facet prosthesis 1102 attached to the first resection surface 1112 (FIG. 49) on the right pedicle 11 of the bottom vertebra 102. Also in this embodiment, the left inferior facet prosthesis 1204 is articulating against the left natural superior facet of the bottom vertebra 102.

The stabilizing bar 1210 of the bilateral inferior prosthesis system 1200 is designed to stabilize the left inferior facet prosthesis 1204 and the right inferior facet prosthesis 1202 so that they are secure. The stabilizing bar 1210 also allows the left and right inferior facet prostheses 1204, 1202 to support each other rather than requiring stabilizing members to be coupled to the spine lamina or the resected inferior facet tissue. Further, the stabilizing bar 1210 can compress the left and right inferior facet prostheses 1202, 1204 against the resected bone to improve bony ingrowth and apposition.

As also shown in FIG. 54, the stabilizing bar 1210 is coupled to the left and right inferior prostheses 1202, 1204 by a gripping mechanism. The gripping mechanism may include any of a variety of structures, including clips, clamps, adhesive-bonds, threaded fasteners, and the like. In the embodiment of FIG. 54, the gripping mechanism includes fore and aft flanges 1212, 1214 that engage the stabilizing bar 1210 to form a groove-and-rod joint. The fore and aft flanges 1212, 1214 are compressed together with threaded turnbuckles 1216, 1218 to pinch the stabilizing bar 1210 there between.

The pinching action of the flanges 1212, 1214 allows the distance between the left and right inferior prostheses 1202, 1204 to be adjusted to best suit the anatomy of the patient. During surgery, the surgeon would use a tool (not shown) to compress the left and right inferior prostheses 1202, 1204 to the desired positions and then tighten the turnbuckles 1216, 1218 to secure the stabilizing bar 1210.

Figure 55:
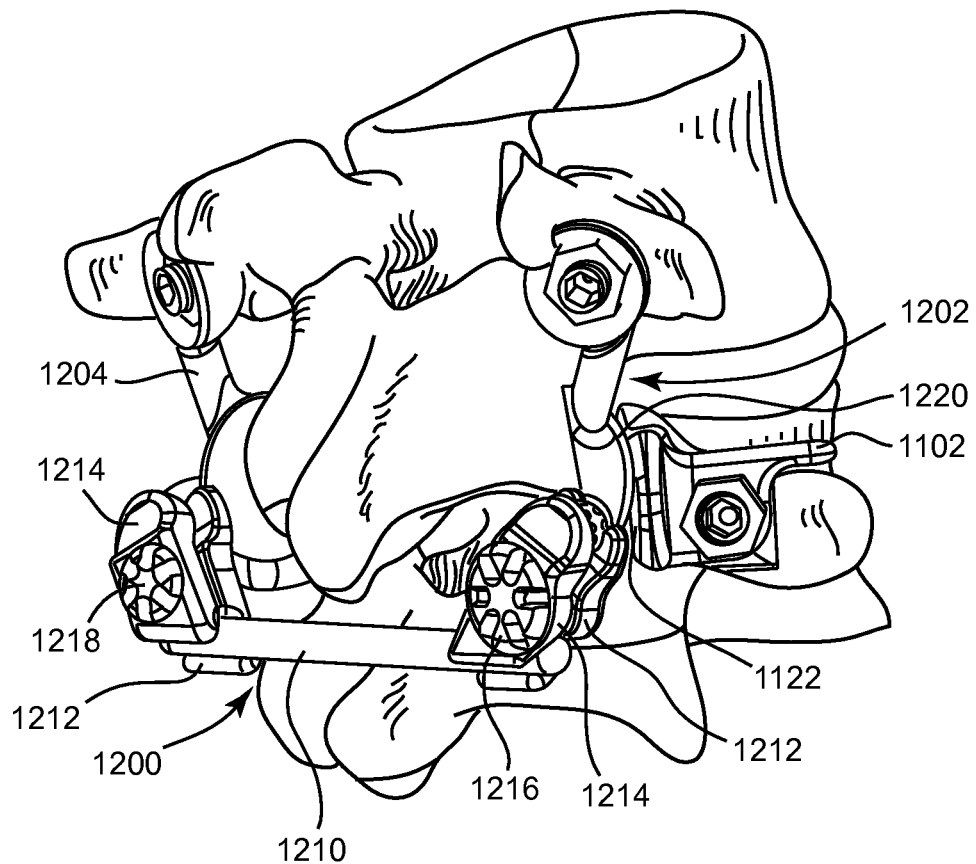
FIG. 55 is a perspective view of the bilateral inferior facet prosthesis system and the superior facet prosthesis of FIG. 54.

FIG. 55 is a perspective view of the bilateral inferior facet prosthesis system 1200. The right inferior facet prosthesis 1202 includes a convex articulating surface 1220 that engages an articulating surface 1122 of the right superior facet prosthesis 1102. In one embodiment, the articulating surface 1122 of the right superior facet prosthesis 1102 has a concave shape (FIGS. 47, 51).

In this application, the term "convex" relates to a surface that bulges outward with a three-dimensional curvature. Accordingly, a convex surface is not just a sectorial portion of a cylinder, but rather, has some outward curvature along two perpendicular directions. A convex surface may be "semispherical," or in other words, may include some sectorial portion of a sphere, which may be less than a hemisphere. However, a convex surface need not be semispherical, but may instead have contouring that provides a portion of an oval, elliptical, parabolic, and/or irregular cross sectional shape. A convex surface also need not be curved in whole or in part, but may instead have one or more planar portions.

In this application, "concave" refers to a surface with a central portion that is recessed with respect to at least two peripheral portions positioned on either side of the central portion. A concave surface may be formed by planar regions, curves, or combinations thereof. The central portion may be recessed along only one dimension, as with a surface defined by an interior section of a cylindrical wall. Alternatively, the central portion may be recessed along two perpendicular dimensions, so that the central portion is recessed with respect to at least four peripheral portions arranged around the central portion. Accordingly, the surface may include a semispherical section, a three-dimensional parabolic or ellipsoidal section, or any other three-dimensionally curved shape.

As another alternative, the central portion of a concave surface may be recessed along one direction and distended with respect to a perpendicular direction, so that the concave surface takes on a shape similar to that of the rounded groove of a pulley that is designed to receive a rope. Like a convex surface, a concave surface need not be curved in whole or in part, but may instead have one or more planar portions.

Figure 56:
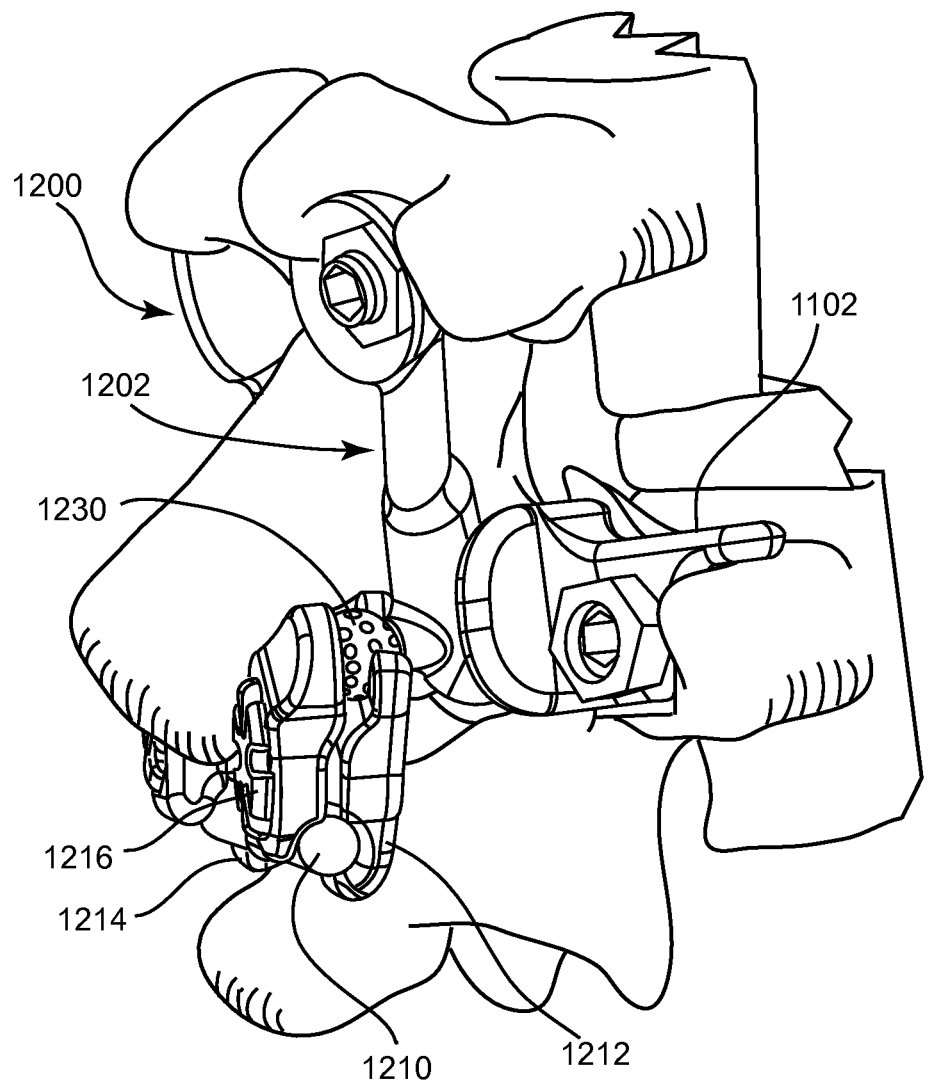
FIG. 56 is a lateral view of the bilateral inferior facet prosthesis system and superior facet prosthesis in situ.

FIG. 56 is a lateral view of the bilateral inferior facet prosthesis system 1200 and right superior facet prosthesis 1102. The right inferior prosthesis 1202 includes a member 1230 upon which the flanges 1212, 1214 clamp. In the embodiment shown, the member 1230 is a ball-shaped member 1230 upon which the flanges 1212, 1214 clamp to form a ball-and-socket joint. The ball-and-socket joint and groove-and-rod joint provide multiple degrees of freedom for variable positioning of the left and right inferior prostheses 1202, 1204. More precisely, the ball-and socket joint enables triaxial rotation, i.e., rotation about three perpendicular axes, until the flanges 1212, 1214 are pressed about the member 1230 to resist further relative rotation.

The ball-and-socket joint enables relative motion between the inferior prostheses 1202, 1204 along the anterior/posterior directions and along the cephalad/caudal directions. The groove-and-rod joint enables relative motion between the inferior prostheses 1202, 1204 along the lateral/medial directions. However, when the turnbuckles 1216, 1218 are tightened, the displacement between the ball-shaped members 1230 of the inferior prostheses 1202, 1204 becomes fixed, and the ball-shaped members 1230 are no longer freely pivotable with respect to the flanges 1212, 1214. Thus, the relative positions and orientations of the inferior prostheses 1202, 1204 may be fixed by tightening the turnbuckles 1216, 1218.

An alternative embodiment replaces the ball shaped member 1230 with a member (not shown) of differing shape and flanges adapted to engage the alternative member. Other potential shapes that allow a range of adjustability and movement between the left and right inferior prostheses 1202, 1204 and the flanges 1212, 1214 prior to clamping include, but are not limited to, columnar and annular shapes.

The ball-shaped member 1230 shown in FIG. 56 has several divots formed thereon. Upon compression of the flanges 1212, 1214, the flanges deform into the divots to provide enhanced coupling and resistance to slippage therebetween. An alternative embodiment of the ball-shaped member 1230 has circumferential or axial splines (FIG. 63) formed thereon, which "bite" into the flanges 1212, 1214. Other alternative surface features of the ball-shaped member 1230 include knurling, nubs, grooves, facets, and combinations of any of the above.

Similarly, the stabilizing bar 1210 can have surface features to enhance coupling to the flanges 1212, 1214. Exemplary surface features include longitudinal splines, knurling, divots, nubs, and grooves. Splines prevent rotation of the stabilizing bar 1210 with respect to the flanges 1212, 1214. Knurling advantageously prevents both rotation and translation of the stabilizing bar 1210 with respect to the flanges 1212, 1214.

The flanges 1212, 1214 can be formed of a material softer than that of the stabilizing bar 1210 and the ball-shaped members 1230 to further enhance coupling. Illustrative materials for the stabilizing bar 1210 and ball-shaped members 1230 are Cobalt-Chrome (Co—Cr) alloys, Titanium (Ti) and stainless steel alloys. However, other biocompatible materials such as rigid polymers including PEEK and PEAK can be formed into the shapes of the stabilization bar 1210, and/or the ball-shaped members 1230. In one alternative embodiment, the flanges 1212, 1214 are formed integrally with or rigidly attached to the left and right inferior prostheses 1202, 1204.

Referring again to FIG. 54, ends of the flanges 1212, 1214 that engage the stabilizing bar 1210 are angled towards each other. This angling avoids interference with surrounding bone and avoids interference with the superior facet or the right superior facet prosthesis 1102.

With continued reference to FIG. 54, it is seen that the heads of the turnbuckles 1216, 1218 can vary in size. As shown, the turnbuckle 1216 is larger than the turnbuckle 1218. The larger head of the turnbuckle 1216 allows the surgeon to exert more torque on the turnbuckle 1216, thereby allowing a more secure coupling of the flanges 1212, 1214 to the stabilizing bar 1210. The smaller head of the turnbuckle 1218 requires less space at the surgical site of the patient than the larger head of the turnbuckle 1216. Therefore, the surgeon can select a turnbuckle head having the desired size, weighing the benefits of more applied torque of the larger head with the reduced spatial requirements of the smaller head.

An alternative embodiment replaces the stabilizing bar 1210 with a flexible link, such as a cable of a biocompatible material. Yet another alternative embodiment includes a stabilizing bar having threaded ends. Instead of pinching flanges, the threaded ends of the stabilizing bar extend through flanges of the left and right inferior prostheses 1202, 1204. Threaded fasteners engage the threaded ends of the stabilizing bar. The threaded fasteners are then tightened to provide the desired positioning of the left and right inferior prostheses 1202, 1204. In another variation, the stabilizing bar is rotated such that the threads of the stabilizing bar engage fixed threaded portions of the flanges.

Figure 57:
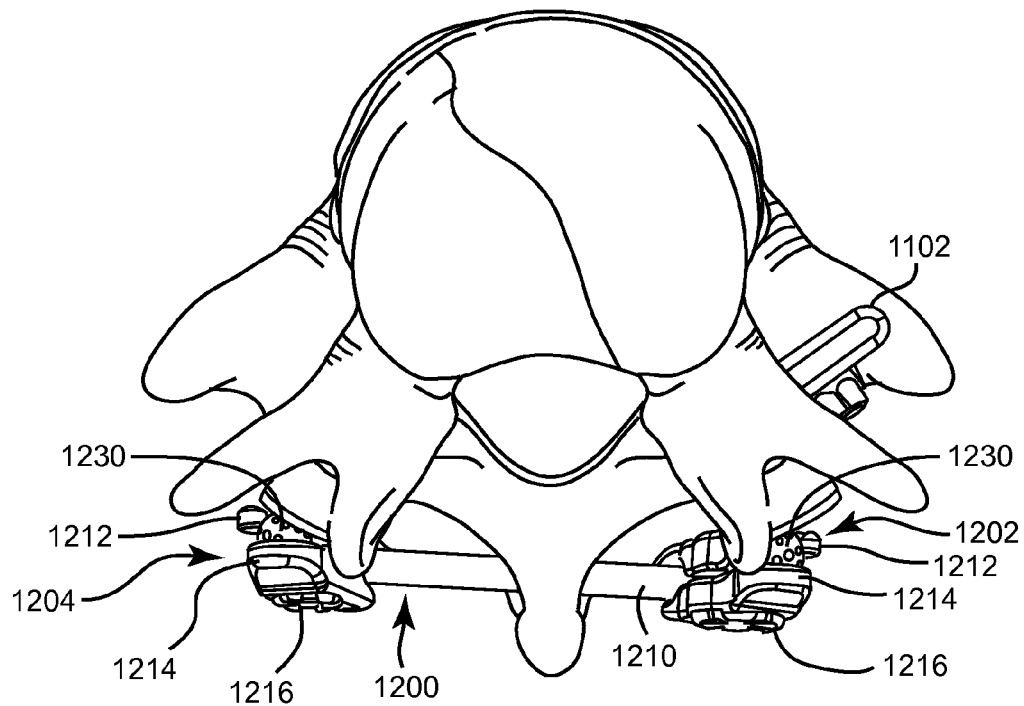
FIG. 57 is a cranial view of the bilateral inferior implant system in situ.

FIG. 57 is a cranial view of the bilateral inferior facet prosthesis system 1200.

Figure 58:
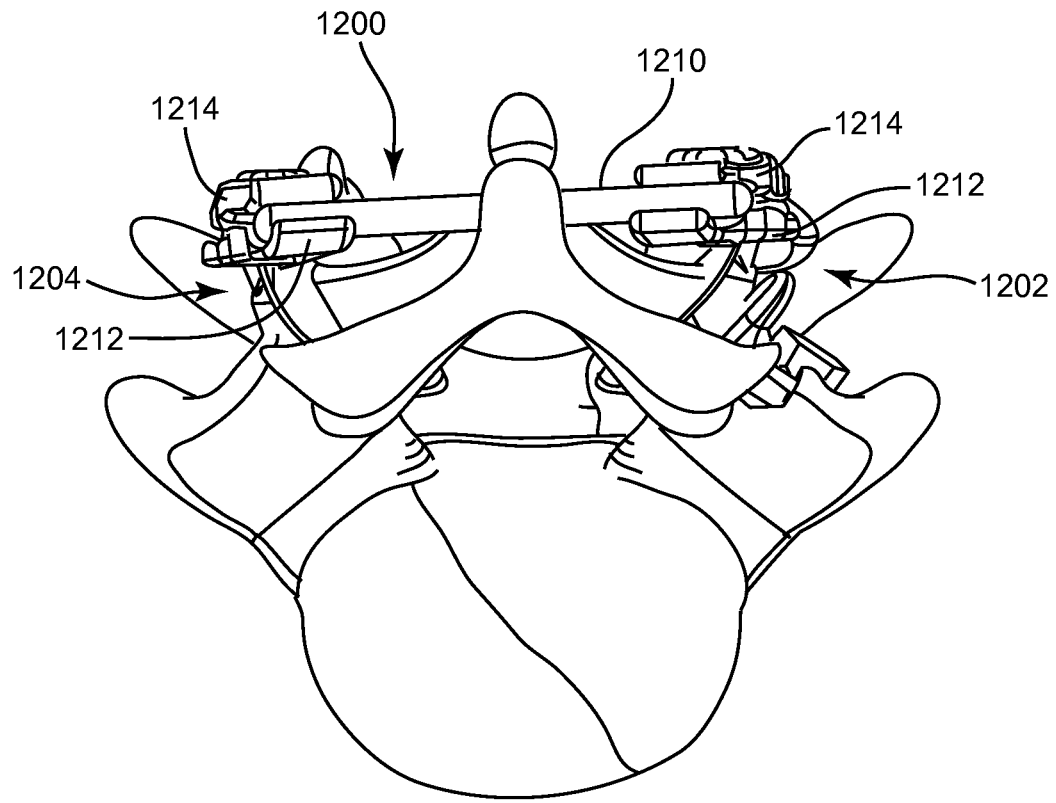
FIG. 58 is a bottom view of the bilateral inferior facet prosthesis system in situ.

FIG. 58 is a bottom in situ view of the bilateral inferior facet prosthesis system 1200 in situ.

Figure 59:
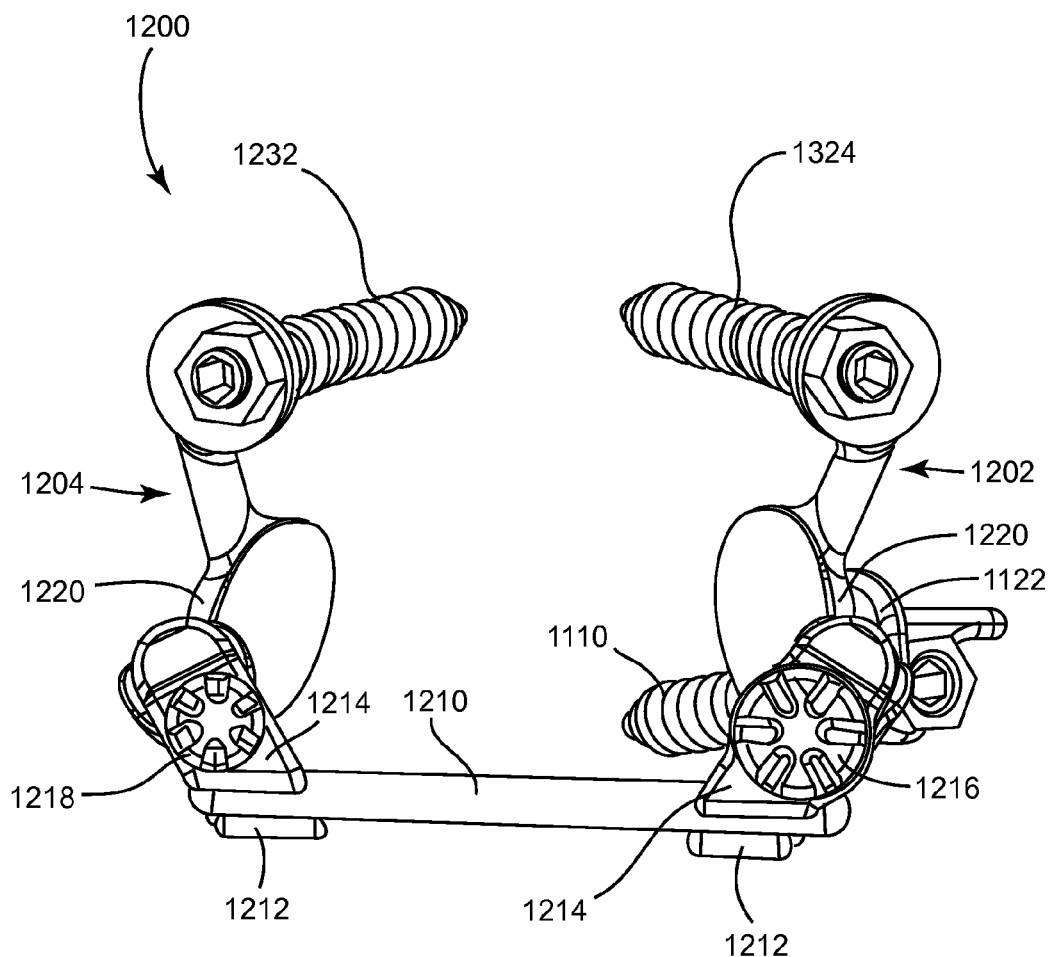
FIG. 59 is rear view of the bilateral inferior facet prosthesis system in isolation.

FIG. 59 is rear view of the bilateral inferior facet prosthesis system 1200 in isolation.

Figure 60:
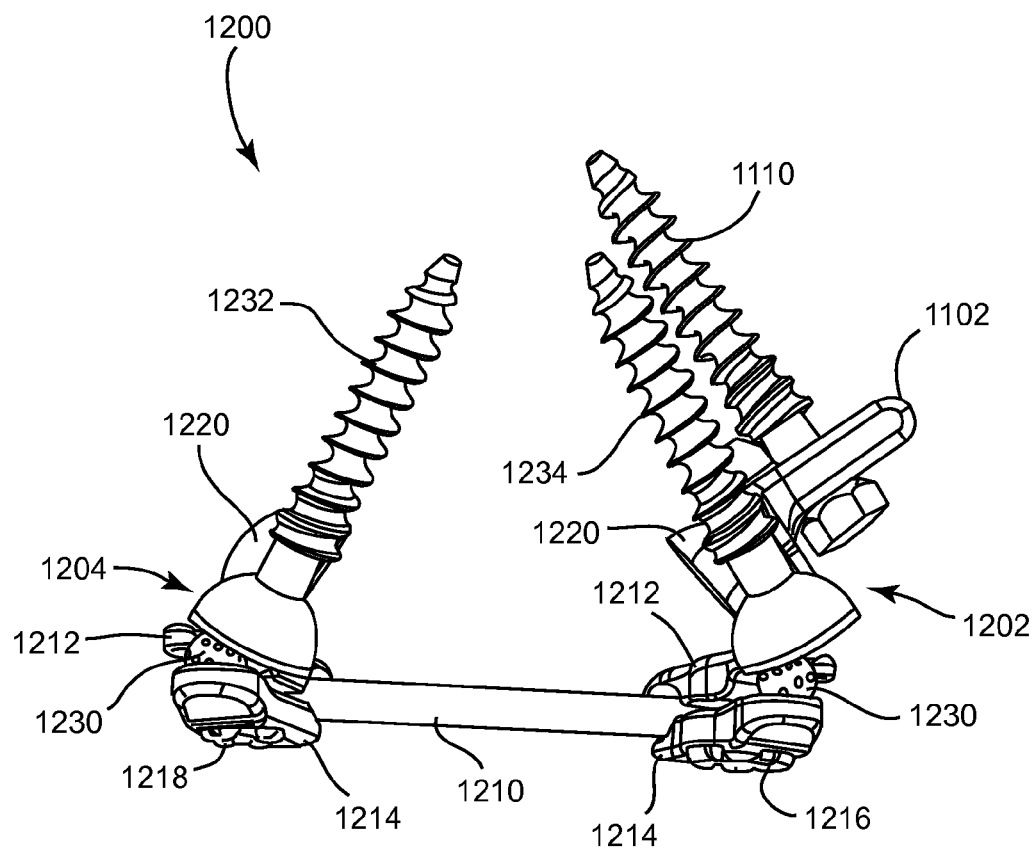
FIG. 60 is a top view of the bilateral inferior facet prosthesis system in isolation.

FIG. 60 is a top view of the bilateral inferior facet prosthesis system 1200.

Figure 61:
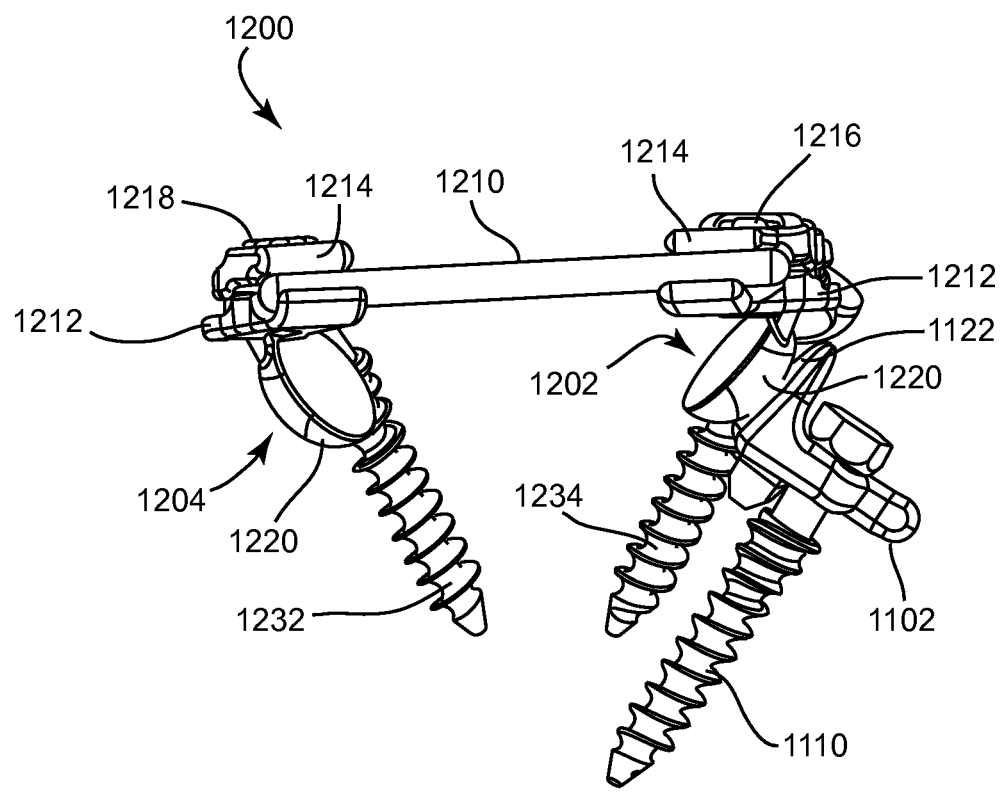
FIG. 61 is a bottom view of the bilateral inferior facet prosthesis system in isolation.

FIG. 61 is a bottom view of the bilateral inferior facet prosthesis system 1200.

Figure 62:
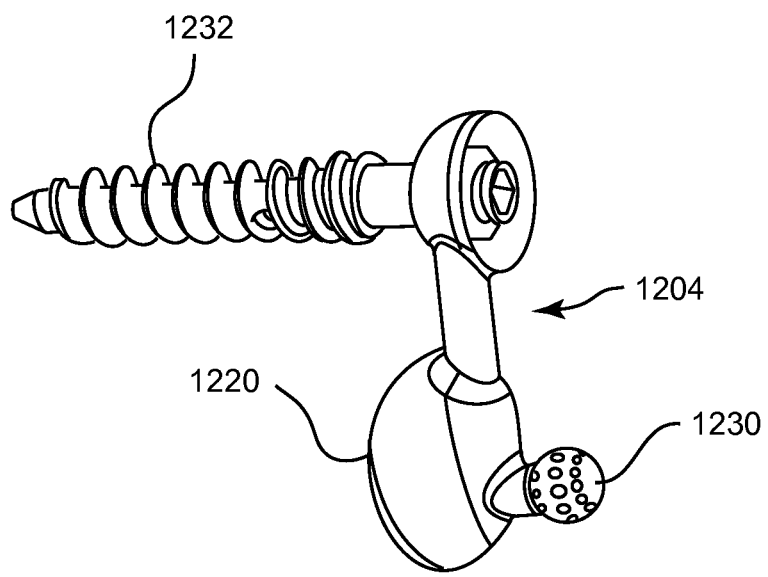
FIG. 62 is a perspective view of the right inferior prosthesis.

FIG. 62 is a perspective view of the right inferior prosthesis 1204.

Figure 63:
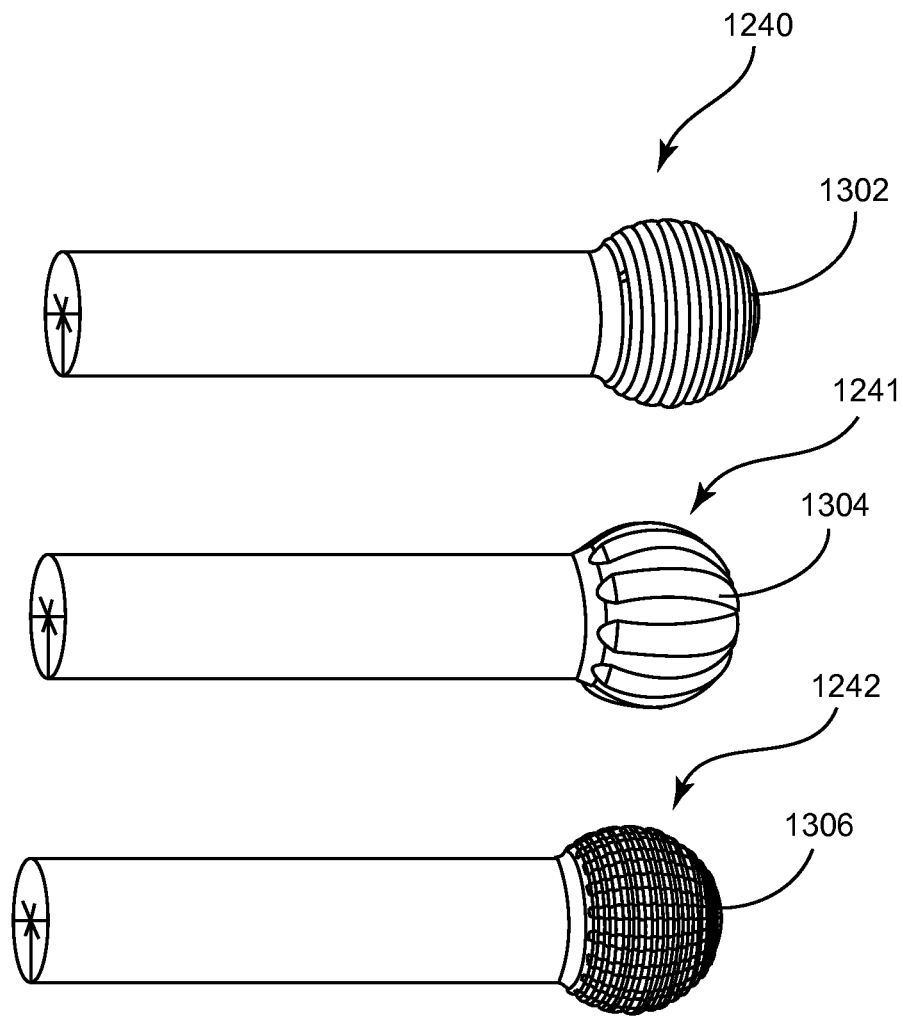
FIG. 63 is a perspective view of various ball-shaped members of inferior prostheses, the ball-shaped members having differing surface features, particularly circumferential grooves, longitudinal grooves, and knurling.
Figure 64:
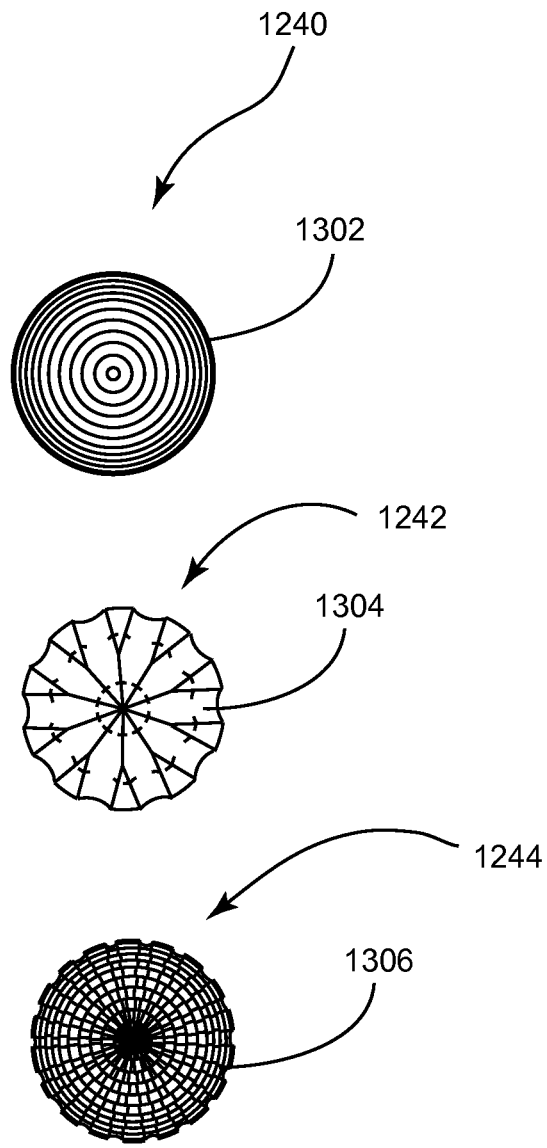
FIG. 64 is an end view of the ball-shaped members of FIG. 63.

FIGS. 63 and 64 are perspective and end views, respectively, of various ball-shaped members 1240, 1242, 1244 that may be included in the inferior prostheses 1202, 1204 in place of the members 1230, the ball-shaped members 1240, 1242, 1244 having differing surface features, particularly circumferential grooves 1302, longitudinal grooves 1304, and knurling 1306.

Figure 65:
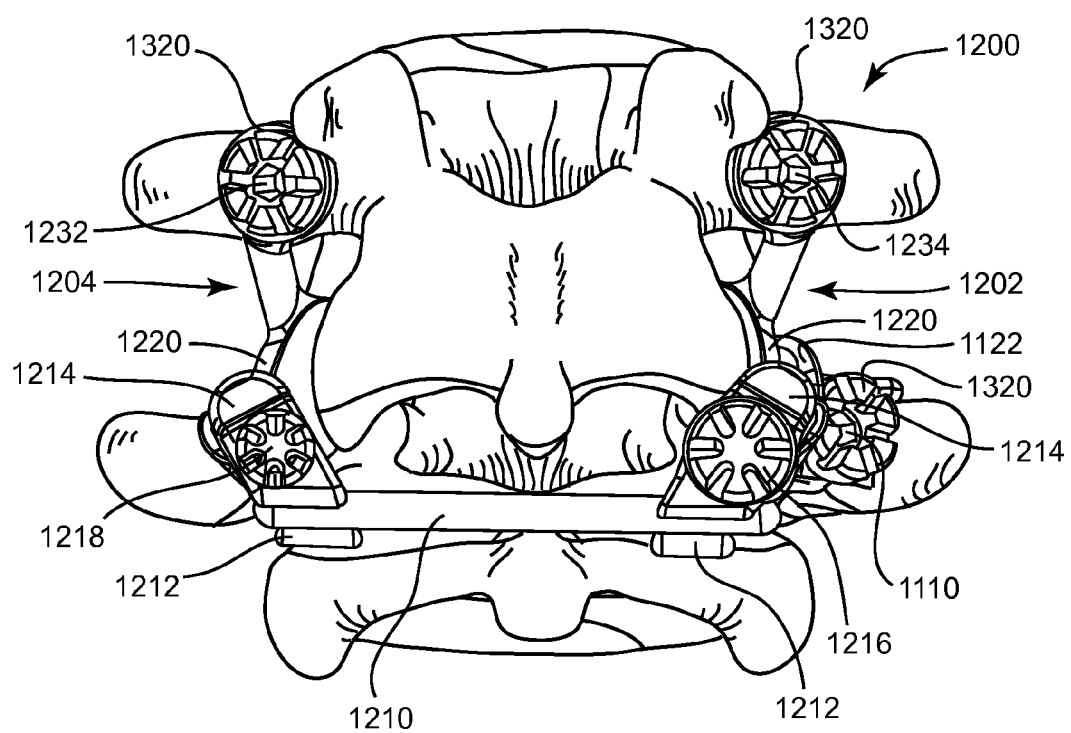
FIG. 65 is a dorsal view of the bilateral inferior facet prosthesis system, in which castle nuts are attached to the left and right fixation elements.

FIG. 65 is a dorsal view of the bilateral inferior facet prosthesis system 1200, in which castle nuts 1320 are attached to the left and right fixation elements 1232, 1234 and to the fixation member 1110.

While various embodiments have been described above, it should be understood that they have been presented by way of example only, and not by way of limitation. Thus, the breadth and scope of the invention should not be limited by any of the above-described exemplary embodiments, but should be defined only in accordance with the following claims and their equivalents.

The invention claimed is:

1. A spinal implant kit for replacing at least one removed facet of a resected vertebra, wherein the resected vertebra has a pedicle saddle point (S1) defining an intersection between a posterior pedicle bone surface and a longitudinal axis of the pedicle wherein the at least one removed facet is a natural right superior facet, a natural left superior facet, a natural right inferior facet, or a natural left inferior facet, wherein the at least one removed facet has an articulating surface that, prior to removal of the at least one removed facet has a most medial and anterior point (P1), the spinal implant kit comprising:

a plurality of fixation elements; and
a plurality of components for replacing a first facet of the at least one removed facet, wherein the components have the same parametric features characterized by a first dimension and a second dimension;
wherein each of the components is of monolithic construction and comprises a generally convex semispherical surface, wherein the first and second dimensions vary in magnitude disproportionately relative to each other among the components such that a subset of the components is selectable to provide a selected prosthesis dimensioned to match a morphology of the resected vertebra;
wherein a subset of the fixation elements is selectable to attach the selected prosthesis to the resected vertebra,
wherein the selected prosthesis comprises:
an articulating surface positioned to approximate an original position of the first facet when the selected prosthesis is attached to the resected vertebra; and
a bone apposition surface to abut a resection surface of the vertebra; wherein the first and second dimensions define at least one of the bone apposition surface and the articulating surface;
wherein the semispherical surface is incorporated in a ball and socket joint when the selected prosthesis is attached to the resected vertebra,
wherein the articulating surface is concave and comprises one or more planar portions,
wherein each of the components is configured with an aperture that extends completely there through.

2. The spinal implant kit of claim 1, wherein the selected prosthesis comprises a superior facet prosthesis, wherein the first facet is a natural superior facet.

3. The spinal implant kit of claim 2, wherein the first dimension comprises a resection angle ($\alpha$) defining an orientation of the bone apposition surface and the second dimension comprises a facet angle ($\beta$) defining an orientation of the articulating surface.

4. The spinal implant kit of claim 3, wherein the selected prosthesis further comprises:
an implant pedicle saddle point positioned to substantially overlie S1 when the selected prosthesis is attached to the resected vertebra; and
a radius of articulation (R) defining a radius of curvature of the articulating surface.

5. The spinal implant kit of claim 3, wherein a ranges in magnitude from about 30° to about 70° and $\beta$ ranges from about 60° to about 100°.

6. The spinal implant kit of claim 2, wherein the first and second dimensions are determined by measuring an x offset (X1) between S1 and P1 and a y offset (Y1) between S1 and PI and selecting first and second dimensions that are predetermined for a given Xl value and a given YI value.

7. The spinal implant kit of claim 2, wherein the articulating surface of the selected prosthesis has a most medial and anterior point (P1), a most posterior and lateral point (P4), and an implant pedicle saddle point positioned to substantially overlie S1 when the selected prosthesis is attached to the resected vertebra, wherein the first and second dimensions are selected from the group consisting of a resection angle ($\alpha$) defining an orientation of the bone apposition surface, an x offset (Xl) between S1 and PI, a y offset (Yl) between SI and PI, an x offset (X4) between SI and P4. a y offset (Y4) between S1 and P4, a facet angle ($\beta$) defining an orientation of the articulating surface, and a facet articulation radius (R) defining a radius of curvature of the articulating surface.

8. The spinal implant kit of claim 1, wherein a second selected prosthesis comprises a third and fourth prosthesis that comprise an inferior facet prostheses for replacing a second facet of the at least one removed facet.

9. The spinal implant kit of claim 8, wherein the articulating surface of the second selected prosthesis has a radius of articulation (IR) defining a radius of curvature of the articulating surface, wherein the second selected prosthesis further comprises an implant pedicle saddle point positioned to substantially overlie S1 when the second selected prosthesis is attached to the resected vertebra, wherein the first dimension comprises a resection angle (Iα) defining an orientation of the bone apposition surface and the second dimension comprises a z offset (Z) between Si and a center of IR.

10. The spinal implant kit of claim 8, wherein the first and second dimensions are determined by measuring one or more of an x offset (IX) between S1 and a second pedicle saddle point (S2) of an adjacent vertebra, a y offset (IY) between S1 and S2 and a z offset (IZ) between S I and S2, and selecting first and second dimensions that are predetermined for one or more of a given IX value, a given IY value, and a given IZ value.

11. The spinal implant kit of claim 8, wherein the articulating surface of the second selected prosthesis has a center of a radius of articulation (IR) defining a radius of curvature of the articulating surface and an implant pedicle saddle point positioned to substantially overlie S1 when the selected prosthesis is attached to the resected vertebra, wherein the first dimension is selected from the group consisting of a resection angle Iα defining an orientation of the bone apposition surface, a z offset (Z) between S1 and the center of IR, a facet angle (Iβ) defining an orientation of the articulating surface, and IR.

12. The spinal implant kit of claim 11, wherein the first dimension comprises Iα and the second dimension comprises Z.

13. The spinal implant kit of claim 12, wherein Iα and Z are determined by measuring one or more of an x offset (IX) between S1 and a second pedicle saddle point (S2) of an adjacent vertebra, a y offset (IY) between S1 and S2, and a z offset (IZ) between S1 and S2, and selecting Iα and Z that are predetermined for one or more of a given IX value, a given IY value, and a given IZ value.

14. The spinal implant kit of claim 12, wherein Iα ranges in magnitude from about 30° to about 70° and Z ranges from about 20 mm to about 40 mm.

15. A spinal implant kit for replacing at least one removed facet of a resected vertebra, wherein the resected vertebra has a pedicle saddle point (Sl) defining an intersection between a posterior pedicle bone surface and a longitudinal axis of a pedicle, wherein the at least one removed facet is a natural right superior facet, a natural left superior facet, a natural right inferior facet, or a natural left inferior facet, wherein the at least one removed facet has an articulating surface that, prior to removal of the at least one removed facet has a most medial and anterior point (P1), the spinal implant kit comprising:

a plurality of fixation elements; and a plurality of components for replacing a first facet of the at least one removed facet, wherein the components are of a single parametric design characterized by a first dimension and a second dimension;

wherein each of the components is of monolithic construction and comprises a generally convex semispherical surface, wherein the first and second dimensions vary in magnitude disproportionately relative to each other among the components such that a subset of the components is selectable to provide a selected prosthesis dimensioned to match a morphology of the resected vertebra.;

wherein a subset of the fixation elements is selectable to attach the selected prosthesis to the resected vertebra;

wherein, when the selected prosthesis is attached to the resected vertebra, the semispherical surface encircles at least one of the subset of the fixation elements and the selected prosthesis comprises an articulating surface positioned to approximate an original position of the first facet, wherein the plurality of components comprises a first prosthesis and a second prosthesis, each of which is independently selectable to provide the selected prosthesis, wherein the first dimension of the second prosthesis has a magnitude different from a magnitude of the first dimension of the first prosthesis, wherein either of the first and second prostheses is selectable to provide the selected prosthesis, wherein the articulating surface is concave and comprises one or more planar portions, wherein each of the components is configured with an aperture that extends completely therethrough.

16. The spinal implant kit of claim 15, wherein the first and second prostheses comprise superior facet prostheses, wherein the first facet is a natural superior facet.

17. The spinal implant kit of claim 16, wherein the first dimension comprises a resection angle (α) defining an orientation of a flat surface positioned to lie against a resection surface of the resected vertebra and the second dimension comprises a facet angle β, defining an orientation of the articulating surface.

18. The spinal implant kit of claim 17, wherein a ranges in magnitude from about 30° to about 70° and β ranges from about 60° to about 100°.

19. The spinal implant kit of claim 17 wherein α and β are determined by measuring an x offset (X1) between S1 and PI and a y offset (Y1) between S1 and PI and selecting α and β that are predetermined for a given X1 value and a given Y1 value.

20. The spinal implant kit of claim 19, wherein each of the first and second prostheses further comprises an implant pedicle saddle point positioned to substantially overlie Sl when the selected prosthesis is attached to the resected vertebra and a radius of articulation (R) defining a radius of curvature of the articulating surface of the first and second prostheses.

21. The spinal implant kit of claim 16, wherein the first and second dimensions are determined by measuring an x offset (X1) between S1 and P1 and a y offset (Y1) between S1 and P1 and selecting first and second dimensions that are predetermined for a given X1 value and a given Y1 value.

22. The spinal implant kit of claim 16, wherein each of the :first and second prostheses comprises an articulating surface having a most medial and anterior point (P1) and a most posterior and lateral point (P4), wherein each of the first and second prostheses further comprises an implant pedicle saddle point positioned to substantially overlie Si when the selected prosthesis is attached to the resected vertebra, wherein the first and second dimensions are selected from the group consisting of a resection angle (α) defining an orientation of a flat surface positioned to lie against a resection surface of the resected vertebra, an x offset (X1) between S1 and P1, a y offset (Y1) between SI and Pl, an x offset (X4) between S1 and P4, a y offset (Y4) between Sl and P4, a facet angle (β) defining an orientation of the articulating surface, and a facet articulation radius (R) defining a radius of curvature of the articulating surface.

23. The spinal implant kit of claim 1, further comprising a third and a fourth prosthesis which comprise inferior facet prostheses for replacing a second facet of the at least one removed facet.

24. The spinal implant kit of claim 23, wherein each of the third and fourth prostheses comprises an articulating surface having a radius of articulation (IR) defining a radius of curvature of the articulating surface and an implant pedicle saddle point positioned to substantially overlie Si when the selected prosthesis is attached to the resected vertebra, wherein the first dimension comprises a resection angle (Iα) defining an orientation of a flat surface positioned to lie against a resection surface of the resected vertebra and the second dimension comprises a z offset (Z) between S1 and a center IR.

25. The spinal implant kit of claim 24, wherein Iα and Z are determined by measuring one or more of an x offset (IX) between S1 and a second pedicle saddle point (S2) of an adjacent vertebra, a y offset (IY) between S1 and S2, and a z offset (IZ) between S1 and S2, and selecting Iα and Z that are predetermined for one or more of a given IX value, a given IY value, and a given IZ value.

26. The spinal implant kit of claim 23, wherein the first and second dimensions are determined by measuring one or more of an x offset (IX) between S1 and a second pedicle saddle point (S2) of an adjacent vertebra, a y offset (1Y) between S1 and S2, and a z offset (IZ) between S1 and S2, and selecting first and second dimensions that are predetermined for one or more of a given IX value, a given IY value, and a given IZ value.

27. The spinal implant kit of claim 23, wherein each of the third and fourth prostheses comprises an articulating surface having a center of a radius of articulation (IR) defining a radius of curvature of the articulating surface, wherein each of the third and fourth prostheses further comprises an implant pedicle saddle point positioned to substantially overlie when the selected prosthesis is attached to the resected vertebra, wherein the first dimension is selected from the group consisting of a resection angle (Iα) defining an orientation of a flat surface positioned to lie against a resection surface of the resected vertebra, a z offset (Z) between Si and the center of IR, a facet angle (Iβ) defining an orientation of the articulating surface, and 1R.

28. The spinal implant kit of claim 27, wherein the first dimension comprises Iα and the second dimension comprises Z.

29. The spinal implant kit of claim 28, wherein Iα and Z are determined by measuring one or more of an x offset (IX) between S1 and a second pedicle saddle point (S2) of an adjacent vertebra, a y offset (IY) between S1 and S2, and a z offset (IZ) between S1 and S2, and selecting Iα and Z that are predetermined for one or more of a given IX value, a given IY value, and a given IZ value.

30. The spinal implant kit of claim 28, wherein Iα ranges in magnitude from about 30° to about 70° and Z ranges from about 20 mm to about 40 mm.

31. The spinal implant kit of claim 15, further comprising third, fourth, fifth and sixth prostheses, each of which has a magnitude of the first dimension different from magnitudes of the first dimension of the remainder of the first, second, third, fourth, fifth, and sixth prostheses.

* * * * *